United States Patent
Broad

(10) Patent No.: US 12,263,355 B2
(45) Date of Patent: Apr. 1, 2025

(54) MULTI-LEAF COLLIMATOR

(71) Applicant: Elekta Limited, Crawley (GB)

(72) Inventor: Martin Broad, Crawley (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 17/906,181

(22) PCT Filed: Mar. 11, 2021

(86) PCT No.: PCT/EP2021/056281
§ 371 (c)(1),
(2) Date: Sep. 12, 2022

(87) PCT Pub. No.: WO2021/180904
PCT Pub. Date: Sep. 16, 2021

(65) Prior Publication Data
US 2023/0113879 A1  Apr. 13, 2023

(30) Foreign Application Priority Data

| Mar. 13, 2020 | (GB) | 2003664 |
|---|---|---|
| Mar. 13, 2020 | (GB) | 2003673 |
| Mar. 13, 2020 | (GB) | 2003679 |
| Mar. 13, 2020 | (GB) | 2003688 |
| Mar. 13, 2020 | (GB) | 2003694 |

(51) Int. Cl.
*A61N 5/10* (2006.01)
*G21K 1/04* (2006.01)

(52) U.S. Cl.
CPC .......... *A61N 5/1045* (2013.01); *G21K 1/046* (2013.01)

(58) Field of Classification Search
CPC ..... A61N 5/1045; A61N 5/1042; G21K 1/046
See application file for complete search history.

(56) References Cited

U.S. PATENT DOCUMENTS

| 6,459,769 B1 | 10/2002 | Cosman |
| 7,085,355 B1 | 8/2006 | Albagli et al. |
| 7,167,542 B2 | 1/2007 | Juschka et al. |
| 8,384,049 B1 | 2/2013 | Broad |
| 8,718,234 B2 | 5/2014 | Echner |

(Continued)

FOREIGN PATENT DOCUMENTS

| CN | 201226257 Y | 4/2009 |
| CN | 202128818 U | * 2/2012 |

(Continued)

OTHER PUBLICATIONS

Translation of JP2008206563A (Year: 2008).*

(Continued)

*Primary Examiner* — Dani Fox
*Assistant Examiner* — Mamadou Faye
(74) *Attorney, Agent, or Firm* — Schwegman Lundberg & Woessner, P.A.

(57) ABSTRACT

A leaf assembly for a multi-leaf collimator comprises a leaf and a leaf nut removably mounted within the profile of the leaf, the leaf nut comprising a threaded hole for receiving a leaf actuator screw oriented along a first axis in the plane of the leaf. The leaf nut is mounted within the leaf such that relative movement between the leaf nut and the leaf is prevented both linearly along the first axis and rotationally about the first axis.

15 Claims, 14 Drawing Sheets

(56) References Cited

U.S. PATENT DOCUMENTS

| | | | |
|---|---|---|---|
| 10,857,385 B2 | 12/2020 | Xiao et al. | |
| 12,138,482 B2 | 11/2024 | Broad | |
| 2002/0101959 A1 | 8/2002 | Kato et al. | |
| 2006/0067480 A1 | 3/2006 | Juschka et al. | |
| 2006/0193441 A1 | 8/2006 | Cadman | |
| 2009/0147917 A1 | 6/2009 | Mohr | |
| 2009/0262901 A1 | 10/2009 | Broad et al. | |
| 2011/0026683 A1 | 2/2011 | Broad et al. | |
| 2011/0199085 A1 | 8/2011 | Allen et al. | |
| 2012/0076269 A1 | 3/2012 | Roberts | |
| 2013/0000428 A1 | 1/2013 | Ji et al. | |
| 2015/0170778 A1 | 6/2015 | Echner et al. | |
| 2017/0087386 A1 | 3/2017 | Mellenberg et al. | |
| 2017/0128746 A1 | 5/2017 | Zwart et al. | |
| 2017/0148536 A1 | 5/2017 | Kawrykow et al. | |
| 2018/0012676 A1 | 1/2018 | Xu et al. | |
| 2018/0035969 A1 | 2/2018 | Jin | |
| 2018/0161602 A1 | 6/2018 | Kawrykow et al. | |
| 2019/0001153 A1 | 1/2019 | Jones et al. | |
| 2019/0054316 A1 | 2/2019 | Sheng et al. | |
| 2020/0185119 A1 | 6/2020 | Stahl et al. | |
| 2020/0304045 A1 | 9/2020 | Ye et al. | |
| 2021/0187322 A1 | 6/2021 | Zhong et al. | |
| 2021/0290979 A1 | 9/2021 | Liu et al. | |
| 2023/0100438 A1 | 3/2023 | Broad | |
| 2023/0101881 A1 | 3/2023 | Broad | |
| 2023/0110626 A1 | 4/2023 | Broad | |
| 2023/0173304 A1 | 6/2023 | Broad | |

FOREIGN PATENT DOCUMENTS

| | | | |
|---|---|---|---|
| CN | 204502129 U | 7/2015 | |
| CN | 205460495 | 8/2016 | |
| CN | 205656865 U | 10/2016 | |
| CN | 205843700 U | 12/2016 | |
| CN | 107929955 | 4/2018 | |
| CN | 110538387 A | 12/2019 | |
| DE | 3030332 | 2/1982 | |
| EP | 0314214 | 5/1989 | |
| EP | 3053628 | 8/2016 | |
| EP | 3266501 | 1/2018 | |
| GB | 2423909 | 9/2006 | |
| JP | 2006081585 | 3/2006 | |
| JP | 2008206563 A | * | 9/2008 |
| WO | 2008076035 | 6/2008 | |

OTHER PUBLICATIONS

Translation of CN-202128818-U (Year: 2012).*
"International Application Serial No. PCT/EP2021/056281, International Search Report dated Jun. 16, 2021", (Jun. 16, 2021), 3 pgs.
"International Application Serial No. PCT/EP2021/056281, Written Opinion dated Jun. 16, 2021", (Jun. 16, 2021), 5 pgs.
"United Kingdom Application Serial No. 2003664.6, Examination Report dated Aug. 13, 2020", (Aug. 13, 2020), 7 pgs.
"International Application Serial No. PCT EP2021 056270, International Search Report dated Jun. 17, 2021", (Jun. 17, 2021), 3 pgs.
"International Application Serial No. PCT EP2021 056270, Written Opinion dated Jun. 17, 2021", (Jun. 17, 2021), 5 pgs.
"United Kingdom Application Serial No. 2003673.7, Examination Report dated Sep. 15, 2020", (Sep. 15, 2020), 6 pgs.
"International Application Serial No. PCT EP2021 056278, International Search Report dated Jun. 16, 2021", (Jun. 16, 2021), 3 pgs.
"International Application Serial No. PCT EP2021 056278, Written Opinion dated Jun. 16, 2021", (Jun. 16, 2021), 6 pgs.
"International Application Serial No. PCT EP2021 056276, International Search Report dated Jun. 17, 2021", (Jun. 17, 2021), 3 pgs.
"International Application Serial No. PCT EP2021 056276, Written Opinion dated Jun. 17, 2021", (Jun. 17, 2021), 5 pgs.
"United Kingdom Application Serial No. 2003688.5, Examination Report dated Aug. 14, 2020", (Aug. 14, 2020), 6 pgs.
"United Kingdom Application Serial No. 2003694.3, Combined Search and Examination Report mailed Sep. 15, 2020", 7 pgs.
"International Application Serial No. PCT EP2021 056282, International Search Report dated Jun. 16, 2021", (Jun. 16, 2021), 3 pgs.
"International Application Serial No. PCT EP2021 056282, Written Opinion dated Jun. 16, 2021", (Jun. 16, 2021), 5 pgs.
"United Kingdom Application Serial No. 2003679.4, Examination Report dated Sep. 15, 2020", (Sep. 15, 2020), 8 pgs.
"U.S. Appl. No. 17/906,147 Preliminary Amendment Filed with Application", 8 pgs.
"U.S. Appl. No. 17/906,149 Preliminary Amendment Filed with Application", 7 pgs.
"U.S. Appl. No. 17/906,153 Preliminary Amendment Filed with Application", 8 pgs.
"U.S. Appl. No. 17/906,149, Non Final Office Action mailed Jun. 18, 2024", 12 pgs.
"U.S. Appl. No. 17/906,147, Notice of Allowance mailed Jul. 12, 2024", 8 pgs.
"U.S. Appl. No. 17/906,147, Corrected Notice of Allowability mailed Aug. 1, 2024", 2 pgs.
"U.S. Appl. No. 17/906,149, Response filed Aug. 20, 2024 to Non Final Office Action mailed Jun. 18, 2024", 7 pgs.
"U.S. Appl. No. 17/906,149, Notice of Allowance mailed Sep. 6, 2024", 7 pgs.
"U.S. Appl. No. 17/906,153, Non Final Office Action mailed Oct. 16, 2024", 13 pgs.
Machine Translation of CN-107929955, (2018).
"U.S. Appl. No. 17/906,179, Notice of Allowance mailed Nov. 1, 2024", 7 pages.
"U.S. Appl. No. 17/906,149, PTO Response to Rule 312 Communication mailed Nov. 15, 2024", 2 pages.
"U.S. Appl. No. 17/906,179, Corrected Notice of Allowability mailed Nov. 15, 2024", 2 pages.

* cited by examiner

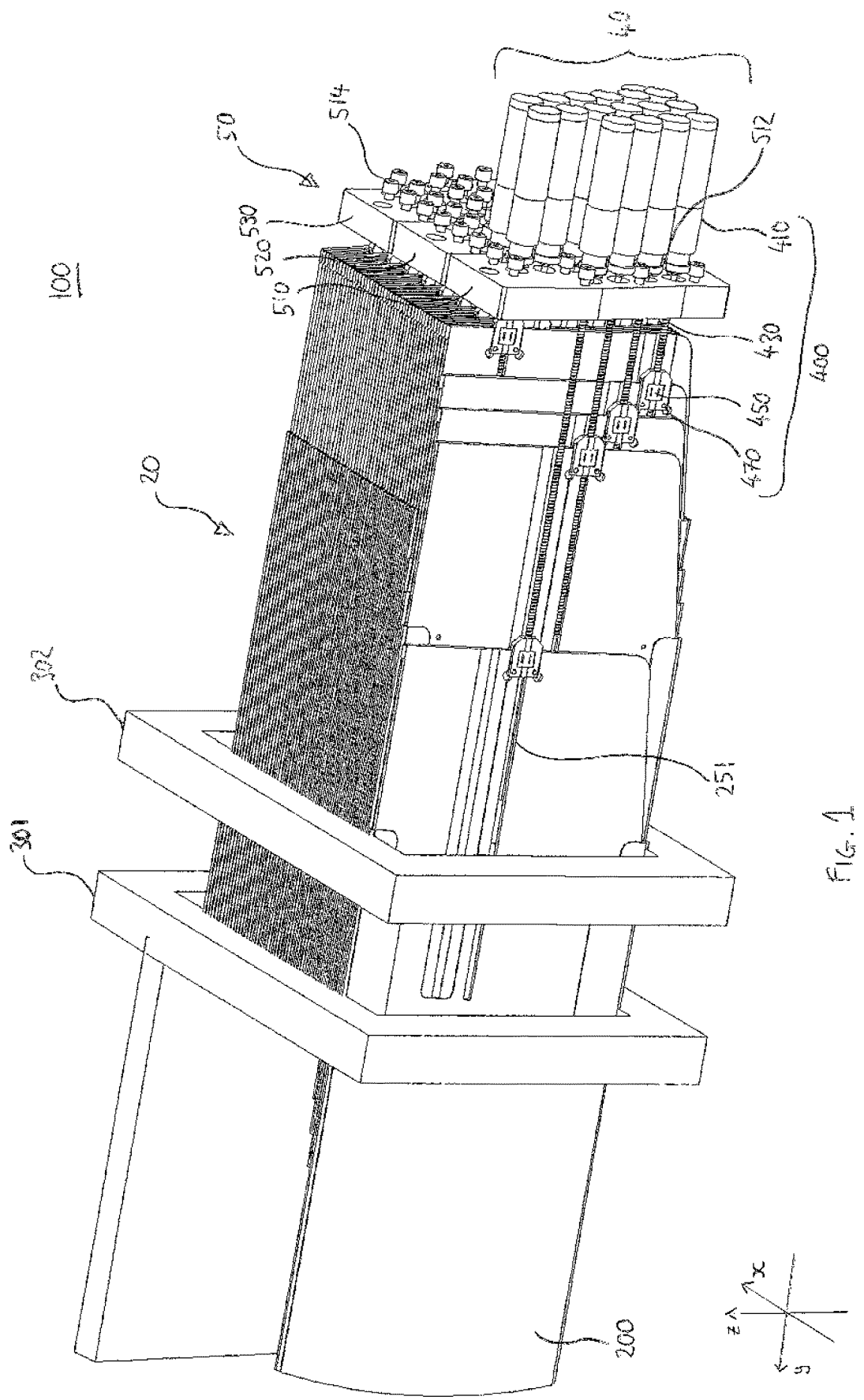

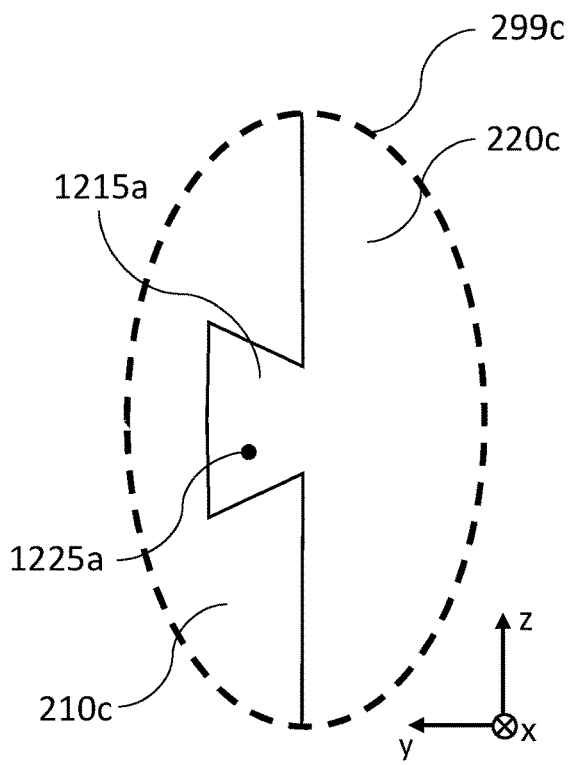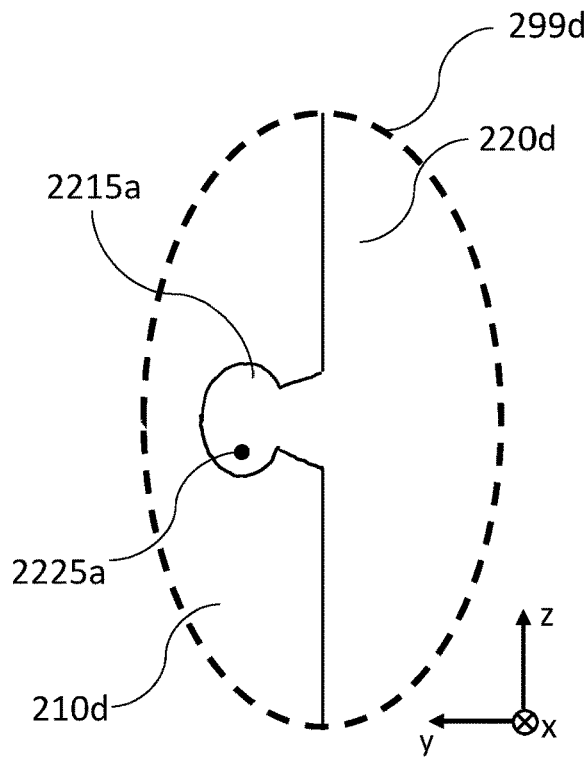
Fig. 2c　　　　　　　　Fig. 2d
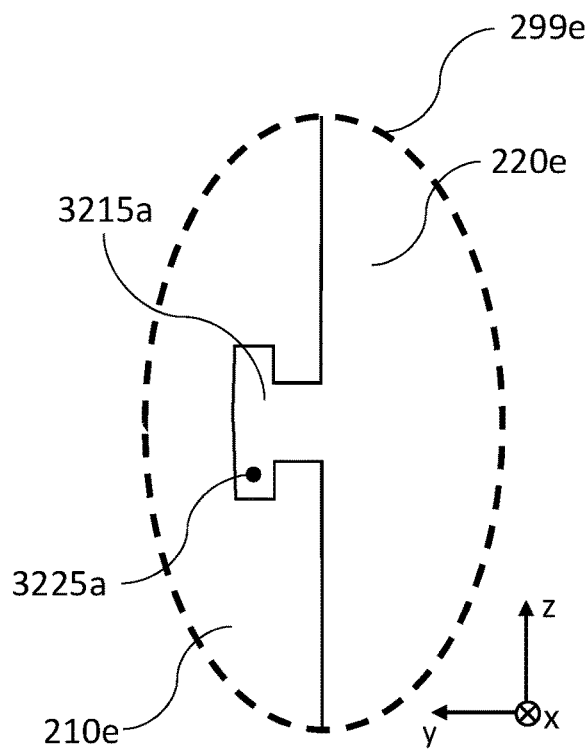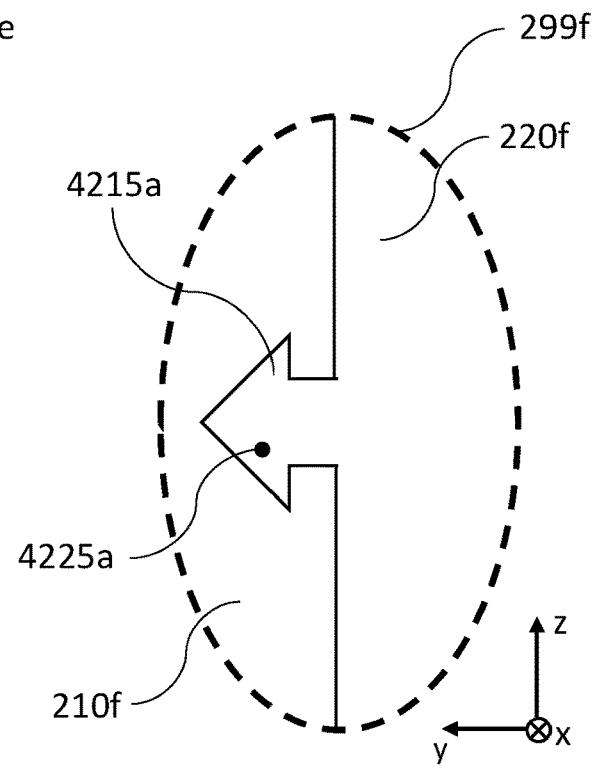
Fig. 2e　　　　　　　　Fig. 2f

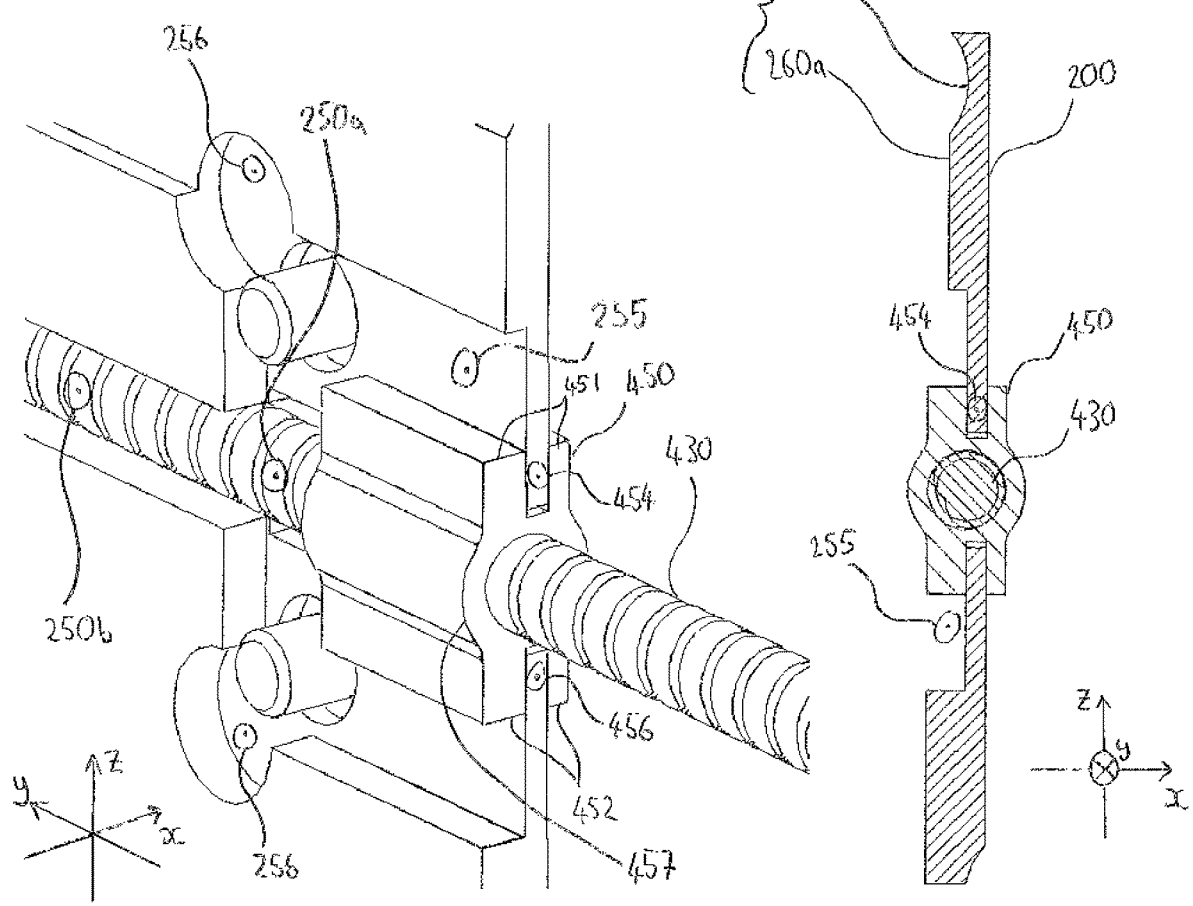

MULTI-LEAF COLLIMATOR

PRIORITY APPLICATIONS

This application is a U.S. National Stage Filing under 35 U.S.C. § 371 from International Application No. PCT/EP2021/056281, filed on Mar. 11, 2021, and published as WO2021/180904 on Sep. 16, 2021, which claims the benefit of priority to United Kingdom Application No. 2003664.6, filed on Mar. 13, 2020 and to United Kingdom Application No. 2003694.3, filed on Mar. 13, 2020 and to United Kingdom Application No. 2003688.5, filed on Mar. 13, 2020 and to United Kingdom Application No. 2003679.4, filed on Mar. 13, 2020 and to United Kingdom Application No. 2003673.7, filed on Mar. 13, 2020; the benefit of priority of each of which is hereby claimed herein, and which applications and publication are hereby incorporated herein by reference in their entireties.

FIELD

The present disclosure relates to a leaf nut for a multi-leaf collimator, a leaf nut holder for said leaf nut and a leaf assembly including a leaf, said leaf nut and said leaf nut holder. The present disclosure also relates to a multi-leaf collimator including said leaf assembly.

The present disclosure also relates to a leaf for a multi-leaf collimator.

The present disclosure also relates to a leaf drive mount for a multi-leaf collimator, and a multi-leaf collimator having said mount. The present disclosure also relates to a drive arrangement for a multi-leaf collimator and a multi-leaf collimator having the same.

The present disclosure also relates to a multi-leaf collimator module for a radiotherapy device, and a multi-leaf collimator comprising the same.

The present disclosure also relates to a leaf actuator for a multi-leaf collimator, and a multi-leaf collimator comprising the same.

BACKGROUND

Radiotherapeutic apparatus involves the production of a beam of ionising radiation, usually x-rays or a beam of electrons or other sub-atomic particles. This is directed towards a cancerous region of a patient (e.g. a tumour), and adversely affects the cancerous cells thereby reducing the prevalence thereof. The beam is delimited so that the radiation dose is maximised in the cancerous cells and minimised in healthy cells of the patient, as this improves the efficiency of treatment and reduces the side effects in a patient.

In a radiotherapy apparatus, the beam can be delimited using a beam limiting device such as a 'multi-leaf collimator' (MLC). This is a collimator which consists of a large number of elongate thin leaves arranged side by side in an array. The leaves are usually made from a high atomic numbered material, usually tungsten, so that they are substantially opaque to the radiation.

Each leaf is moveable longitudinally so that its tip, or leading edge, can be extended into or withdrawn from the radiation beam. All the leaves can be withdrawn to allow the radiation beam to pass through, or all the leaves can be extended so as to block the radiation beam completely. Alternatively, some leaves can be withdrawn and some extended so as to define any desired shape, within operational limits. The array of leaf tips can thus be positioned so as to define a variable edge to the collimator. A multi-leaf collimator usually consists of two banks of such arrays (i.e. leaf banks), each leaf bank projecting into the radiation beam from opposite sides of the collimator. The variable edges provided by the two leaf banks thus collimate the radiation beam to a chosen cross-sectional shape, usually that of a target tumour volume to be irradiated. That is, the two leaf banks combine to provide an aperture of variable shape for shaping the radiation beam.

It is important that the driving mechanisms for driving the individual leaves are robust, low friction and easy to install and maintain. Fulfilling one or more of these criteria can increase the complexity and cost of manufacture of the multi leaf collimator.

The leaves of the multi leaf collimator provide the important function of attenuating the radiation to protect healthy tissue surrounding target tissue. As explained above, the leaves are made from tungsten or other high-atomic-number materials. However, such material is expensive, heavy and difficult to process.

The leaves of the leaf banks are driven by an array of leaf drive units. Each leaf drive unit includes a leaf motor arranged to rotate one of the components of the leaf drive unit relative to another. This relative rotational motion translates into linear motion of a corresponding leaf connected at the opposite end of the leaf drive unit to the leaf motor.

It is desirable that the leaf drive units are easily mounted, removed and replaced in the multi leaf collimator to improve repair and maintenance efficiency and reduce radiotherapy device downtime.

The movement of the leaf banks as a unit and the movement of the individual leaves may be carried out for different purposes. The movement of the individual leaves may be carried out to define the shape of the radiation beam, whereas the movement of the leaf banks may be carried out in order to move the shaped aperture provided by the leaves relative to the axis of the radiation beam. The movement of the leaf banks and individual leaves may be carried out independently of each other and the movements may be carried out sequentially or concurrently depending on the requirements of the application. This allows greater flexibility than allowing individual leaf motion alone.

However, the mechanism or structure for moving and guiding the leaves can lead to inaccuracies in the positioning of the leaves relative to the substrate and/or the radiation beam. In addition, misalignment of the leaf banks relative to each other can affect the ability of the leaves of one of the leaf banks to interdigitate with, or match the position of, the leaves of the other leaf bank.

Existing solutions to this problem include systems employing high-precision linear actuators to move the leaf banks and leaves. However, such systems are expensive and increase the volume and/or footprint of the multi-leaf collimator, which can limit its integrability in some radiotherapy devices.

It is desirable to provide a multi-leaf collimator which addresses the abovementioned problems.

The individual leaves may be moved independently of each other out to define the shape of the radiation beam by defining the shape of the aperture. In some cases, the leaves are moved in unison to define the position of the radiation beam by defining the position of the aperture. In use, the shape and/or position of the aperture may need to be changed quickly. For example, in some applications, MRI imaging of the treated subject is carried out in real time to track the position of a tumour to be irradiated by the radiotherapy device. In this case, the silhouette of the tumour from the perspective of the direction of travel of the radiation beam may change, for example owing to movement of the patient (e.g. due to breathing) during treatment. The shape and position of the multi-leaf collimator aperture can be changed so that the shape and position of the radiation beam tracks the changing shape and/or position of the tumour silhouette. Thus, the beam consistently irradiates as much of the tumour as possible while irradiating as little as possible of the surrounding healthy tissue, even when the tumour moves.

The speed of movement of the individual leaves is important in ensuring that the change in shape and/or position of the aperture keeps up with the changing shape and/or position of the tumour silhouette. The leaf actuators (i.e. the means for moving the individual leaves) play an important role in achieving suitable leaf speeds. However, the form and mechanism of the leaf actuators govern not only the speed, but also the accuracy of positioning of the individual leaves, and the stability and durability of the leaf actuators themselves. Often, there is a trade-off between speed on one hand and accuracy of positioning, stability and/or durability on the other.

It is also desirable to provide an accurate leaf actuator having high speed, high durability and high stability.

SUMMARY

Aspects and features of the present invention are set out in the accompanying claims.

There is provided a leaf assembly for a multi-leaf collimator, comprising: a leaf; a leaf nut removably mounted within the profile of the leaf, the leaf nut comprising a threaded hole for receiving a leaf actuator screw oriented along a first axis in the plane of the leaf; the leaf nut being mounted within the leaf such that relative movement between the leaf nut and the leaf is prevented both linearly along the first axis and rotationally about the first axis.

The leaf nut is positioned in the leaf tail to provide a simpler drive design and more accurate leaf positioning. The leaf nut is not permitted to rotate or move longitudinally relative to the leaf (so that rotation of the leaf actuator screw (usually a leadscrew) causes longitudinal movement of the nut and leaf), but a small amount of vertical movement between the leaf nut and leaf is permitted which allows for misalignment between the motor, leaf actuator screw and the leaf nut.

Removable Leaf Nut

Instead of the leaf nut being an integral part of the leaf or the tail portion of the leaf, the leaf nut is removably mounted within the profile of the leaf. Advantageously, this allows the nut to be replaced, for example if worn or damaged, without replacement of the leaf or tail portion of the leaf. In embodiments, the leaf nut is removably mounted so that no destruction of any part of the leaf or leaf nut is required in order to remove the leaf nut from the leaf.

In embodiments, the leaf nut is removably mounted via the selective interlocking of at least a part of the leaf nut with at least a part of the leaf. The interlocking is selective in that the leaf nut can be moved from a position in which the at least a part of the leaf nut and at least a part of the leaf are interlocked, to a position in which there is no interlocking between the leaf nut and the leaf. The interlocking limits the movement of the leaf linearly in at least one pair of two opposing directions and/or rotationally. Advantageously, fewer fixing means are required to limit movement of the leaf nut in the ways described herein. In addition, the interlocking assists reliable positioning of the leaf assembly components during repair/replacement so that the complexity and cost of repair/replacement is reduced.

Thus, it may be understood that the leaf nut is movable from a third position, in which the leaf nut is interlocked with the leaf, along an axis to a fourth position in which the leaf nut is free from the leaf. In embodiments, the axis may be the first axis described herein (i.e. in the longitudinal direction of the leaf). The first axis defines a first direction and a second direction opposite the first direction and the leaf nut is movable in the second direction from the third position to the fourth position (the first direction being from the tail to the tip of the leaf). Advantageously, the leaf nut can be removed more easily from the tail portion of the leaf without interfering with the leaf assembly corresponding to any adjacent leaf.

In embodiments, the interlocking parts of the leaf nut and leaf include a recessed structure on one of the leaf nut and leaf and a corresponding protruding structure on the other of the leaf nut and leaf for insertion into the recessed structure. Advantageously, this provides a simple mechanism for preventing movement of the leaf nut relative to the leaf in one axis (perpendicularly from either side of the protruding or recessed structure) while allowing movement in an axis perpendicular to this (e.g. into/out of the recessed structure).

In embodiments, the recessed structure or protruding structure is elongate, thus allowing movement in a third axis perpendicular to these two axes (i.e. parallel to the lengthwise direction of the recessed structure or protruding structure). For example, the recessed structure may be a slot or groove on one of the leaf nut and leaf, and the protruding structure may be a structure on the other of the leaf nut and leaf corresponding to the slot or groove for engaging the slot or groove.

Alternatively, or in addition, the protruding structure includes a rib or spine on one of the leaf nut and leaf, and the recessed structure is a structure on the other of the leaf nut and leaf for engaging the rib or spine. In embodiments, the recessed structure is on the leaf nut and the protruding structure is the body of the leaf itself. That is, the recessed structure receives the body of the leaf itself.

Alternatively, or in addition, the leaf nut is removably mounted to the leaf via fixing means, such as a screw, bracket, frame, mount, clip, clasp, catch or holder. Advantageously, fewer machined features in the leaf nut and/or tail portion of the leaf are required in order to limit movement of the leaf nut. Fewer machined features reduces the complexity of machining in the leaf or leaf nut, which reduces manufacturing complexity and cost.

Prevention and Limitation of Leaf Nut Movement

The interlocking parts and/or fixing means may prevent or limit movement of the leaf nut relative to the leaf in a number of ways. Movement may be prevented or limited linearly along an axis or rotationally around an axis. Here, prevention means substantially no movement (within engineering tolerances) and limitation means some limited movement is allowed.

Movement of the leaf nut relative to the leaf is prevented, rather than merely limited, along the axis of movement of the leaf in use (i.e. in the first and second directions described herein, that is into and out of the path of the radiation beam). If this such movement is not prevented, rotations of the leaf actuator screw may translate into linear movement of the leaf nut without translating into the expected degree of linear movement of the leaf. Inaccuracies in leaf positioning may occur as a result.

For similar reasons, rotational movement about the axis of movement of the leaf (either clockwise or anticlockwise) is also prevented so that the rotational movement of the leaf actuator screw does not translate into rotation of the leaf nut instead of linear movement of the leaf. Such movement is undesirable, because leaf drive positioning mechanisms rely on a fixed relationship between the linear displacement of the leaf and rotation of the leaf actuator screw.

Unless the aforementioned linear and rotational movements are prevented, complex compensation mechanisms, sensing-motion feedback loops and/or control methods may be needed to ensure accurate driving and positioning of the leaf.

In embodiments, the leaf nut comprises an engaging portion configured to engage the leaf (e.g. a face of the leaf) to constrain rotational movement of the leaf nut relative to the leaf about the first axis. For example, the leaf nut comprises a slot for receiving a portion of the leaf and the walls of the slot engage the face of the leaf. In embodiments, the leaf nut is mounted into the tail portion of the leaf and is constrained by a profile that fits over the edges of the tail to resist the torque reaction from the leaf actuator screw. The profile and the tail portion are designed so that minimal clearance therebetween is attained to stop rotation of the nut to reduce 'backlash' (rotation of the leaf actuator screw without translation into linear motion of the leaf). In other embodiments, the leaf includes a recess configured to receive the engaging portion of the leaf. For example, the leaf nut includes a spine and the leaf includes a slot in the plane of the leaf for receiving the spine.

The rotational movement of the leaf nut relative to the leaf around any axis other than the axis of the leaf actuator screw is prevented primarily by the leaf actuator screw itself. However, the interacting features of the leaf nut and leaf may also prevent such rotational movement.

Some linear movement of the leaf nut relative to the leaf in certain axes can be beneficial. In embodiments, the leaf nut is movable relative to the leaf in an axis extending out of the plane of the leaf (e.g. normal to the plane of the leaf). Alternatively, or in addition, the leaf nut is movable in the plane of the leaf in an axis lying across the axis of movement of the leaf (e.g. in the plane of the leaf perpendicular to the axis of movement of the leaf). That is, linear movement of the leaf nut relative to the leaf along a second axis is limited between a first and second position along the second axis, wherein the second axis lies across (e.g. perpendicular to) the first axis. Advantageously, by allowing such movement, misalignments between the leaf and the other leaf actuator components (the leaf actuator screw and/or the leaf actuator motor) can be better accommodated. This increase in alignment tolerance ultimately reduces the stress and/or wear on the leaf drive components (e.g. the leaf drive motor, the leaf nut and/or the leaf actuator screw) in use.

Allowing the above described movement in either one of these axes may be achieved by providing one or more of the interlocking protrusion-recess arrangements described herein.

In embodiments, relative movement of the leaf nut out of the plane of the leaf is prevented in order to avoid leaf nut interference with adjacent leaves, and the leaf nut is movable in the plane of the leaf in the axis lying across the direction of movement of the leaf.

In embodiments the aforementioned movements (those in the axis lying across the axis of movement of the leaf and/or the axis extending out of the plane of the leaf) are limited along the respective axis. In embodiments, each recess has a stop (e.g. the floor of the recess or a strut, protrusion or rib in the recess).

Alternatively, or in addition, each protruding part includes a stop (e.g. a flange or shoulder) or has a stop associated therewith (e.g. the base from which the protrusion protrudes). The stop limits the movement between the first and second positions by preventing further movement of the protrusion into the recess. Advantageously, this prevents excessive movement of the leaf nut and mitigates the risk of damage to the leaf assembly and or leaf drive unit during installation, repair or operation. For example, the limited movement may prevent the leaf nut from impinging upon the space designated for a part of an adjacent leaf or the leaf nut of an adjacent leaf.

In embodiments, the aforementioned movements (those in the axis lying across the axis of movement of the leaf and/or the axis extending out of the plane of the leaf) are limited between a first and a second position along the respective axis. To achieve this, two recess/protrusion arrangements are provided, each arrangement including at least one of the aforementioned stops. That is, movement is limited between a first position and a second position by the physical interaction between the leaf nut and the leaf. Alternatively, or in addition, movement is limited by a leaf nut holder (described below).

In embodiments, the interlocking parts also prevent rotation of the leaf nut relative to the leaf. Alternatively, or in addition, fixing means, such as the leaf nut holder, may prevent rotation of the leaf nut relative to the leaf.

Leaf Nut Holder

In embodiments, the leaf assembly includes a leaf nut holder arranged to hold the leaf nut and prevent or limit the movement of the leaf nut relative to the leaf. The leaf nut holder is removably coupled to the leaf to allow ease of repair or replacement of leaf nut and/or the leaf nut holder itself. The leaf nut holder is a frame, mount, clip, clasp or any other structure which interacts with both the leaf nut and the leaf to fasten the leaf nut to the leaf.

In embodiments, the leaf nut holder, when fastened to the leaf, is arranged to limit movement of the leaf nut relative to the leaf longitudinally (i.e. along the first axis in the first and second directions), while allowing relative movement laterally in the plane of the leaf (along the second axis in the third and fourth directions) and/or perpendicular to the plane of the leaf (along the third axis in the fifth and sixth directions).

In embodiments, the leaf and the leaf nut holder cooperate to limit movement of the leaf nut relative to the leaf along the first axis. For example, the leaf or the leaf nut includes a stop for preventing movement of the leaf nut in the first direction from a third position in which the leaf nut is mounted in the leaf, while the leaf nut holder is arranged to provide a stop to prevent movement of the leaf nut from the third position in the second direction toward a fourth position in which the leaf nut is free from the leaf.

In embodiments, the leaf nut holder has means (e.g. an aperture or a recess) arranged to accommodate at least a portion of the leaf nut. The edges of the aperture (or recess) limit lateral movement of the leaf nut relative to the leaf between the first position and a second position while preventing movement of the leaf nut relative to the leaf in the longitudinal direction (i.e. from the third position towards the fourth position).

The leaf nut holder and leaf include interlocking means of any of the varieties described earlier in relation to the leaf nut and leaf (e.g. recess/protrusion pairs). The interlocking means prevent relative movement between the leaf nut holder and the leaf in one or more of the longitudinal direction (along the first axis), lateral direction (along the second axis) and the direction perpendicular to the plane of the leaf (along the third axis). The limitation in movement of the leaf nut holder and the interaction between the leaf nut holder and the leaf nut allows the leaf nut holder to limit movement of the leaf nut relative to the leaf in any of the ways described herein. Advantageously, fewer fixing means are required in order to limit movement of the leaf nut holder to, in turn, properly limit movement of the leaf nut in the ways described herein. Fewer fixing means simplifies the manufacturing process and reduces the probability of parts that may interfere with the operation of the multi leaf collimator.

Alternatively, or in addition, leaf nut holder is removably mounted to the leaf via fixing means, such as a screw, bracket, frame, mount, clip, clasp, catch or holder. Advantageously, fewer features in the leaf nut holder and/or tail portion of the leaf are required to limit the movement of the leaf nut holder to, in turn, limit movement of the leaf nut in the ways described herein. Fewer features reduces the complexity of machining in the leaf or leaf nut holder, which reduces manufacturing complexity and cost.

In embodiments, the leaf nut holder includes a slot for receiving an edge of the leaf and preventing movement of the leaf nut holder relative to the leaf along the first direction and/or out of the plane of the leaf. For example, the leaf nut holder may include a blind slot arranged to receive an edge of the tail portion of the leaf. The blind slot allows the leaf nut holder to straddle the edge of the tail portion so as to limit movement of the leaf nut holder relative to the leaf in the axis extending out of the plane of the leaf. The floor of the blind slot acts as a stop for limiting the movement of the leaf nut holder relative to the leaf in the first direction (i.e. longitudinally in the first direction into the path of the radiation beam). The use of a blind slot in this way aids the removability of the leaf nut holder from the leaf as movement of the leaf nut holder relative to the leaf is permitted longitudinally in the second direction opposite the first direction. Thus, the leaf nut holder can be slid backwards to disengage the edge of the leaf from the blind slot and remove it for repair or replacement.

In embodiments, the leaf nut is manufactured from plastic. Advantageously, the leaf nut material needs no lubrication and has a long service life. The leaf nut holder may be manufactured from steel or any other suitable metal alloy. Alternatively, the leaf nut holder may be manufactured from plastic. The leaf may be manufactured from tungsten. Optionally, a tail portion of the leaf may be manufactured from a different material (e.g. steel) to allow for ease of machining the aforementioned interlocking parts into the leaf.

In embodiments, the leaf nut and leaf nut holder are manufactured as one piece as a plastic moulding so that a flexible connection is created between the leaf nut holder and leaf nut to allow for misalignment problems as part of the moulding. For example, the moulding may include a thin (flexible) section connecting the leaf nut to the leaf nut holder. The flexible section is configured to flex so as to allow relative movement between the leaf nut and the leaf nut holder in one or more directions while remaining relatively stiff in the leaf travel direction so as to prevent or minimise movement in this direction. Thus, the flexible section is configured to prevent relative movement between the leaf nut and leaf nut holder along the first axis, so that force from the leaf actuator screw can be transmitted to the leaf efficiently (without backlash). The flexible section may be configured to allow relative movement of the leaf nut between the first position and second position as described herein to accommodate misalignment between the leaf and the leaf actuator components. The flexible section may have a ribbon-like form to provide this functionality and the lengthwise direction of the ribbon may be parallel to the leaf travel direction with the leaf nut connected to the ribbon along one edge of the ribbon and the leaf nut holder connected to the ribbon along the opposing edge of the ribbon. The folding, bending or flexing of the ribbon along lines parallel to its lengthwise direction permits the relative movement of the leaf nut relative to the leaf nut holder.

Accommodating Features in the Leaf

In embodiments, the tail portion of the leaf is configured to accommodate the leaf nut and/or the leaf nut holder. The tail portion of the leaf may also be configured to facilitate the movement (and/or prevention/limitation of movement) of the leaf nut and/or leaf nut holder in use. Alternatively, or in addition, the tail portion is configured to facilitate the fixture and removal of the leaf nut and/or leaf nut holder from the leaf.

In embodiments, the leaf includes a slot for receiving the leaf actuator screw. The slot lies in a lengthwise direction of the leaf (i.e. along the first axis). The slot is through the whole thickness of the leaf and has a width suitable for accommodating the leaf actuator screw while allowing unimpeded rotation thereof relative to the leaf. Advantageously, the slot allows the leaf actuator screw to extend into the profile of the leaf, which creates a more compact leaf assembly.

In embodiments, a section of the slot is for receiving at least a portion of the leaf nut. The section of the slot is wider than the remaining part of the slot. The leaf nut is arranged to move along the slot between the third and fourth positions. This facilitates ease of removal and replacement of the leaf nut because the leaf nut can slide back and forth along the slot and does not need to be otherwise held in place. For example, the leaf nut can be removed by removing the leaf nut holder holding the leaf nut in place, then sliding the leaf nut along the section of the slot from the third position (in place for use) to the fourth position (in which it is free from the leaf). When the leaf nut holder is removed, the movement of the leaf nut is restricted to being between the third and fourth positions by the slot, thereby reducing the risk the leaf nut will drop out. Thus, the slot aids safe, convenient and reliable removal and replacement of the leaf nut.

In embodiments, the leaf includes a rib spanning the slot. The rib has a curve in the plane perpendicular to the plane of the leaf and the first axis so that it follows the cylindrical surface of the leaf actuator screw. The inner radius of curvature of the rib is greater than the (outer) radius of the leaf actuator screw. The rib facilitates ease of mounting of the leaf actuator screw by providing a guiding surface during installation, removal and replacement of the leaf actuator screw.

In embodiments, the leaf includes a seat recessed from a face thereof for receiving the leaf nut holder, wherein the seat is arranged to prevent movement of the leaf nut holder in at least one of the two opposing directions in the first and/or second axis. The walls of the recess prevent movement by engaging with an edge of the leaf nut holder. Advantageously, the seat allows ease of placement of the leaf nut holder prior to and during fixing of the leaf nut holder to the leaf. For example, the walls provide locating means for aligning corresponding fixing holes in the leaf nut holder and leaf nut for screws or other fixing means to pass therethrough to fix the leaf nut holder to the leaf.

In embodiments, the leaf nut and/or leaf nut holder has a first cross-sectional profile in a plane perpendicular to both the plane of the leaf and the first axis, and the leaf has a recess having a second cross-sectional profile on one face thereof matching at least a part of the first cross-sectional profile. In this way, the recess can receive a respective leaf nut and/or leaf nut holder corresponding to the leaf assembly of an adjacent leaf. That is, the recess is arranged to receive a portion of the leaf nut and/or leaf nut holder of an adjacent leaf while allowing (i) movement of the leaf nut holder and leaf nut of the adjacent leaf back and forth along the recess as the leaf and adjacent leaf move relative to each other and (ii) movement of the leaf nut between the first and second positions described herein. Advantageously, the leaf nut holder and/or leaf nut can have a profile which is thicker than the maximum thickness of the leaf without interfering with the motion of adjacent leaves. Thus, the leaf nut and/or leaf nut holder can be thicker and more robust.

To reduce the amount of tungsten (which is heavy and expensive) in the leaf, the tail portion of the leaf which is not required to attenuate the beam is either fabricated from a different material to the leaf or is thinner or narrower. Advantageously, the resultant leaf is lighter and/or cheaper and/or more easily fabricated. If the tail portion is fabricated from a different material, the tail portion can be more easily machined.

Relative Attenuation Factors

Therefore, there is provided a leaf for a multi-leaf collimator including a leaf portion for delineating a beam of radiation, the leaf portion having first attenuation factor; and a tail portion having a second attenuation factor, the first attenuation factor being greater than the second attenuation factor.

The first and second attenuation factors characterise the amount of radiation attenuation when the leaf portion and tail portion, respectively, are placed wholly in the path of the radiation beam in the orientation of intended use of the leaf. The attenuation factors are measurable at the wavelength(s) (or energies) of the radiation emitted by the radiotherapy device in which the multi-leaf collimator is configured to be installed. The range of energies in a Linac (linear accelerator-type) radiotherapy device can be 6 MeV to 25 MeV, or a subrange therein, e.g. 6 MeV to 10 MeV. The attenuation factors are those which are measurable in the direction of propagation the beam of radiation when the multi-leaf collimator is in situ in the radiotherapy device. Therefore, the attenuation factors are those measurable from a first edge of the leaf to a second edge of the leaf opposite the first edge of the leaf, the first and second edges being those lying perpendicular to the direction of propagation of the beam when the leaf is in situ in the multi leaf collimator and when the multi leaf collimator is in situ in the radiotherapy device.

The first attenuation factor is measurable by irradiating the leaf portion normal to its first edge with a uniform intensity radiation beam having the wavelength spectrum of the type used in the radiotherapy device. If leaf portion is placed so that its silhouette falls entirely within the cross section of the radiation beam, the attenuation factor can be ascertained by measuring total power attenuation of the beam due to the leaf portion. A model or calculation can take the place of the measurement. The skilled person knows how to calculate the level of attenuation based on the aforementioned conditions based on the material and dimensions of the leaf portion and the radiation beam characteristics. If the attenuation factor of the tail portion is measured or calculated in the same way using the same beam (i.e. inter alia the same power, same wavelength spectrum, same beam radius), the attenuation factors can be compared to ascertain the relative attenuation factor of the leaf portion and tail portion.

In embodiments, the first attenuation factor is greater than the second attenuation factor due to one or more of the following relative attributes of the leaf portion and tail portion.

i. The leaf portion has a greater thickness than the tail portion.
ii. The leaf portion material has a greater attenuation coefficient than the tail portion material.
iii. The leaf portion has a greater width than the tail portion.
iv. The leaf portion has a greater length than the tail portion.

A useful measure to further distinguish the characteristics of the leaf portion and the tail portion is the attenuation factor per unit length. The attenuation factor per unit length of the leaf portion can be ascertained by dividing the attenuation factor by the length of the leaf portion (the dimension in the first direction described herein from tip to tail of the leaf portion). The attenuation factor per unit length of the tail portion can be ascertained by dividing its attenuation factor by the length of the tail portion (the dimension in the first direction described herein from tip to tail of the tail portion). The lengths may be the average (i.e. mean) lengths of the leaf and tail portions.

Embodiments provide a leaf for a multi-leaf collimator including a leaf portion for delineating a beam of radiation, the leaf portion having first attenuation factor per unit length; and a tail portion having a second attenuation factor per unit length, the first attenuation factor per unit length being greater than the second attenuation factor per unit length. That is, the first attenuation factor divided by the mean length of the leaf portion is greater than the second attenuation factor divided by the mean length of the tail portion.

Another useful measure to distinguish the characteristics of the leaf portion and the tail portion is the attenuation factor per unit width. The attenuation factor per unit width of the leaf portion can be ascertained by dividing the attenuation factor by the width of the leaf portion (the dimension in the fourth direction described herein from the first edge to the second edge of the leaf portion, i.e. in the dimension parallel to the direction of propagation of the radiation beam). The attenuation factor per unit width of the tail portion can be ascertained by dividing its attenuation factor by the width of the tail portion (the dimension in the fourth direction described herein from the first edge to the second edge of the tail portion). The above described widths may be the average (i.e. mean) widths of the leaf and tail portions.

Embodiments provide a leaf for a multi-leaf collimator including a leaf portion for delineating a beam of radiation, the leaf portion having first attenuation factor per unit width; and a tail portion having a second attenuation factor per unit width, the first attenuation factor per unit width being greater than the second attenuation factor per unit width. That is, the first attenuation factor divided by the mean width of the leaf portion is greater than the second attenuation factor divided by the mean width of the tail portion.

A yet further useful measure to distinguish the characteristics of the leaf portion and the tail portion is the attenuation factor per unit area of the face of the leaf. The reason this metric is useful is that it provides a comparison of the relative attenuating properties of the leaf portion and tail portion which is independent of both the relative mean length and relative mean width of the tail portion.

The attenuation factor per unit area of the leaf portion can be ascertained by dividing the attenuation factor by the area of the face (i.e. one face) of the leaf portion. The area of the face of the leaf may be the average (i.e. mean) width of the leaf portion (the dimension in the fourth direction described herein from the first edge to the second edge of the leaf portion) multiplied by the average (i.e. mean) length of the leaf portion (the dimension in the first direction described herein from tip to tail of the leaf portion). However, other means for ascertaining the area of the face may be more accurate and therefore more appropriate. The attenuation factor per unit area of the tail portion can be ascertained by dividing its attenuation factor by the area of the face of the tail portion.

Therefore, there is provided a leaf for a multi-leaf collimator including a leaf portion for delineating a beam of radiation, the leaf portion having first attenuation factor per unit area; and a tail portion having a second attenuation factor per unit area, the first attenuation factor per unit area being greater than the second attenuation factor per unit area.

Relative Linear Attenuation Coefficient

In some embodiments, the leaf portion has a greater attenuation factor per unit length (or per unit width or per unit area) because the leaf portion material has a greater linear attenuation coefficient than the tail portion material. In some embodiments, the leaf portion material has a higher atomic number than the tail portion material. For example, the first material may be Tungsten and the second material may be steel.

The linear attenuation coefficient describes the fraction of the radiation beam that is absorbed or scattered per unit thickness of the material. The linear attenuation coefficient is given by Equation 1.

$$\mu = -x^{-1} \ln\left(\frac{I}{I_0}\right) \quad (1)$$

Where: I is the intensity of radiation transmitted across a distance x, $I_0$ to is the initial intensity of the radiation, and $\mu$ is the linear attenuation coefficient.

The linear attenuation coefficients of some common materials at radiotherapy wavelengths can be found in the literature. However, the mass attenuation coefficient, which is density independent, is more readily available. Tables and graphs of the mass attenuation coefficients for all of the elements Z=1 to 92, and for compounds and mixtures of radiological interest are available at the National Institute for Standards and Technology website (https://www.nist.gov/pml/x-ray-mass-attenuation-coefficients). The tables on the NIST website cover energies of photons (x-ray, gamma ray, bremsstrahlung) from 1 keV to 20 MeV.

The mass attenuation coefficient can easily be converted to a linear attenuation coefficient, by multiplying it by the density of the material. That is, the linear attenuation coefficient (p), mass attenuation coefficient (M) and density (ρ) are related by Equation 2:

$$\mu = M\rho \quad (2)$$

Thus, the skilled person can ascertain whether or not the leaf portion material has a greater linear attenuation coefficient than that of the tail portion material by accessing published linear attenuation coefficient data or accessing published mass attenuation coefficient data and ascertaining (by measurement or reference) the material density.

The skilled person can also can readily ascertain the linear attenuation coefficient of the leaf portion material or tail portion material through routine testing procedures. The linear attenuation coefficient of a material is the number of e-foldings of the intensity that will be had as radiation energy passes through the material per unit depth of the material. This can be ascertained by a simple measurement of the intensity attenuation of a radiation beam by a block of the material, the radiation beam having the same properties as the beam emitted by the radiotherapy device for which the leaf is intended. The linear attenuation coefficient can then be calculated using Equation 1, using the thickness of the block x.

Thus, access to known mass attenuation coefficients and/or the ability to readily measure linear attenuation coefficients allows the skilled person to select appropriate materials for the leaf portion and tail portion and/or assess whether or not the leaf portion material has a greater attenuation coefficient than the tail portion material.

The purpose of the leaf portion is to delineate the radiation beam by heavily attenuating portions of it. Therefore, the material choice is limited to high atomic number materials, such as Tungsten.

The tail portion is not used to delineate the radiation beam. Its purpose is to push and pull the leaf portion and/or to accommodate other components which drive the leaf portion in its linear trajectories into and out of the path of the radiation beam.

The inventors have recognised that the material constraints for the tail portion can therefore be relaxed in comparison with those of the leaf portion due to the difference in function of the leaf portion and tail portion. The linear attenuation coefficient of the tail portion can be lower than that of the leaf portion because the tail portion does not need to function as a beam attenuator.

Although Tungsten is the preferred material for the leaf portion, it is not essential that the leaf portion material is Tungsten. The leaf portion material can be any material suitable for attenuating radiation from a radiotherapy device to an acceptable degree, namely a degree sufficient to reduce or prevent radiation damage to healthy tissue surrounding a target tissue. The second material is also not limited to the material in the above example. For example, the second material may include copper, aluminium, nickel, titanium or an alloy containing one or more of these materials or other suitable materials.

Relative Thickness

The leaf portion thickness is governed by the multi leaf collimator design including the size of the aperture between leaf banks and the required spatial aperture resolution among other considerations. The spacing between leaf portions of adjacent leaves must be minimal to prevent radiation leakage between the leaves and recesses in the thickness of the leaf portion are undesirable due to the need for the leaf portions to uniformly attenuate the radiation beam. However, the inventors have recognised that no such constraint on the thickness needs to be applied to the tail portion, because the tail portion does not perform the function of attenuating the beam.

Thus, in some embodiments, the leaf portion has a greater attenuation factor per unit length (or per unit width or per unit area) because it has a greater thickness (dimension between the faces in the fifth direction described herein) than that of the tail portion. The thickness may be a mean thickness or a minimum thickness.

Advantageously, if the thickness of the tail portion is less than the thickness of the leaf portion, the weight of the leaf is reduced.

Further advantageously, a comparatively lower thickness in a whole or a part of the tail portion allows more room for accommodating other components in the vicinity of the tail portion. For example, a reduced thickness in part or whole of the tail portion may allow more room for accommodating a leaf drive component (such as a leaf nut or leaf nut holder) associated therewith so that it does not impinge, or does not impinge too far, into the space adjacent the tail portion. This, in turn, reduces interference between adjacent leaves and their associated leaf drive components, or allows more freedom in design to mitigate interference, than if the tail portion and leaf portion thicknesses are identical to each other.

Relative Width

The leaf portion width determines the amount of material between the radiation source and the healthy tissue in the treated subject. The leaf portion width is therefore governed by the attenuation requirements of the multi leaf collimator. The width of the leaf portions must be sufficient to reduce the radiation intensity to an acceptable level. However, the inventors have recognised that no such constraint on the width needs to be applied to the tail portion, because the tail portion does not perform the function of attenuating the beam.

Thus, in some embodiments, the leaf portion has a greater attenuation factor per unit length because it has a greater width (dimension between the first and second edges in the fourth direction described herein) than that of the tail portion. The width may be a mean width or a minimum width.

Advantageously, if the width of the tail portion is less than the width of the leaf portion the weight of the leaf is reduced.

Further advantageously, a reduced width in a whole or a part of the tail portion allows more room for accommodating other components in the vicinity of the tail portion. This, in turn, reduces interference between adjacent leaves and their associated leaf drive components, or allows more freedom in design to mitigate interference, than if the tail portion and leaf portion widths are identical to each other.

Relative Ductility

Tungsten is difficult to machine owing to its very low ductility. The inventors have recognised that the difference in function between the leaf portion and tail portions means that the material constraints can be relaxed in the tail portion and this allows another material other than Tungsten to be used.

Thus, in some embodiments, the tail portion material is more ductile than the leaf portion material.

Advantageously, the tail portion has greater machinability than the leaf portion. Thus, the overall thickness of the tail portion can be controlled more easily during manufacture if a more ductile material is used. Accordingly, the cost and/or complexity of manufacture is reduced. In addition, the reduced ductility allows features to be machined into the tail portion with greater ease and at lower cost than if the tail portion is made from the same material as the leaf portion.

Recessed Parts in Tail Portion

In embodiments, the tail portion includes a recessed portion for receiving at least a part of a leaf actuator component. In some embodiments, the recessed portion is recessed from a face of the tail portion. In some embodiments, the tail portion includes a recessed portion having one or more of the following features: a slot for receiving a leaf actuator screw; a slot for receiving a leaf nut; a seat for receiving a leaf nut holder; a groove for receiving a leaf nut or leaf nut holder corresponding to an adjacent leaf.

Joining of the Leaf Portion and Tail Portion

The leaf portion and tail portion are each plate like in form and together they form a contiguous plate-like structure.

In some embodiments, the tail portion and the leaf portion are monolithic. For example, the whole leaf may be made from a single material (e.g. tungsten), but with a reduced thickness or reduced with in the tail portion.

In other embodiments, the tail portion is a separate piece of material which is coupled to the leaf portion. In this respect, the leaf portion and tail portion can be said to be modular.

In some embodiments, the leaf portion is separable from the tail portion. Advantageously, this allows replacement of the leaf portion or tail portion independently of each other. For example, if the tail portion is more ductile than the leaf portion, the tail portion may wear faster than the leaf portion. The cost of replacement of a worn tail portion is less than the cost of replacement of the whole leaf.

The coupling between the leaf portion and tail portion may be by adhesion or by fixing means, such as screws. In some embodiments, the coupling is via a joint between overlapping portions of the leaf portion and tail portion, for example via a lap joint or tongue-in-groove joint between the leaf portion and tail portion. Advantageously, this provides a strong and reliable bond between the leaf portion and tail portion which can withstand repeated shear stresses from the actuation of the leaf in its linear motion into and out of the path of the radiation beam.

Motor Mount Overview

In a multi leaf collimator, the leaf drive units are fixed to a mount that provides a base from which to push and pull the individual leaves. The mount is usually a plate which is placed behind the trailing (or tail) portion of the leaves, lying in a plane such that the axis of movement of the leaves is normal to that plane.

In known multi-leaf collimators, the mount includes a single mounting plate for receiving all leaf drive units corresponding to an entire leaf bank. If a leaf or leaf nut needs to be accessed (for example if it is damaged/worn and needs to be replaced) the entire mounting plate must be removed along with the entire leaf bank and the corresponding leaf drive units. Once this sub assembly of the multi-leaf collimator is removed, any leaves or leaf drive units can be maintained, repaired or replaced outside of the radiotherapy device. Thus, access to any one of the leaves and/or the various components of the leaf drive units involves removal of a large number of components from the multi-leaf collimator.

To address this problem, the mounting plate is split into sections, each section arranged to receive a subset of the leaf drive units associated with a leaf bank. Thus, only a subset of the leaves of any one leaf bank (and their corresponding leaf drive units) need to be removed and replaced. This provides quicker and easier access to any individual leaves and/or leaf drive units. Furthermore, fewer components of the multi-leaf collimator need to be removed/replaced during maintenance and repair, thus reducing radiotherapy device downtime.

Function of the Mount

In a fully assembled multi-leaf collimator, a plurality of leaf drive units for driving the leaves of one of the two leaf banks are mounted in a single mount, each leaf drive unit being mounted in a mounting hole in a mounting plate of the mount. The mount performs the functions of (i) providing a common reference point for the leaf drive units so that the individual leaves can be positioned reliably relative to each other; and (ii) aligning the leaf drive units with their respective coupling location at the tail of their corresponding leaf so that the angle of coupling between each leaf drive unit and leaf is consistent across the whole leaf bank.

The leaf drive units have at least one part that moves relative to another part thereof. Thus, the leaf drive unit can be said to have a first node (one part of the leaf drive unit) and a second node (another part of the leaf drive unit), wherein the second node is moved relative to the first node by operation of the leaf drive unit. For example, the first node may be a part of a leaf motor casing of the leaf drive unit and the second node may be a part of a leaf nut attached to a leaf, the leaf nut arranged to move linearly relative to the motor casing upon driving (i.e. rotation) of the leaf motor. Alternatively, the first node may be a part of the leaf motor casing and the second node may be a part of a leaf actuator screw attached to the leaf, the leaf actuator screw arranged to move linearly relative to the leaf motor casing upon rotation of the leaf motor.

The leaf drive units are mounted so that relative linear and rotational movement between a first node of each leaf drive unit and the mount is prevented. Thus, the mount serves to provide an anchor for the first node of the leaf drive units so that the leaf drive units engender relative motion between second node the mount, which in turn leads to motion of the individual leaves relative to the mount. The mount itself may be either static or moveable relative to a base of the multi-leaf collimator. Thus, the mount provides an anchor point for reliable relative positioning of the individual leaves, which in turn allows reliable and accurate shaping and positioning of the beam shaping aperture.

Traditional Mounts

In known mounts, the mounting plate (the part of the mount in which the leaf drive units are mounted) is provided as one integrated component. That is, the mounting plate cannot be disassembled to form separate parts having mounting holes for receiving the leaf drive units. Thus, all leaf drive units are coupled to the same individual component of the mount. In other words, known mounts include a single mounting plate for receiving all leaf drive units of one leaf bank of the multi-leaf collimator.

Removal, repair or replacement of any of the leaves or leaf drive unit components can be carried out in situ in the multi-leaf collimator. This can be difficult due to the lack of space available for accessing the various components. If a mount with a single traditional mounting plate is used, the time needed for repair can be relatively lengthy due to the density of the motors. Typically, all of the motor power connectors would have to be disconnected from the control board, which is a risk to reliability. Alternatively, the entire leaf bank, leaf drive unit array and mounting plate can be removed as one along with the mounting plate before the leaf drive unit components (e.g. the leaf actuator screws, or leadscrews) are decoupled from their corresponding leaves. Thus, removal of a large number of other components must be carried out even if only a single leaf drive unit or leaf needs repair, maintenance or replacement.

Mount with Separable Mounting Plates

Embodiments include a mount for an array of leaf drive units corresponding to a single leaf bank of a multi-leaf collimator, the mount comprising: a plurality of separable mounting plates, each mounting plate comprising an array of mounting holes, each mounting hole arranged to receive a respective one of the leaf drive units.

The provision of a mount having separable mounting plates allows removal of a subset of leaf drive units from their installed position in the multi-leaf collimator. That is, a subset of the leaves of one leaf bank together with their corresponding leaf drive units can be removed without disturbing the other leaves and/or leaf drive units of the same leaf bank. Servicing of the individual leaf drive units and/or their corresponding leaves is easier because the fewer the number of leaves and leaf drive units in the removed sub assembly of the multi-leaf collimator, the easier it is to manoeuvre the sub assembly and access the leaf and/or leaf drive unit in need of servicing. Radiotherapy device downtime is reduced as a result.

Coupling Between Adjacent Mounting Plates

In a fully assembled multi-leaf collimator, the separable mounting plates are arranged in the same plane and are removably coupled together. The mounting plates may be coupled together by a releasable coupling member between adjacent mounting plates, or by a common frame, mount or bracket coupled to all mounting plates.

Alternatively, or in addition, the mounting plates may include mutually interlocking parts. That is, each mounting plate and its adjacent mounting plate have interlocking parts. Advantageously, this improves the accuracy, reliability and ease of alignment of the mounting plates.

In embodiments, a first mounting plate is coupled to a second mounting plate adjacent the first mounting plate via the selective interlocking of at least a part of the first mounting plate with at least a part of the second mounting plate. The interlocking is selective in that the second mounting plate can be moved from a position in which the at least a part of the second mounting plate and at least a part of the first mounting plate are interlocked, to a position in which there is no interlocking between the second mounting plate and the first mounting plate. The interlocking limits the movement of the second mounting plate linearly in at least one pair of two opposing directions and or rotationally. Advantageously, the interlocking assists reliable positioning of the mounting plates and therefore the leaf drive units coupled thereto during repair/replacement so that the complexity and cost of repair/replacement is reduced.

Thus, it may be understood that the mounting plate is movable from a first position, in which the second mounting plate is interlocked with the first mounting plate, along an axis to a second position in which the second mounting plate is free from the first mounting plate. In embodiments, the axis may be the first axis described herein (i.e. parallel to the longitudinal direction of the leaves). Advantageously, the second mounting plate can be removed more easily along with the leaf drive units mounted thereto and the corresponding leaves while causing minimal disturbance to the leaf drive units mounted to the first mounting plate and the corresponding leaves attached thereto.

In embodiments, the interlocking parts of the first mounting plate and second mounting plate include a recessed structure on one of the first mounting plate and second mounting plate and a corresponding protruding structure on the other of the first mounting plate and second mounting plate for insertion into the recessed structure. Advantageously, this provides a simple mechanism for preventing movement of the first mounting plate relative to the second mounting plate in one axis (perpendicularly from either side of the protruding or recessed structure) while allowing movement in an axis perpendicular to this (e.g. into/out of the recessed structure).

In embodiments, the recessed structure or protruding structure is elongate, thus allowing movement in an axis perpendicular to these two axes (i.e. parallel to the lengthwise direction of the recessed structure or protruding structure). For example, the recessed structure may be a slot or groove on one of the first mounting plate and second mounting plate, and the protruding structure may be a structure on the other of the first mounting plate and second mounting plate corresponding to the slot or groove for engaging the slot or groove.

Alternatively, or in addition, the protruding structure includes a rib or spine on one of the first mounting plate and second mounting plate, and the recessed structure is a structure on the other of the first mounting plate and second mounting plate for engaging the rib or spine.

In embodiments, the interlocking means prevent movement of the first mounting plate relative to the second mounting plate in the plane of the plates themselves, but allow movement therebetween out of this plane for ease of removal of either mounting plate during servicing. A catch, frame, holder or support may be provided to selectively prevent relative movement between the first mounting plate and second mounting plate along the first axis (i.e. in the direction of travel of the leaves). Thus, all relative movement between the first mounting plate and second mounting plate can be prevented during operation of the multi-leaf collimator.

Whereas for servicing, one mounting plate can be slid out from its interlocked position adjacent another mounting plate to a position in which it is free from the adjacent mounting plate and can be replaced simply and accurately back to the same position after servicing.

Advantageously, the interlocking allows simpler removal and replacement of the first and second mounting plates from each other while providing reliable and accurate positioning of the first and second mounting plates relative to each other. It is important that the mounting plates are aligned accurately because this affects how the leaf drive units are aligned with the leaves, which in turn affects the accuracy and reliability of the multi-leaf collimator in use.

Mounting Holes

The mounting holes are provided in a two-dimensional array in each mounting plate. The array provides appropriate alignment between the leaf drive units and the part of the corresponding individual leaves to which they are coupled.

Typically, the leaves are arranged so that the point at which the leaf drive unit is connected thereto is staggered between adjacent leaves. As the leaf drive units can have a maximum width which is greater than the maximum width of each individual leaves, this staggering is necessary to ensure that two adjacent leaf drive units do not interfere with one another. Therefore, the mounting holes in the array are arranged in a staggered fashion such that a column of mounting holes is provided with a pitch in the vertical direction (i.e. the second axis defined herein) of the order of the maximum diameter of the leaf drive units and a pitch in the horizontal direction (i.e. the third axis defined herein) of the order of the maximum thickness of the leaves.

Thus, the two-dimensional array is arranged into a grid comprising rows and columns. The rows extend in a direction across the leaf bank (i.e. substantially parallel to the third axis defined herein) and the columns extend in a direction lying across this direction and perpendicular to the direction of travel of the leaves. The staggering of mounting holes in each column means that a centreline common to the mounting holes of a column is oblique to a centreline common to the mounting holes of a row. Put more simply, the columns are not perpendicular to the rows.

That is, in embodiments, the centre points of mounting holes in the array are aligned in columns extending in a first direction and in rows extending in a second direction lying across the first direction, wherein the first direction is oblique to the second direction.

Advantageously, the leaf drive unit array, when in the configuration described above, reduces or minimises wasted space and the multi-leaf collimator can be more compact as a result. A more compact multi-leaf collimator can be more easily housed and manipulated in a radiotherapy device.

So that the columns of mounting holes across the entire leaf bank can be uniformly spaced, the profile of the mounting plates are configured to allow continuity of the pattern of holes in the array from one mounting plate to the adjacent mounting plate. That is, a cross-section of at least one of the mounting plates in the plane of the mounting plates (i.e. the third plane defined herein) is shaped so that a first edge thereof and a second edge thereof opposite to the first edge are substantially parallel to a centreline common to a column of mounting holes. In this way, the mounting holes of a column adjacent to the first edge or the second edge are uniformly spaced from the edge and a distance from the edge to a centreline common to the mounting holes is uniform.

More generally, the centre points of mounting holes in the array are aligned in columns extending in a first direction, and at least one edge of each of the mounting plates is parallel to the first direction. In embodiments, the centre points of mounting holes in the array are aligned in columns extending in a first direction and in rows extending in a second direction lying across the first direction, wherein the first direction is oblique to the second direction, a first edge each of the mounting plates is parallel to the first direction, and a second edge of each of the mounting plates is parallel to the second direction.

Alternatively, or in addition, the plurality of mounting plates includes a first mounting plate and a second mounting plate arranged adjacent the first mounting plate. The mounting hole centre points in the first mounting plate are arranged in a first series of columns and the mounting hole centre points in the second mounting plate are arranged in a second series of columns. Adjacent columns in the first and second series of columns have a first spacing therebetween. A column in the first series of columns closest to the second mounting plate and the column in the second series of columns closest to the first mounting plate have a second spacing therebetween, the second spacing being equal to the first spacing.

Advantageously, the mounting plates do not disrupt the regular spacing between columns from one plate to the next in the overall array.

In embodiments, the distance between the centreline common to the mounting holes in the column adjacent the first edge of the mounting plate is equal to half the distance between the centrelines of adjacent columns of the mounting plate. If the same is true for the distance between the second edge and the centreline of the column adjacent the second edge, the mounting plates can be interchangeable, because any mounting plate of this design can be used adjacent another mounting plate of the same design while maintaining the regularity of spacing between columns across the whole array.

Typically, six mounting holes are provided per column in the array, but this number can be greater than or less than six depending on how the connection points between the leaves and the leaf drive units are staggered in the leaf bank. In embodiments, the spacing between mounting holes in one column and/or one row of the array is uniform and is sufficient to allow adequate spacing between adjacent leaf drive units to allow them to operate without interfering with one another.

Mounting of the Leaf Drive Units into the Mounting Plates

The mounting holes in the mounting plates are each arranged to receive a part of a leaf drive unit. Typically, the part received is a part of the leaf motor casing as this performs well as the aforementioned first node of the leaf drive unit. The other components of the leaf drive unit (i.e. the internal parts of the leaf motor, the leaf actuator screw and/or the nut associated therewith) are then free to move relative to the mounting plate.

Each mounting hole is typically a through hole in the mounting plate passing between the faces of the mounting plate. If a through hole is used, a bayonet type fitting between the mounting plate and each leaf drive unit can be adopted. In this type of fitting, the leaf actuator screw is fed through the mounting hole from one side of the mounting plate to the other side until a part of the leaf motor casing engages with the mounting plate. In this configuration, the leaf motors are located on one face of the mounting plate opposite the face closest to the leaves. Thus, the leaf drive units can be removed from the mounting plates by pulling them back through the mounting holes in a direction away from the leaves (i.e. along the first axis in the second direction described herein). Removal of the leaf drive units in this way allows removal and replacement of a leaf drive unit without removal of the entire leaf bank or even without removal of a large subset of the leaf drive units of one leaf bank as is made possible by the use of the separable mounting plates as described above.

Retainer

Once the leaf drive units are inserted into the mounting holes, respective retainers fixed to or integral with the mounting plate fix each leaf drive unit to the mounting plate. In the case of a mount having separable mounting plates, the mount includes a plurality of retainers attached to the mounting plates, each retainer arranged to rigidly couple a respective leaf drive unit to one of the mounting plates.

The main function of the retainer is to prevent linear movement of the first node of the leaf drive unit relative to the mounting plate so that the leaf drive unit cannot be withdrawn from the mounting hole. The retainer may also prevent rotational movement of the first node of the leaf drive unit, although this function can also be achieved by interlocking parts on the leaf drive unit and mounting plate without the use of the retainer.

In traditional mounts, the retainer is a screw mounted in the mounting plate adjacent a respective mounting hole. A head of the screw is arranged to engage with a lip or flange on the leaf drive unit (e.g. on the leaf motor casing) to urge a part of the leaf drive unit onto the face of the mounting plate to hold it in position.

The screw must be fully removed so that the screw head is no longer an obstacle which prevents the leaf drive unit from being completely withdrawn from the mounting hole. Once the leaf drive unit is replaced into the mounting hole, the screw can be reinserted into its hole on the mounting plate and tightened to reengage the leaf drive unit.

The problem with this arrangement is that the screw must be completely removed from the mounting plate before the leaf drive unit can be removed or replaced. The screw can easily be dropped and is difficult to remove and replace itself, which increases service time and cost and increases radiotherapy device downtime.

Quick Release Retainer

Embodiments provide a quick-release attachment between the motor and the mounting plate. A retainer (e.g. a screw) in the mounting plate engages a flange (or lip) on the motor casing to couple the motor to the mounting plate.

To remove the motor, the screw is slightly loosened, and the motor casing is rotated so that the flange disengages from the screw (a relief in the flange aligns with the screw head) and the motor is decoupled from the mounting plate and can be removed without complete removal of the screw.

In embodiments, the retainer includes a threaded portion arranged to engage with a threaded hole in the mounting plate, and a retaining portion including a retaining face of larger outer diameter than the threaded portion. The axis of the threaded portion lies perpendicular to the plane of the retaining face. The retaining face may be an annular face. If the retainer is a screw or bolt, the retaining portion is the screw head or bolt head itself and the retaining face is the underside of the screw head or bolt head. In use, the retaining face is the part of the retainer that engages the leaf drive unit and urges it against the face of the mounting plate.

More generally, each retainer is positioned adjacent to a respective one of the mounting holes and includes: a head including a retaining face arranged to face the mounting plate, a shaft extending from the head and arranged to rotatably engage with the mounting plate such that rotation of the retainer about the axis of the shaft moves the retaining face closer to or further from the mounting plate.

The part of the leaf drive unit which is engaged by the retainer is preferably the leaf motor casing. The leaf motor casing this provides the ideal 'first node' referred to herein, because it is designed to be static while other parts of the leaf drive unit connected to the leaf motor rotate relative to it. However, any other part of the leaf drive unit which fulfils these criteria can be used to provide the first node.

In embodiments, the leaf motor casing includes an engaging member arranged to provide a surface which engages with the retaining face of the retainer so that the retainer urges the leaf motor casing against the mounting plate. That is, engaging member may be a flange or lip. The engaging member may be the mounting flange described in the detailed description. The engaging member is any part of the leaf motor casing which has a larger diameter or width than the diameter of the mounting hole and a thickness suitable for positioning between the retaining face of the retainer and the face of the mounting plate.

The engaging member has a recess provided therein such that upon rotation of the leaf motor casing relative to the mounting plate, the recess can overlap with the retaining face of the retainer to allow removal of the leaf motor casing from the mounting plate without removal of the retainer from the mounting plate. That is, the leaf motor casing is rotatable between a first position in which the flange is engaged with the retaining face to a second position in which the recess overlaps with the retaining face and the leaf drive unit can be removed entirely from the mounting hole without removing the retainer from the mounting plate.

Advantageously, the retainer does not need to be removed from the mounting plate for removal or replacement of the leaf drive unit.

More generally, each leaf drive unit includes: a motor comprising a casing including an engaging member, wherein at a first rotational position of the casing the engaging member engages the retainer to couple the casing to the mounting plate; and at a second rotational position of the casing the engaging member is disengaged from the retainer.

Embodiments provide a drive arrangement for a multi-leaf collimator comprising: a mounting plate for mounting a leaf drive unit; a retainer attached to the mounting plate; a motor configured to actuate a leaf of the multi-leaf collimator, the motor comprising a casing including an engaging member. At a first rotational position of the casing the engaging member engages the retainer to couple the casing to the mounting plate. At a second rotational position of the casing the engaging member is disengaged from the retainer.

In embodiments, the recess has a curved shape so as to match the shape of the overlapping part of the retainer head. However, it is not essential that the recess has this shape. The recess can have any shape and size so long as it accommodates the overlapping part of the retainer head so as to allow the leaf motor casing to move clear of the retainer head when the leaf motor casing is rotated to the second position.

In embodiments, each mounting hole has two retainers adjacent thereto and spaced apart by 180 degrees around the mounting hole.

In embodiments, retainers positioned between rows or between columns are arranged substantially equidistant between mounting holes such that they can retain two leaf drive units mounted in adjacent mounting holes. That is, each retainer engages the engaging member of more than one motor casing. In some embodiments, a single retainer may retain three, or even four, leaf drive units when positioned substantially equidistant between the corresponding number of mounting holes.

The leaf motor casing has a locating member arranged around the circumference thereof to engage an outer circumferential surface of the retaining head of the retainer. The locating member is arranged such that when the leaf drive unit is fully inserted into the mounting hole and rotated in the direction from the first position toward the second position, the locating member prevents any further rotation of the leaf drive unit in this direction once the leaf drive unit arrives at the second position.

More generally, the casing includes a locating member arranged to engage with the retainer when the motor casing is at the second rotational position so as to prevent further rotation of the motor casing once the motor casing has reached the second position.

Advantageously, this allows ease of locating the second position without clear sight of the leaf motor casing.

This aids in the smooth and reliable removal of the leaf drive unit from the mounting hole and thus reduces servicing time.

The locating member may be a protrusion from a part of the leaf motor casing, for example the ridge as described in embodiments in the detailed description herein. In embodiments, the leaf motor casing includes a plurality of locating members corresponding to the number of retainers associated with the mounting hole, each locating member arranged to engage with the retainer head at the second rotational position.

Further Embodiments

Embodiments include a leaf assembly including the leaf nut and/or leaf nut holder having any of the structures defined herein.

Embodiments also include a multi leaf collimator having said leaf assembly.

Embodiments also include a radiotherapy device having said multi leaf collimator.

Embodiments include a leaf bank including leaves having any of the structures defined herein.

Embodiments also include a multi leaf collimator having said leaf bank and/or a radiotherapy device having said multi leaf collimator.

BRIEF DESCRIPTION OF THE DRAWINGS

Specific embodiments are described below by way of example only and with reference to the accompanying drawings in which:

FIG. 1 shows a partially assembled multi leaf collimator;

FIGS. 2c, 2d, 2e and 2f each show a close-up view of locking joint between a tail portion and leaf portion of a leaf according to an embodiment;

FIG. 3a shows a close up isometric view of a leaf nut according to an embodiment installed in the tail portion of a leaf, FIG. 3a also shows the edge of the tail portion of a leaf according to an embodiment;

FIG. 3b shows a cross section of the leaf nut and leaf, including the tail portion of the leaf, shown in FIG. 3a;

FIG. 4b also shows an isometric view of a face of the tail portion in the vicinity of a seat in the tail portion;

DETAILED DESCRIPTION OF THE DRAWINGS

MLC Assembly

Defining a Useful Co-Ordinates Convention

Figure 2A:
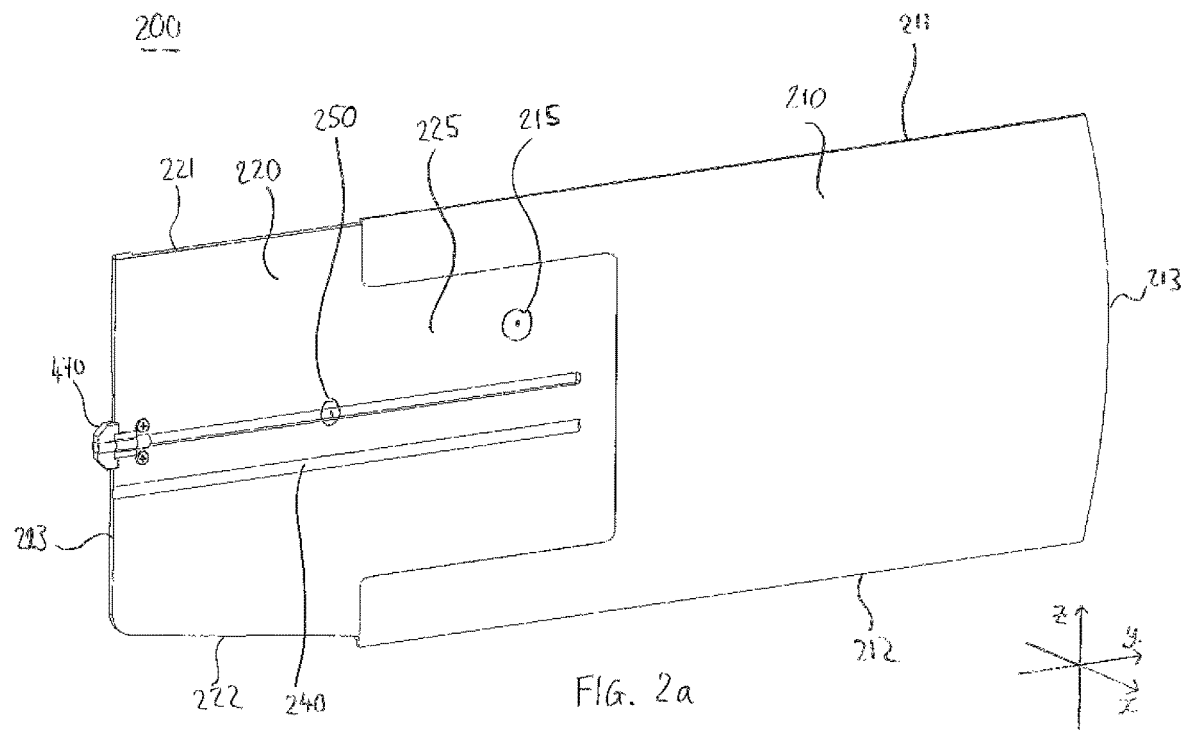
FIGS. 2a and 2b show isometric views of a leaf including a leaf nut and leaf nut holder according to an embodiment.

For ease of description, a cartesian co-ordinates system is defined in the Figures by a mutually perpendicular first axis (y), second axis (z) and third axis (x). The first axis defines a first direction (+y) and a second direction (−y) opposite to the first direction. The second axis defines a third direction (+z) perpendicular to the first direction and a fourth direction (−z) opposite to the third direction. The third axis defines a fifth direction (+x) perpendicular to both the first direction and the third direction and a sixth direction (−x) opposite to the fifth direction. The first and second axes define a first plane (yz), the first and third axes define a second plane (xy) perpendicular to the first plane, and the second and third axes define a third plane (xz) perpendicular to the first and second planes. The first and third directions define the first plane (yz), the first and fifth directions define the second plane (xy) perpendicular to the first plane, and the third and fifth directions define the third plane (xz) perpendicular to the first and second planes. This co-ordinates system and convention is used consistently throughout the Figures.

FIG. 1 shows a partially assembled multi-leaf collimator 100 comprising a leaf bank 20, a first and second leaf guide 301, 302, a leaf drive array 40 and a leaf drive mount 50.

Figure 9:
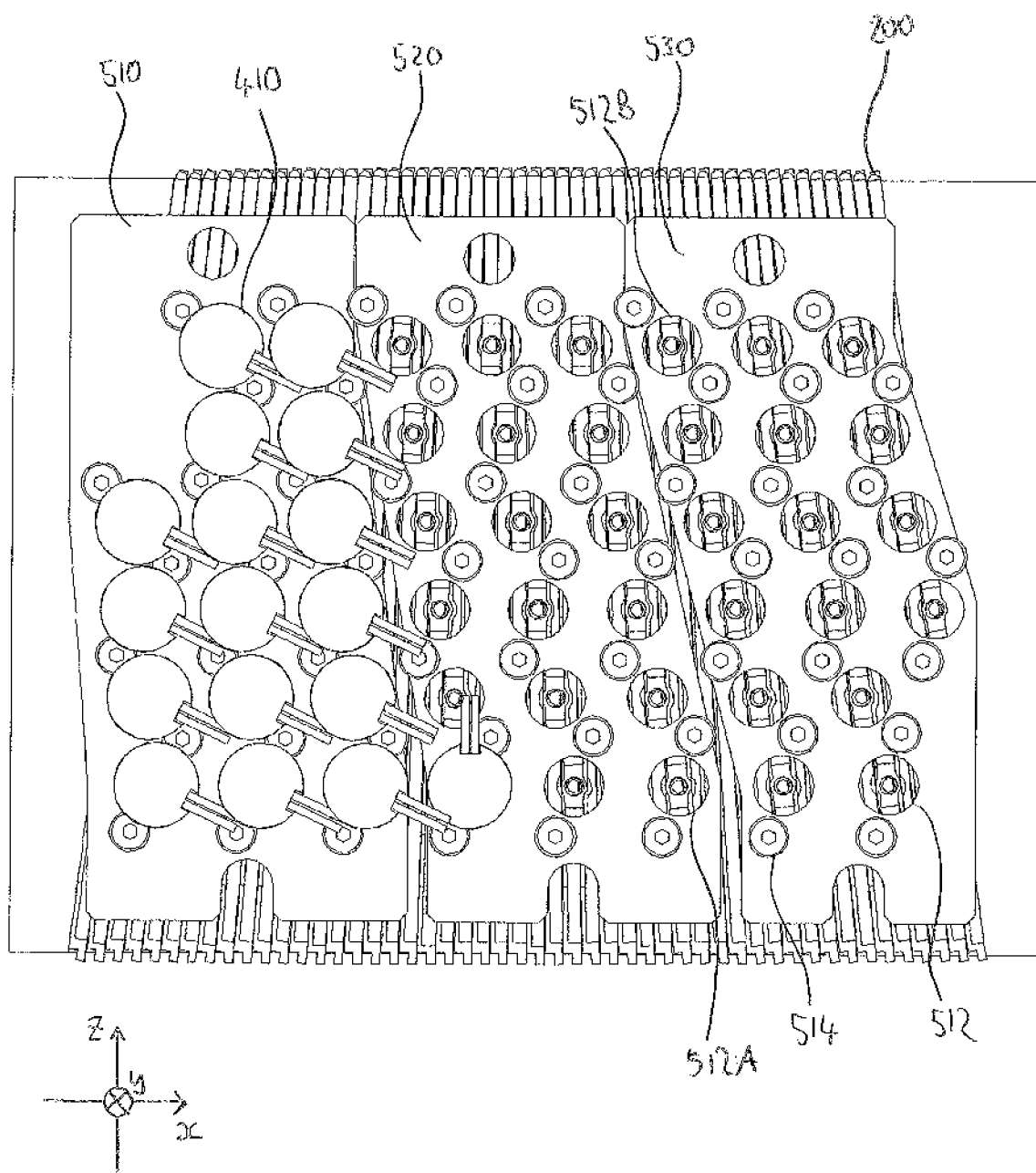
FIG. 9 is an elevation view of the mount.

The leaf bank 20 includes an array of leaves 200 arranged side by side so that a face of one leaf is in contact with a face of an adjacent leaf. The leaves 200 are arranged substantially parallel to each other but a gradient in thickness in the first direction from a first edge of each leaf 200 to a second edge opposite the first edge causes the leaf bank 20 to adopt a trapezoidal cross section in the third plane as shown in FIG. 9. Thus, the plane of a leaf 200 positioned in the middle of the leaf bank 20 is arranged to be substantially parallel to the first plane (yz), but the planes of the other leaves either side of that leaf 200 form a progressively greater angle with the first plane (yz) with distance in the fifth and sixth directions from the centre of the leaf bank 20. The leaves 200 are arranged to move relative to each other in the first and second directions. The leaves 200 are described in more detail below.

The leaf drive array 40 includes a plurality of leaf drive units 400. Each leaf drive unit 400 includes a leaf motor 410, a leaf actuator screw 430, a leaf nut 450 and a leaf nut holder 470. The leaf actuator screw 430 is coupled to the leaf motor 410 and is arranged so that its axis is parallel to the first direction. The leaf motor 410 is arranged to rotate the leaf actuator screw 430 about its axis (i.e. clockwise and anti-clockwise around the first direction). The leaf nut 450 is held in position in a leaf actuator screw slot 250 in the leaf 200 by a leaf nut holder 470 fixed to the leaf 200. The leaf nut 450 is held by the leaf nut holder 470 to be static relative to the leaf 200, with the exception that a small amount of relative linear motion between the leaf nut 450 and the leaf 200 is allowed in the third and fourth directions. The leaf nut 450 contains features which interact with the leaf 200 to keep the leaf nut 450 rotationally static relative to the leaf 200. The leaf nut 450 is arranged to receive the leaf actuator screw 430 and to guide it into the leaf actuator screw slot 250. The rotational motion of the leaf actuator screw 430 translates into linear motion of the leaf nut 450, and hence the leaf 200, relative to the leaf actuator screw 430.

The leaf drive units 400 are staggered in the first direction so that the leaf nut holder 470 of any one leaf does not interfere with the leaf nut holders 470 of the leaves 200 immediately adjacent to it on either side. The leaves 200 also contain grooves to accommodate the portions of the leaf nut holders 470 of adjacent leaves 200 which are proud from the face of the leaf 200. The leaf motor 410, leaf nut 450, leaf nut holder 470 and the grooves in the leaves are described in more detail below.

The leaf drive mount 50 includes three separate mounting plates 510, 520, 530 arranged in a plane parallel to the third plane (xz). The leaf drive mount includes mounting holes 512 therein for receiving the leaf motors 410 and mounting screws 514 for securing the leaf motors 410 to the mounting plates 510, 520, 530. The leaf drive mount 50 and each of its components are described in more detail below.

The first and second leaf guide 301, 302 each comprise a rectangular frame for guiding and supporting the leaves 200 in their linear motion in the first and second directions respectively into and out of the path of the radiation beam.

A complete multi leaf collimator assembly further includes a second, opposing arrangement including leaf bank, leaf guides, leaf drive array and leaf drive mount which are arranged to substantially mirror the assembly described above relative to a plane parallel to the third plane (xz) and aligned with the centre of the axis of the radiation beam.

In use, the leaf drive arrays drive the leaves 200 of their respective leaf banks 200 to move into and out of the path of a radiation beam passing in the fourth direction through an aperture formed between the leading edges of the leaves 200 of one leaf bank 20 and those of the leaves 200 of the opposing leaf bank 20. The leaves 200 of each leaf bank 20 are moveable independently of each other, which enables the shape of the aperture to be changed according to treatment requirements. The aperture acts as a beam shaper by blocking portions the radiation beam to redefine its cross-sectional shape in the second plane (yz). That is, the radiation beam having passed through the aperture takes on the cross-sectional shape of the aperture in the second plane (yz).

Composite Leaf

The leaf 200 can be formed from a monolithic plate comprising a single material. Alternatively, the leaf 200 can be a composite leaf comprising two plates of different materials joined together such that the plates are coplanar.

Introduction to Leaf Portion and Tail Portion

Figure 2B:
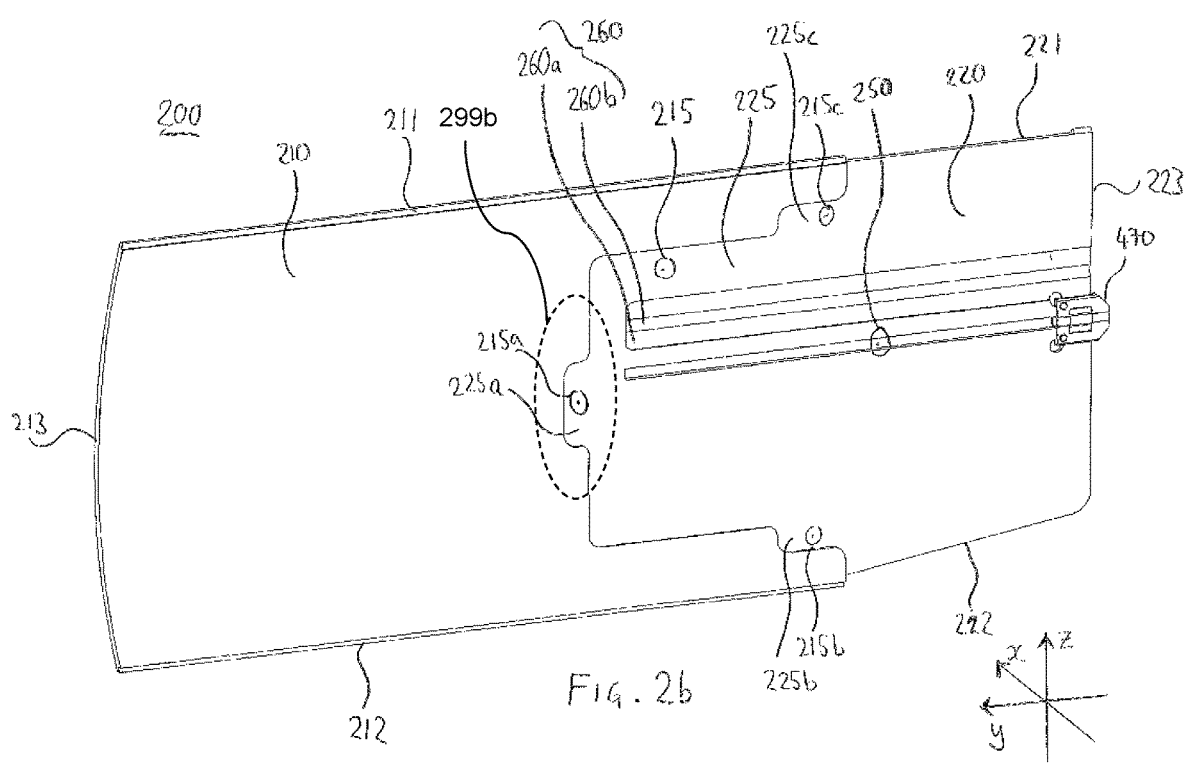

FIGS. 2a and 2b each show a different isometric view of such a composite leaf 200. The composite leaf includes a leaf portion 210 and a tail portion 220. The composite leaf 200 is formed as a flat, substantially rectangular-shaped plate, notwithstanding the shape of some of the edges of the composite leaf 200 described below. The leaf portion 210 and the tail portion 220 form a first and second area of the plate, respectively. The average thickness of the composite leaf 200 is small relative to its width and length. The central plane of the tail portion 220 is coplanar with that of the leaf portion 210.

The leaf portion 210 is made from a high atomic numbered material, e.g. tungsten, so that it is substantially opaque to the radiation. The purpose of the leaf portion 210 is to block a portion of the radiation beam. The leaf portions 210 of all leaves 200 in the leaf bank 20 act together to form the edge of the aperture for shaping the radiation beam. In contrast, the tail portion 220 plays no part in attenuating or blocking parts of the radiation beam. The tail portion 220 operates to push and pull the leaf portion 210 into and out of the path of the radiation beam. Thus, functionally, the tail portion can be thought of as part of (e.g. an extension of) the leaf drive mechanism. As such, the tail portion does not need to be made of a high atomic number material and can be made from a thinner plate than the leaf portion. Furthermore, the tail portion can be manufactured from a material which is lighter and/or easier to machine than tungsten. Greater ease of machining allows functional features to be added to the tail portion 220 (e.g. the features described below) which would be much more difficult, time intensive or cost intensive to machine into the high atomic numbered material of the leaf portion 210.

Relative Alignment of the Composite Leaf in the Co-Ordinates System

The plane of the composite leaf 200 is in the first plane (yz) when in situ in the multi leaf collimator, with the long edges and short edges of the rectangular shape of the composite leaf 200 being aligned in the first and third directions, respectively. The composite leaf 200, and therefore the tail portion 220 and the leaf portion 210, each have a first face and a second face on the opposite side to the first face, and both faces lie substantially parallel to the first plane (yz). FIG. 2a shows an isometric view from one side of the leaf 200 including the first face and FIG. 2b shows an isometric view from the other side of the leaf 200 including the second face.

Shapes of the Leaf Portion and Tail Portion

The first area comprises a first substantially rectangular area having a U-shaped recess 215 recessed from one side thereof, the recess 215 extending in the first direction into the first substantially rectangular area. The second area comprises a second substantially rectangular area defining a main body of the tail portion 220 and a tongue 225 protruding in the first direction from one edge of the main body. The tongue 225 has a shape and dimensions which correspond to those of the recess 215 of the first area. The tongue 225 is received in the recess 215 when the leaf portion 210 and the tail portion 220 are joined. The substantially rectangular shape of the composite leaf 200 is formed by the outline of the composite shape defined by the first area and second area.

The leaf portion 210 has a first edge 211 aligned with the first direction, a second edge 212 opposite the first edge 211 and aligned with the first direction, and a third edge 213 opposite the recess 215 and aligned with the third direction. The first edge 211 is part of the top edge of the composite leaf 200 when the leaf 200 is in situ in the multi-leaf collimator 100 and the radiation beam is directed vertically downward (i.e. in the fourth direction). The third edge 213 opposite the recess 215 is the leading edge of the leaf portion 210 and is the part of the leaf portion 210 which is closest to the axis of the radiation beam in use. The leading edge is slightly convex in the third direction (i.e. curved outwardly from the main part of the leaf portion 210 in the first plane) and has a radius of curvature which is greater than the length of the leaf 200 in the first direction.

The tail portion 220 has a first edge 221 aligned with the first direction, a second edge 222 opposite the first edge and oblique to the first direction and a third edge 223 opposite the tongue 225 and aligned with the third direction. The third edge 223 is the trailing edge of the composite leaf 200, meaning it is the furthest edge from the axis of the radiation beam in use. The first edge is part of the top edge of the composite leaf 200 when the leaf 200 is in situ in the multi-leaf collimator 100 in use when the radiation beam is directed vertically downward.

Recess in Tail Portion for Allowing Clearance for a Leaf Drive Component

The leaf drive components for driving an individual leaf may include the leaf nut, leaf nut holder and leaf actuator screw. The thickness (i.e. dimension in the direction normal to the plane of the leaf) or diameter of the leaf drive components affects both their suitability to fit in the confined spaces behind the leaves and their stability in operation. In general, the greater the thickness or diameter, the more stable the leaf drive component is in operation but the more difficult it is to accommodate multiple leaf drive components in close proximity to each other and the leaves. Thus, there is a trade-off between the size of the leaf drive components and their stability.

In general terms, the present disclosure provides a leaf for a multi-leaf collimator, the leaf comprising a leaf portion and a tail portion, the tail portion including a longitudinally extending recess for accommodating (or receiving) at least a portion of a leaf drive component. The leaf drive component is associated with (that is, it may be arranged to drive) the leaf itself or an adjacent leaf. This may prevent the leaf drive component from interfering with the motion of the leaf itself or interfering with the motion of an adjacent leaf and/or adjacent leaf drive component. The thickness or diameter of the leaf drive component can therefore be greater than the thickness of the individual leaves (or the pitch between adjacent leaves where there is a clearance between the leaves). Larger leaf drive components can improve the stability of the leaf drive mechanism and hence the maximum speed of the leaves can be increased.

The leaf is for use in a multi-leaf collimator having a plurality of leaves and a plurality of leaf drive components, wherein each leaf drive component is configured to drive a respective leaf.

There is also provided in a multi-leaf collimator having a plurality of leaves and a plurality of leaf drive components, wherein each leaf drive component is configured to drive a respective leaf. At least one of the leaves comprises a leaf portion and a tail portion, the tail portion including a longitudinally extending recess for accommodating a leaf drive component associated with the leaf itself or an adjacent leaf. In embodiments, the leaf drive components are identical so that the longitudinally extending recess is identical in form in each leaf. The leaf drive components may be staggered in the vertical (z) direction. In this case, if the longitudinally extending recess is arranged to accommodate a leaf drive component of an adjacent leaf, the position of the longitudinally extending recess in each leaf will also be staggered in the vertical (z) direction. Thus, the longitudinally extending recesses may be identical in form but differ in its position on or in the leaf depending on the position of the leaf within the leaf bank.

Several examples of a longitudinally extending recess are described below with reference to FIGS. 2a, 2b, 3a, 3b, 4a and 4b.

Leaf Actuator Screw Slot 250

The tail portion 220 has a through slot therein extending in the first direction, the through slot may be described as a leaf actuator screw slot 250. The leaf actuator screw slot 250 extends from the third edge 223 of the tail portion 220 towards a terminal end of the tongue 225. The leaf actuator screw slot 250 extends in both the main body of the tail portion 220 and the tongue 225 and terminates before the end of the tongue 225.

As shown in FIG. 3a, which is described in more detail below, the leaf actuator screw slot 250 includes a first slot section 250a proximal to the third edge 223 and a second slot section 250b distal from the third edge 223. The second slot section 250b is immediately adjacent and contiguous with the first slot section 250a. The first slot section 250a has a width in the third direction fractionally larger than that of the second slot section 250b. The second slot section 250b is several times longer in the first direction than the first slot section 250a.

In embodiments, a slot in the leaf (e.g. the leaf actuator screw slot 250 described above) is arranged to provide clearance to accommodate misalignments between the leaf and the leaf actuator screw. That is, the slot is wider than the diameter of the leaf actuator screw so that the leave actuator screw can move up and down (i.e. in the plane of the leaf) within the slot. In other words, the slot for receiving the leaf actuator screw provides a clearance either side of the leaf actuator screw in the plane of the leaf.

The clearance may be matched to the permitted movement of the leaf nut in the third direction and fourth direction (+/−z) in the plane of the leaf (as described herein) so that the resulting position of the leaf actuator screw upon movement of the leaf nut between its extremities in the third direction and fourth direction (+/−z) is accommodated by the clearance provided by the slot. This can allow a greater range of movement of the leaf nut and leaf actuator screw relative to the leaf. Therefore, misalignments between the leaf drive components and the leaf resulting from misalignments between the leaf motor and the leaf can be accommodated to a greater degree. This can improve the stability of the leaf drive mechanism and prevent wear on the leaf nut, the leaf actuator screw and the leaf motor, thus prolonging the service life of these components.

First Groove

A first groove 240 extends from the third edge 223 of the tail portion 220 toward a terminal end of the tongue 225. The first groove 240 is located along the first face of the tail portion 220 parallel to the leaf actuator screw slot 250. The first groove 240 is offset from the leaf actuator screw slot 250 in the fourth direction. The first groove 240 and the leaf actuator screw slot 250 are substantially the same length. The first groove 240 has a cross-sectional shape the third plane (xz) of a minor segment of a circle to accommodate convex parts of the leaf nut 450 and leaf nut holder 470 which are proud from the face of an adjacent leaf 200. The composite groove 260 is shown in closer detail in FIG. 4b.

Seat FIG. 2b shows an isometric view of the second face of the composite leaf 200. FIG. 3a shows a close up isometric view of the second face of the tail portion 220 in the region of the first slot section 250a.

The leaf actuator screw slot 250 is a through slot in that it passes through the whole thickness of the tail portion 220 from the first face to the second face. The first slot section 250a lies in the centre of a seat 255 recessed into the second face of the tail portion 220. The seat 255 has a cross section in the shape of a high-aspect-ratio (third direction length: fifth direction width) rectangle in both the second plane (xy) and the third plane (xz). The length of the seat 255 in the first direction is equal to the length of the first slot section 250a. The width of the seat 255 in the third direction is approximately equal to its length.

Through Holes, Blind Holes and Curved Rib

Two blind holes 256 are formed in the second face of the tail portion 220, the blind holes 256 being centred on corners of the seat 255 distal from the third edge 223 of the tail portion 220. The blind holes 256 have the same depth as the seat 255 so that the void defined by the seat 255 is contiguous with the blind holes 256.

Two through holes are formed through the tail portion 220, the through holes emerging in different quadrants of the seat 255 in the distal half of the seat 255 from the third edge 223 of the tail portion 220.

The tail portion 220 also includes a curved rib (shown in FIG. 4b described below) convex to the first face of the tail portion 220, the curved rib straddling the first slot section 250a between the two through holes.

Composite Groove

The second face of the tail portion 220 includes a composite groove 260 for receiving the parts of the leaf nut 450 and leaf nut holder 470 which are proud from the face of an adjacent leaf. The composite leaf 260 includes a second groove 260a and a third groove 260b of narrower width than the second groove 260a. The third groove 260b is seated inside (i.e. formed in the bottom surface of) the second groove 260a. Both the second groove 260a and the third groove 260b extend from the third edge 223 of the tail portion 220 towards a terminal end of the tongue 225. Both the second groove 260a and third groove 260b lie parallel to the leaf actuator screw slot 250 along the second face of the tail portion 220. The central axis of both the second groove 260a and third groove 260b are collinear and offset from the leaf actuator screw slot 250 in the fourth direction. The second groove 260a and third groove 260b are substantially the same length as the leaf actuator screw slot 250. The second groove 260a has the cross-sectional shape in the third plane (xz) of a high-aspect-ratio rectangle (third direction length:fifth direction width). The third groove 260b has the cross-sectional shape in the third plane (xz) of a minor segment of a circle. The cross-sectional shape of the composite groove 260 is shown in closer detail in FIG. 4a.

The edge of the seat 255 closest to the first edge of the tail portion 220 is aligned with the edge of the second groove 260a so that the void defined by the seat 255 is contiguous with the void defined by the second groove 260a.

Locking Joint Between the Tail Portion and Leaf Portion

The tail portion and leaf portion can be joined via one or more lap joints as shown in FIG. 2b and described in more detail below. This requires an adhesive in the joint region and/or another fastener to prevent the tail portion from being pulled apart from the leaf portion under the forces exerted on the leaf by the leaf drive mechanism. The reliance on an adhesive for strength in the plane of the leaf can be less than ideal, because application of a suitable adhesive to create a sufficiently strong and reliable joint can complicate the fabrication process, leading to increase in the cost of manufacture.

In embodiments, the joint between the tail portion and leaf portion is configured so as to prevent the leaf portion and tail portion from being pulled apart in the direction of movement of the leaf without an adhesive. This is achieved by using a locking (or interlocking) joint between the tail portion and leaf portion. Depending on the configuration of the locking joint, an adhesive may still be required to prevent forces acting out of the plane of the leaf from separating the tail portion from the leaf portion. However, in normal operation of the MLC, the greatest force acting on the leaf usually acts in the direction of movement of the leaf (i.e. in the longitudinal direction of the leaf). The locking joint ensures that a greater proportion of the forces acting in the longitudinal direction are exerted through the leaf material than through an adhesive.

The locking joint may additionally be configured to prevent separation of the tail portion from the leaf portion due to forces acting in the plane of the leaf other than in the longitudinal direction of the leaf. For example, the locking joint may additionally mechanically prevent movement of the tail portion relative to the leaf portion in the transverse direction in the plane of the leaf (i.e. in the plane of the leaf perpendicular to the direction of travel of the leaf). The locking joint may additionally be configured to prevent relative rotational movement of the tail portion and leaf portion in the plane of the leaf.

It may be understood that the tail portion is monolithic, and the leaf portion is also monolithic. The locking joint is formed from a protrusion which is monolithic with one of the tail portion and leaf portion (whichever has the protrusion) and a corresponding recess in the other of the tail portion and leaf portion.

In addition to providing a stronger mechanical joint between the tail portion and the leaf portion, the locking joint can also ensure better alignment between the tail portion and leaf portion during manufacture and during operation of the MLC. Prevention of misalignment can ensure smoother operation of the MLC and allows tighter tolerances between the leaves and other parts of the MLC, such as the leaf guides, which in turn allows more accurate positioning of the leaves during operation of the MLC.

Examples of a locking joint are shown in FIGS. 2c-2f. Each of FIGS. 2c-2f show a close up view of a locking joint between a leaf portion and tail portion of a leaf. The leaf may be identical to those shown in FIGS. 2*a* and 2*b*, however the skilled person will appreciate that the present disclosure is not limited thereto. For example, the leaf can be a simple rectilinear shape with no other features other than the locking joint between the tail portion and leaf portion.

The position of the locking joint is generally in the central region of the leaf, for example as shown by the joint 299*b* in FIG. 2*b*. However, the locking joint position is not limited thereto and can be further toward any of the four edges of the leaf depending on the configuration (e.g. shape and/or size) of the leaf portion and tail portion.

FIG. 2*c* shows a locking joint 299*c* including a dovetail-shaped protrusion 1215*a* of a tail portion 220*c* received by a corresponding dovetail-shaped recess 1225*a* in a leaf portion 210*c* thus forming a dovetail joint between the leaf portion 210*c* and tail portion 220*c*.

FIG. 2*d* shows a locking joint 299*d* including a lollipop-shaped protrusion 2215*a* of a tail portion 220*d* received in a corresponding keyhole-shaped recess 2225*a* of a leaf portion 210*d*.

FIG. 2*e* shows a locking joint 299*e* including a T-shaped protrusion 3215*a* of a tail portion 220*e* received in a corresponding T-shaped recess 3225*a* of a leaf portion 210*e*.

FIG. 2*f* shows a locking joint 299*f* including an arrow-shaped protrusion 4215*a* of a tail portion 220*f* received in a corresponding arrow-shaped recess 4225*a* of a leaf portion 210*f*.

A common feature of the embodiments shown in FIGS. 2*c*-2*f* is that there are mating faces (or edges) of the tail portion and leaf portion which provide a stop preventing an external force acting in the longitudinal direction (y) of the leaf from pulling the tail portion and leaf portion apart. That is, the locking joint is arranged such that tension applied between the leaf portion and tail portion in the longitudinal direction (y) of the leaf causes mating faces (or mating edges) of the leaf portion and tail portion to exert a force on each other which is proportional to said tension.

In some embodiments, the locking joint includes a plurality of adjoining pairs of corresponding features in the tail portion and leaf portion. That is, any of the aforementioned functions of the locking joint may be realised by the cooperation of more than one pair of corresponding features in the tail portion and leaf portion. The locking joint may include first and second pairs of corresponding features, wherein the first pair mechanically prevents relative movement of the tail portion and leaf portion in at least a first direction in the plane of the leaf whereas the second pair mechanically prevents relative movement of the tail portion and leaf portion in at least a second direction in the plane of the leaf. The first direction is different from the second direction.

The first direction is linear or rotational and the second direction is linear or rotational. For example, the first pair of corresponding features prevents relative linear movement between the tail portion and the leaf portion in the longitudinal direction of the leaf and the second pair prevents relative linear movement between the tail portion and the leaf portion in the transverse direction in the plane of the leaf perpendicular to the longitudinal direction. Together, the first and second pairs prevent relative rotational movement between the tail portion and leaf portion in the plane of the leaf.

In embodiments, the locking joint allows relative movement of the tail portion and leaf portion out of the plane of the leaf (e.g. perpendicular to the plane of the leaf). This allows the leaf portion and tail portion to be overlaid and fastened together in manufacturing by sliding the plane of the tail portion into coplanar alignment with the plane of the leaf portion. For example, the locking joint may be a sliding dovetail joint. Optionally, the locking joint may include an overlapping portion which acts as a stop to prevent further movement of the tail portion in the direction perpendicular to the plane of the leaf as it is brought into coplanar alignment with the leaf portion. For example, the locking joint may be a half blind lap dovetail joint. The overlapping portion increases the strength of the joint under forces acting out of the plane of the leaf.

In embodiments, an adhesive is added between mating surfaces of the locking joint. The overlapping portion of the locking joint described above increases the strength of the locking joint because when adhesive is added to the mating surfaces in the overlapping portion of the locking joint it increases the adhering contact area between the tail portion and the leaf portion. Whether or not an adhesive is used, the overlapping portion increases the strength of the locking joint under torsion and tensile forces.

Lap Joints Between Tail Portion and Leaf Portion

As shown in FIG. 2*b*, lap joints are formed between the leaf portion 210 and tail portion 220.

The edge of the recess 215 of the leaf portion 210 on the second face is the same as that on the first face except that it further includes a first indent 215*a*, a second indent 215*b* and a third indent 215*c*. The first indent 215*a* is concave from the central part of the bottom of the U shape of the recess 215. The second indent 215*b* and third indent 215*c* are concave from either side of the top of the U shape of the recess 215. The first, second and third indents 215*a*,*b*,*c* are formed through only half of the thickness of the leaf portion 210 and are recessed back from the second face of the leaf portion 210.

The tongue 225 of the tail portion 220 comprises first, second and third protrusions 225*a*, 225*b*, 225*c* corresponding in shape and dimension to first, second and third indents, respectively. The first, second and third protrusions 225*a*, 225*b*, 225*c* are a half thickness of the tail portion 220 and have surfaces which are flush with the second face of the tail portion 220.

The lap joints joining the tail portion 220 and the leaf portion 210 are formed by faces of the leaf portion 210 formed by the first, second and third indents interfacing with faces of the first, second and third protrusions, respectively.

It may be understood that the present disclosure includes lap joints between the tail portion and leaf portion whether or not they are of the locking type described herein. It may also be understood that the present disclosure includes interlocking (or locking) joints between the tail portion and leaf portion whether or not they include an overlap (i.e. as in a lap joint) as described herein.

Leaf Nut and Leaf Nut Holder

FIG. 3*a* shows a leaf nut 450 located in situ in the first slot section 250*a* and a leaf actuator screw 430 passing through the leaf nut 450 and located in situ in the first and second slot sections 250*a*, 250*b* of the leaf actuator screw slot 250. FIG. 3*b* is a cross section in a plane parallel to the third plane (xz) and passing through the leaf nut 450, the leaf actuator screw 430 the tail portion 220 in the vicinity of the seat 255.

Leaf Nut

The leaf nut 450 is shown in FIG. 3*a*, and in cross-section in FIG. 3*b*. The leaf nut 450 provides a threaded part for the leaf actuator screw 430 to engage therewith in order to convert the rotational motion of the leaf actuator screw about its axis to linear motion in the first and second directions. The leaf nut 450 includes parts 451, 452 which engage with the tail portion 220 in order to resist the rotational force applied to the leaf nut 450 by the rotation of the leaf actuator screw 430. These parts 451, 452 (described in more detail below) allow limited movement of the leaf nut 450 to accommodate misalignment of the leaf drive units 400.

The leaf nut 450 comprises a cylindrical part 457 having a through hole coaxial with the cylindrical part 457. The through hole is dimensioned and threaded to receive the leaf actuator screw 430. The length (i.e. dimension in the first direction when the leaf nut 450 is in situ in the first slot section 250*a*) of the cylindrical part 457 is approximately equal to two thirds the length (in the first direction) of the first slot section 250*a*.

The leaf nut 450 also comprises a first block 451 and second block 452 extending outward from opposing portions of the outer cylindrical face of the cylindrical part 457. The first block 451 extends outward from the outer cylindrical face of the cylindrical part 457 in the first direction (when the leaf nut 450 is in situ in the first slot section 250*a*). The second block 452 extends in the opposite direction to the first block 451 (i.e. in the second direction when the leaf nut 450 is in situ). The length of the first block 451 in the direction of the central axis of the cylindrical part 457 (i.e. the first direction in situ) is equal to the length of the cylindrical part 457 so that the end faces of the cylindrical part 457 are flush with the end faces of the first block 451. The width (i.e. dimension in the fifth direction in situ) of the first block 451 is greater than the internal diameter of the threaded through hole of the leaf nut 450 and less than the outer diameter of the cylindrical part 457.

The first block 451 has a first blind slot 454 formed therein, the first blind slot 454 extending in the second direction from the face of the first block 451 lying parallel to the second plane (xy). The first blind slot 454 runs along the full length of the first block 451 in the first direction. The first blind slot 454 is positioned so that one inner face thereof lies in a plane which lies parallel to the first plane (yz) and passes through the central axis of the cylindrical part 457. In this way, the centre of the first blind slot 454 aligns to one side of the centre of the cylindrical part 457 when viewed in the third plane (xz). This aligns the leaf actuator screw 430 to be more central in relation to the tail portion of the leaf.

The dimensions of the second block 452 and a second blind slot 456 in the second block 452 are the same as those of the first block 451 and first blind slot 454, respectively. The second block 452 and second blind slot 456, respectively, mirror the first block 451 and first blind slot 454 about a plane parallel to the second plane (xy) passing through the central axis of the cylindrical part 457. That is, both the blocks and the blind slots are symmetrical about the plane parallel to the second plane (xy) passing through the central axis of the cylindrical part 457.

The widths first blind slot 454 and second blind slot 456 are dimensioned to receive parts of the tail portion 220 in the seat 255 either side of the first slot section 250*a*. The parts of the blocks either side of the blind slots straddle the tail portion 220 in the footprint of the seat. This part of the tail portion 220 cooperates with the first block 451 and second block 452 to prevent rotational motion of the leaf nut 450 about the central axis of the cylindrical part 457 when the leaf nut 450 is in situ. Thus, the torque of the leaf actuator screw 430 applied to the leaf nut 450 when the leaf actuator screw 430 is rotated about its axis does not translate into rotation of the leaf nut 450.

The depths (i.e. dimensions in the first direction) of the first blind slot 454 and second blind slot 456 are such that leaf nut 450 can travel a limited (but non-zero) distance in the first and second directions in the first slot section 250*a*. The movement of the leaf nut 450 in these directions accommodates small misalignments of the leaf actuator screw 430, for example due to misalignments of the leaf actuator motors in the mounting plate 510, or misalignment of the mounting plate 510 relative to the leaf bank 20.

Leaf Nut Holder

Figure 4A:
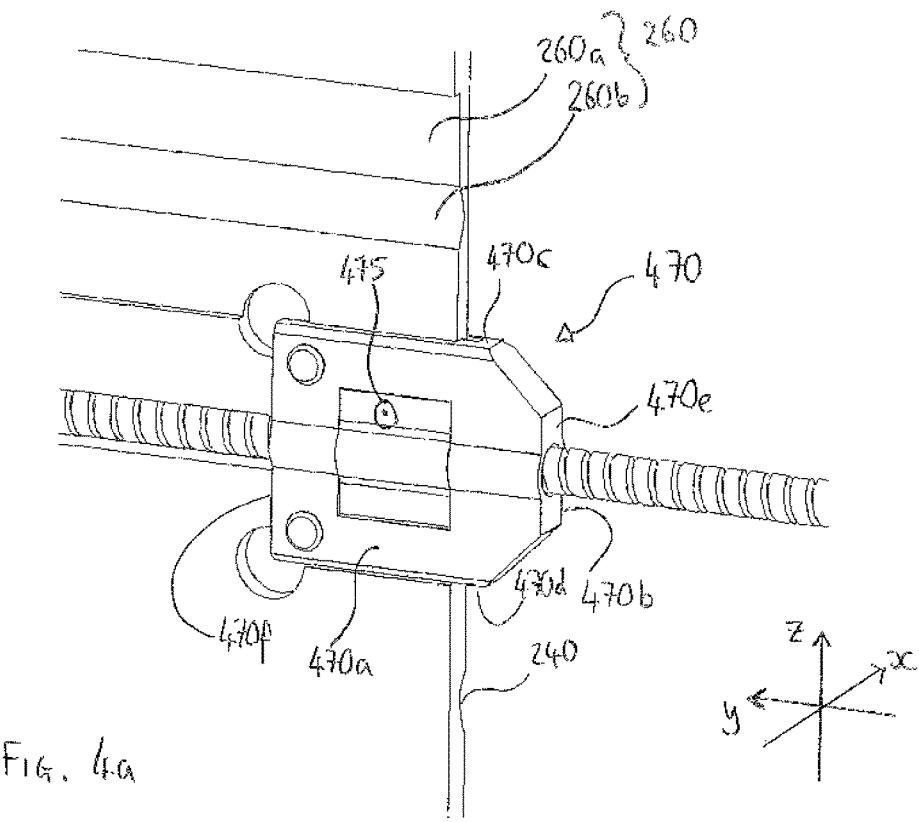
FIGS. 4a and 4b show isometric views of a leaf nut and leaf nut holder according to an embodiment installed in the tail portion of a leaf, FIG. 4a also shows an isometric view of a face of the tail portion of a leaf according to an embodiment.
Figure 4B:
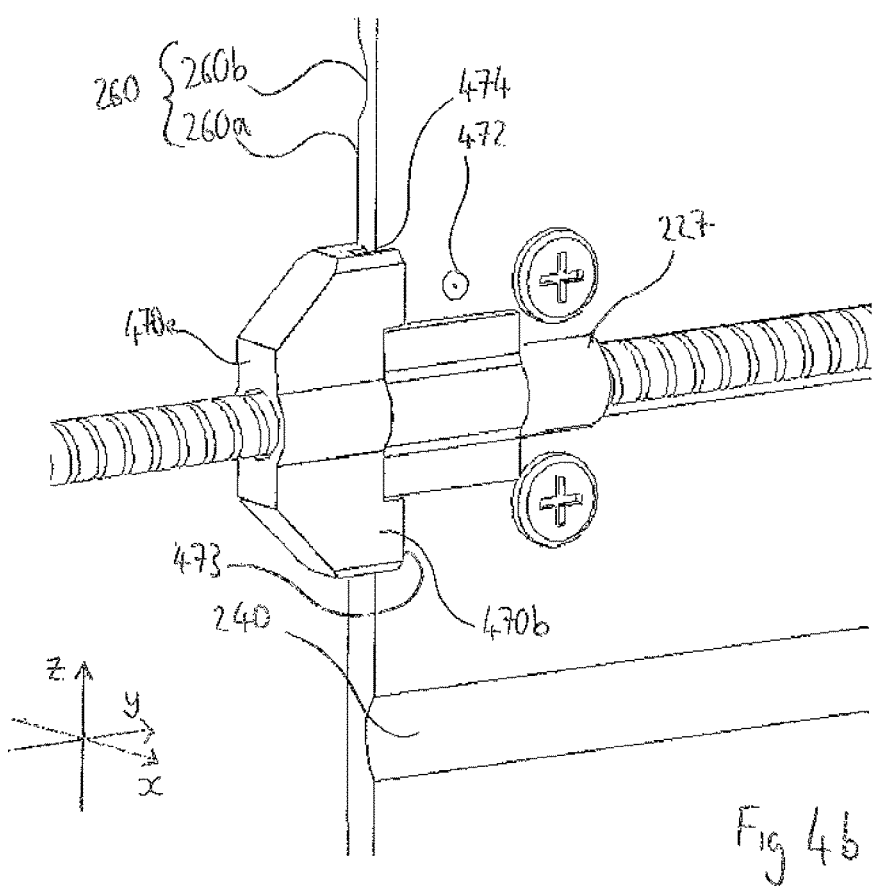

FIGS. 4*a* and 4*b* show a leaf nut holder 470 arranged to hold the leaf nut 450 in position in the tail portion 220 of the leaf 200. FIG. 4*a* shows an isometric view of the second face of the tail portion 220 in the vicinity of the seat 255. FIG. 4*b* shows an isometric view of the first face of the tail portion 220 in the vicinity of the seat 255.

The leaf nut holder 470 is structure for housing the leaf nut 450. The leaf nut holder can be coupled to the leaf 200. The leaf nut holder 470 prevents linear movement of the leaf nut 450 in the direction of the axis of the leaf actuator screw 430. The leaf nut holder 470 allows limited (non-zero) movement of the leaf nut 450 in the plane of the leaf 200.

Notwithstanding the features described below, the leaf nut holder 470 is a substantially oblong block having a length (i.e. dimension in the first direction when in situ in the tail portion 220) approximately 50% larger than the length of the seat 255 and a width (i.e. dimension in the third direction when in situ) substantially equal to the width of the seat 255. When in situ on the tail portion 220 of the leaf 200, the leaf nut holder 470 has a first face 470*a* and a second face 470*b* each substantially parallel to the first plane (yz), a third face 470*c* and fourth face 470*d* each parallel to the second plane (xy) and a fifth face 470*e* and sixth face 470*f* each parallel to the third plane (xz). The cross-sectional profile of the leaf nut holder 470 in the third plane (xz) is such that the first face 470*a* of the leaf nut holder 470 has a surface topography which is the inverse of that of the composite groove 260 in the second face of the tail portion 220. Notwithstanding the features described below, the second face 470*b* of the leaf nut holder 470 has a surface topography which is the mirror image of the first face 470*a* about a plane parallel to the first plane (yz) passing through the centre of the leaf nut holder 470.

A nut guide 475 arranged to receive the leaf nut 450 is formed through the leaf nut holder 470. The nut guide 475 is an aperture passing approximately centrally through the leaf nut holder 470 in the fifth direction. The length of the nut guide 475 (in the first direction) is substantially the same as the length of the leaf nut 450. Thus, movement of the leaf nut 450 is restricted by the leaf nut holder 470 in the first and second directions. The width of the nut guide 475 (in the third direction) is marginally greater than the width of the leaf nut 450 so that movement of the leaf nut 450 is permitted inside the nut guide 475 in the third and fourth directions. The range of movement of the leaf nut 450 allowed by the cooperation of the first blind slot 454 and second blind slot 456 in the leaf nut 450 with the first slot section 250*a* in the tail portion 220 is substantially equal to the range of movement of the leaf nut 450 allowed by the width of the nut guide 475.

The leaf nut holder 470 has a cutaway portion 472 to receive the second face of the tail portion 220 of the composite leaf 200. The cutaway portion 472 is recessed back into the leaf nut holder 470 in the sixth direction from the second face 470*b* of the leaf nut holder 470. A void formed by the cutaway portion 472 extends over the full width and over more than half of the length of the leaf nut holder 470 so that the cutaway portion 472 defines a single shoulder 473 running in the first direction and having a face parallel to the third plane (xz). A locating slot 474 is formed in the face of the shoulder to receive the third edge 223 of the tail portion 220.

The leaf nut holder 470 has two threaded through holes extending in the third direction. The axes of the threaded through holes are collinear with the respective axes of the two through holes in the seat 255 when the leaf nut holder 470 is in situ on the tail portion 220. The leaf nut holder 470 is fixed to the tail portion 220 by screws inserted through the respective through holes in the seat 255 and into the threaded through holes in the leaf nut holder 470. A ridge formed by the shoulder 473 and locating slot 474 formed therein provides further rigidity by applying a resistive force to third edge 223 of the tail portion 220 to prevent the end of the leaf nut holder 470 farthest from the leaf portion 210 from moving in the sixth direction. The locating slot provides a resistive force which prevents the leaf nut holder 470 from moving in the first direction. Thus, the third edge 223 of the tail portion 220 forming an edge of the seat 255 is received in the slot so that the leaf nut holder 470 straddles this part of the tail portion 220.

The fifth face 470e of the leaf nut holder 470 is that parallel to the third plane and distal from the leaf portion 210 when in situ. A screw guide hole 478 is formed in the leaf nut holder 470 which extends from the centre of the fifth face 470e and in the first direction through the volume of the leaf nut holder 470. The screw guide hole 478 receives the leaf actuator screw 430 and provides clearances in the third, fourth, fifth and sixth directions which allow movement of the leaf actuator screw 430 inside the leaf nut holder 470 in these directions. Thus, the leaf nut holder 470 is arranged to allow movement of the leaf nut 450 and the leaf actuator screw 430 relative to the leaf nut holder 470 (and thus relative to the tail portion 220 of the composite leaf) in the third and fourth directions.

The leaf nut holder 470 includes 45-degree chamfers between the third face 470c and the fifth face 470e, and between the fourth face 470d and the fifth face 470e so that the dimension of the fifth face 470e in the third direction is around a half that of the leaf nut holder 470.

Chamfers are also formed between the third face 470c and each of the first and second face 470b and between the fourth face 470d and each of the first face 470a and second face 470b of the leaf nut holder 470. These chamfers enable smoother movement of the leaf nut holder 270 of one leaf in the composite or first groove of an adjacent leaf.

Where the terms attenuation factor, attenuation factor per unit width, attenuation factor per unit length and attenuation factor per unit area are used, it may be understood that these parameters are measured (or calculated) in the radiation energy range 6 MeV to 25 MeV, or a subrange therein, e.g. 6 MeV to 10 MeV.

Leaf Actuator Screw

The leaf actuator screw 430 is a threaded rod having a length approximately equal to the full length of the leaf actuator screw slot 250 in the tail portion 220 of the leaf 200. The pitch and diameter of the thread match those of the leaf nut 450. The thread of the leaf actuator screw 430 extends along its full length except in the vicinity of the leaf motor 410, where it includes a non-threaded section 430a.

Figure 5:
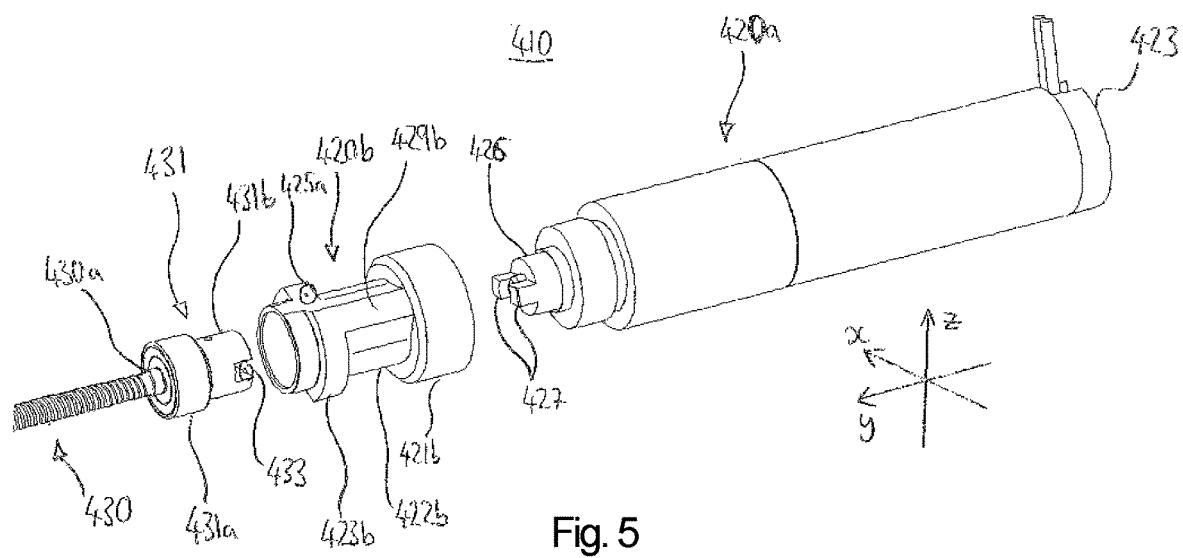
FIG. 5 shows an exploded view of one implementation of a leaf motor and the interface between the leaf actuator screw and the leaf motor.

FIG. 5 shows an exploded view of one implementation of a leaf motor 410 and the interface between the leaf actuator screw 430 and the leaf motor 410. The leaf actuator screw 430 includes a first coupling member 431 fixed to the end of the non-threaded section 430a. The first coupling member 431 comprises a first cylindrical section 431a for receiving and forming a rigid connection with the non-threaded section 430a of the leaf actuator screw 430. A second cylindrical section 431b having a smaller diameter than the first cylindrical section 431a extends in the second direction from an end face of the first cylindrical section 431a. The second cylindrical section 431b has a coupling groove 433 formed across an end face thereof.

Leaf Motor

In the implementation shown in FIG. 5, the leaf motor 410 includes a leaf motor casing 420. The leaf motor casing includes a first casing 420a and a second casing 420b removable from the first casing 420a. The leaf motor 410 further includes a second coupling member 426 fixed to an output shaft of the motor and having coupling protrusions 427 arranged to interlock with the coupling groove 433 in the second cylindrical section 431b of the first coupling member 431.

The first casing 420a is arranged to enclose a rotor, stator and commutator of the leaf motor 410, but not the second coupling member 426, which protrudes from an end of the first casing 420a. The first casing 420a includes a main section including two cylindrical tubes having the same diameter and arranged end to end.

At a first end of the main section, the casing has a neck smaller in diameter than the main section. The neck includes a flange which forms a terminal end of the first casing 420a, the second coupling member 426 protruding in the first direction from said terminal end.

At a second end of the main section opposite the first end, there is an end cap 423 having the same diameter as the two cylindrical tubes. The end cap 423 has a wiring cutaway in one part of the circumferential region of the end cap 423 for allowing two wires connected to the internal components of the leaf motor 410 to protrude side by side from the end cap 423 in a radial direction of the end cap 423.

The second casing 420b includes a cap section 421b arranged to fit over the neck and flange of the first casing 420a. The second casing also includes a neck section 422b having a diameter smaller than that of the cap section 421b, the neck section having the leaf motor casing mounting flange 425 described earlier around the circumference thereof. The second casing 420b is arranged to house the first coupling member 431 and second coupling member 426 in the neck section 422b thereof.

Motor with Integral Casing and Integral Leadscrew

Figure 6:
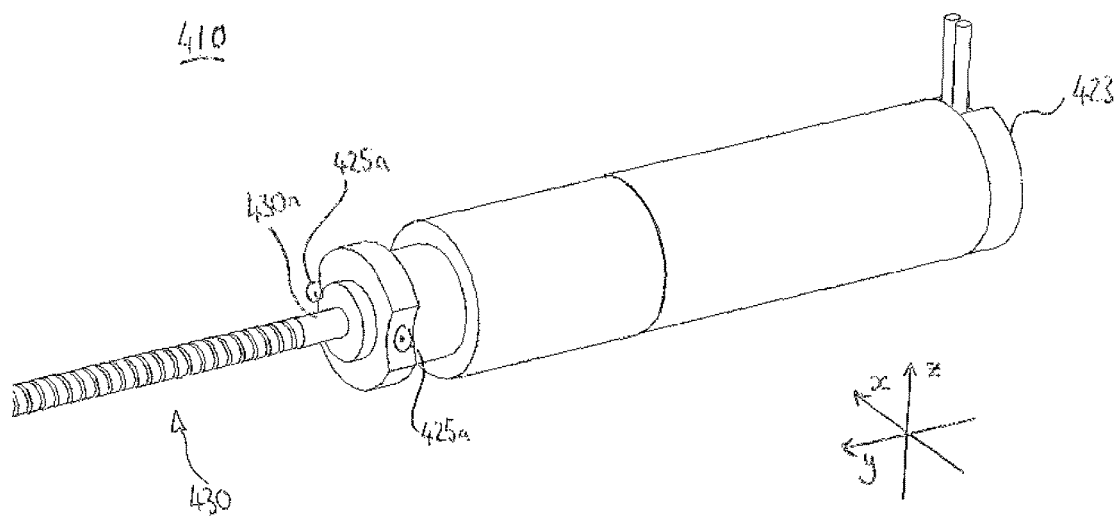
FIG. 6 shows a different implementation of the leaf motor to that shown in FIG. 5.

FIG. 6 shows a different implementation of the leaf motor 410 than that shown in FIG. 5. In the implementation of FIG. 6, the leaf motor 410 includes a leaf motor casing 420 having substantially the same outer appearance as the first casing 420a and second casing 420b described above. In this implementation, the leaf motor casing 420 is also arranged to enclose the rotor, stator and commutator. However, instead of being removably coupled to the motor output shaft, the leaf actuator screw 430 is integrally formed with the motor output shaft. Put another way, the leaf actuator screw 430 is the motor output shaft. That is, the motor output shaft and the leaf actuator screw may be formed from one monolithic rod.

The leaf motor casing 420 includes a main section including two cylindrical tubes having the same diameter and arranged end to end. At a first end of the main section, the casing includes a neck smaller in diameter than the main section and connected by a shoulder to the main section. The neck includes a mounting flange 425, which is substantially the same as that described with reference to FIG. 5. At a second end of the main section opposite the first end, there is an end cap 423 substantially the same as the end cap described with reference to FIG. 5.

The neck of the leaf motor casing 420, the mounting flange, the shoulder connecting the neck to the main section and the cylindrical tube adjacent the shoulder are monolithic. Alternatively, these parts of the leaf motor casing are separate but pressed/bonded together so that they are not removable without deformation. That is, these parts of the leaf motor casing are integrally formed so that they are not removable from each other.

Mounting of the Leaf Motor in the Mounting Plate

Figure 7A:
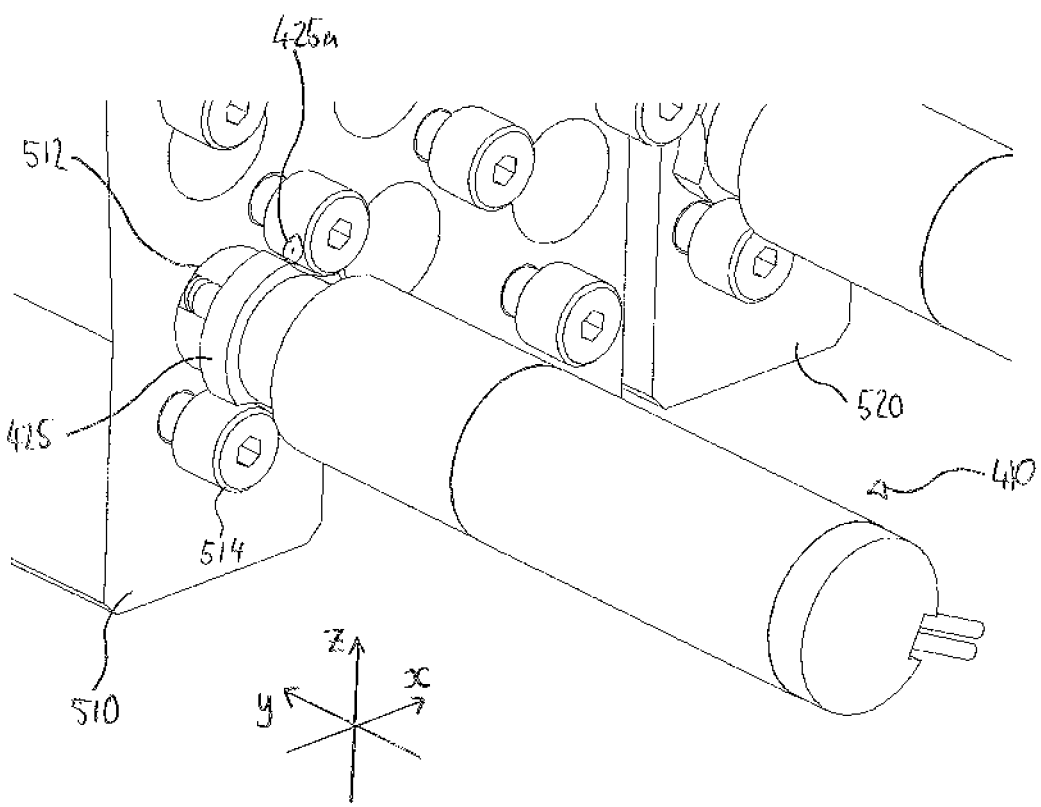
FIGS. 7a and 7b each show an isometric view of leaf motor of FIG. 6 and the mounting thereof in one of the mounting plates.
Figure 7B:
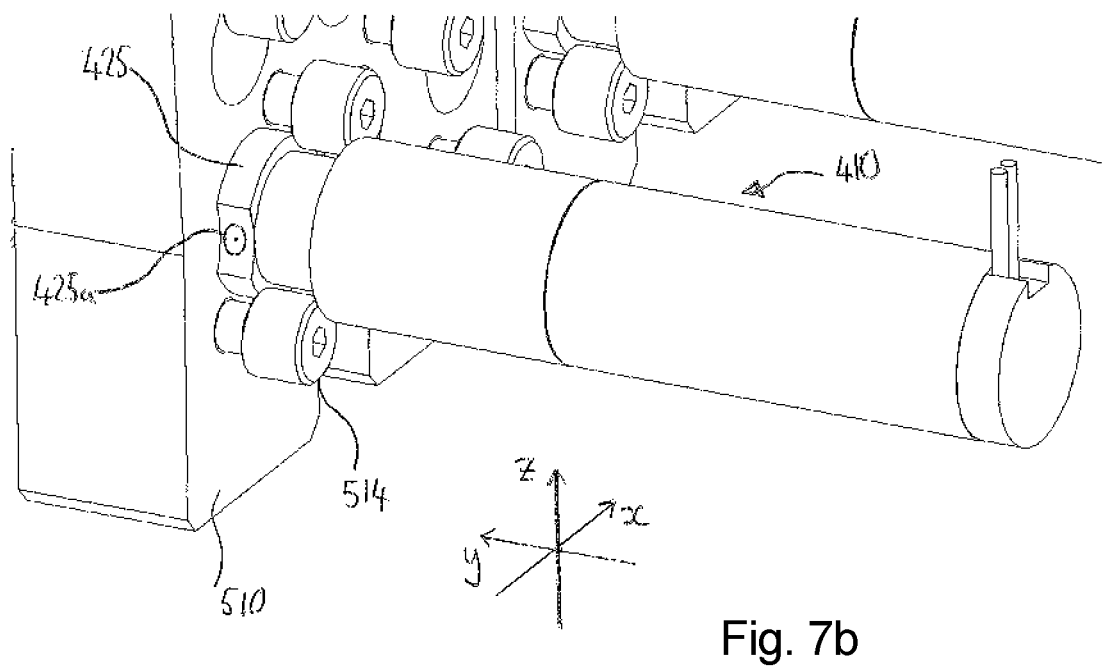

FIGS. 7*a* and 7*b* each show an isometric view of leaf motor 410 of FIG. 6 and the mounting thereof in one of the mounting plates 510. FIG. 7*a* shows the rotational position of the leaf motor relative to the mounting plate upon insertion or removal of the leaf motor from the mounting hole 512. FIG. 7*b* shows the rotational position of the leaf motor 410 relative to the mounting plate when the leaf motor is inserted into the mounting hole 512 and locked in position by two mounting screws 514.

As described earlier, the leaf motor casing 420 is mounted to a respective mounting plate 510 by two mounting screws 514 cooperating with the mounting flange 425 to hold the mounting flange 425 to the second face of the mounting plate 510. The mounting flange 425 further includes two curved recesses 425*a* each arranged to receive an edge of the head of a corresponding mounting screw 514 located to one side of the mounting hole 512 in the mounting plate 510. The two curved recesses 425*a* are at opposite positions relative the central axis of the leaf motor casing 420, so that in a particular rotation of the leaf motor 410 about the first direction, they are able to locate with corresponding mounting screws 514 positioned on opposite sides of the mounting holes 512. The curved recess 425*a* has a shape and dimensions which correspond to those of the part of the head of the mounting screw 514 which normally overlaps the mounting flange 425.

Thus, by turning the leaf motor casing 420 about its axis, it can adopt one of two rotational positions relative to the respective mounting plate 510. The two rotational positions include a first rotational position (see FIG. 7*a*) in which the mounting screws 514 each completely overlap a respective curved recess 425*a* in the mounting flange 425, and a second rotational position (see FIG. 7*b*) in which the mounting screws 514 each overlap a portion of the mounting flange 425.

In the first rotational position, the end of the leaf motor 410 can be inserted into the mounting hole 512 in the mounting plate 510 even when the corresponding mounting screws 514 are in position in the mounting plate 510. This is because each curved recess is arranged to receive the edge of the head of the mounting screw 514. Following insertion of the end of the leaf motor 410 into the mounting hole 512, the leaf motor casing 420 can be rotated to the second rotational position.

In the second rotational position, the leaf motor casing 420 can be held against the mounting plate 510 by tightening the mounting screws 514 so as to urge the mounting flange 425 against the second face of the mounting plate 510.

By loosening the mounting screws 514, the leaf motor casing 420 can be rotated back to the first rotational position. In the first rotational position, the leaf motor casing 420 can also be removed from the mounting hole 512 in the mounting plate 510 even when the corresponding mounting screws 514 are in position in the mounting plate 510, again because the two curved recesses 425*a* are each shaped and dimensioned to receive the edge of the head of a respective mounting screw.

Referring back to FIG. 5, a ridge 429*b* may be located in neck section 422*b* between the cap section 421*b* and the mounting flange 425. The top surface of the ridge 429*b* (i.e. the surface distal from the outer circumferential surface of the neck section 422*b*) is flush with the outer circumferential surface of the mounting flange 425. The sides of the ridge cross section are convex and the circumferential position of the ridge 429*b* around the neck section 422*b* is such that one side of the ridge 429*b* is flush with one half of the curved recess 425*a*. The shape and position of the ridge 429*b* are such that the side surface of the ridge flush with the curved recess 425*a* acts as a locating surface for the curved recess 425*a*. The purpose of the ridge 429*b* is to increase the cross section of the neck section 422*b* because the wall thickness of the neck section 422*b* is typically fairly thin. Thus, the ridge 429*b* gives the neck section 422*b* greater stiffness. Additionally, the ridge 429*b* acts as a stop (i.e. locating means) and limits the rotation of the leaf motor casing 420 once it is engaged under the head of the mounting screw 514. Visibility of the mounting screws 514 is limited due to motors and components obscuring the view. The ridge 429*b* assists in collocating the curved recess 425*a* and the mounting screws 514. If the ridge 429*b* was not present it would be possible to continue rotating the leaf motor casing 420 until the mounting flange would be inadvertently engaged/disengaged with the screw heads again.

That is, without the ridge 429*b*, sight of the mounting flange 425 is necessary to ensure that the leaf motor casing 420 can be rotated accurately to the first rotational position when the leaf motor 410 is inserted into the mounting hole 512. Otherwise the leaf motor 410 must be pulled in the second direction while rotating. However, with the ridge 429*b* included, the leaf motor casing 420 can be rotated until the head of the mounting screw meets the locating surface of the ridge 429*b*. The first rotational position is then assured and the leaf motor 410 can be removed from the mounting hole 512. A corresponding ridge is located on the opposite side of the neck section 422*b* to provide a locating surface for the corresponding curved recess 425*a* on the opposite side of the flange.

Leaf Drive Mount

Figure 8:
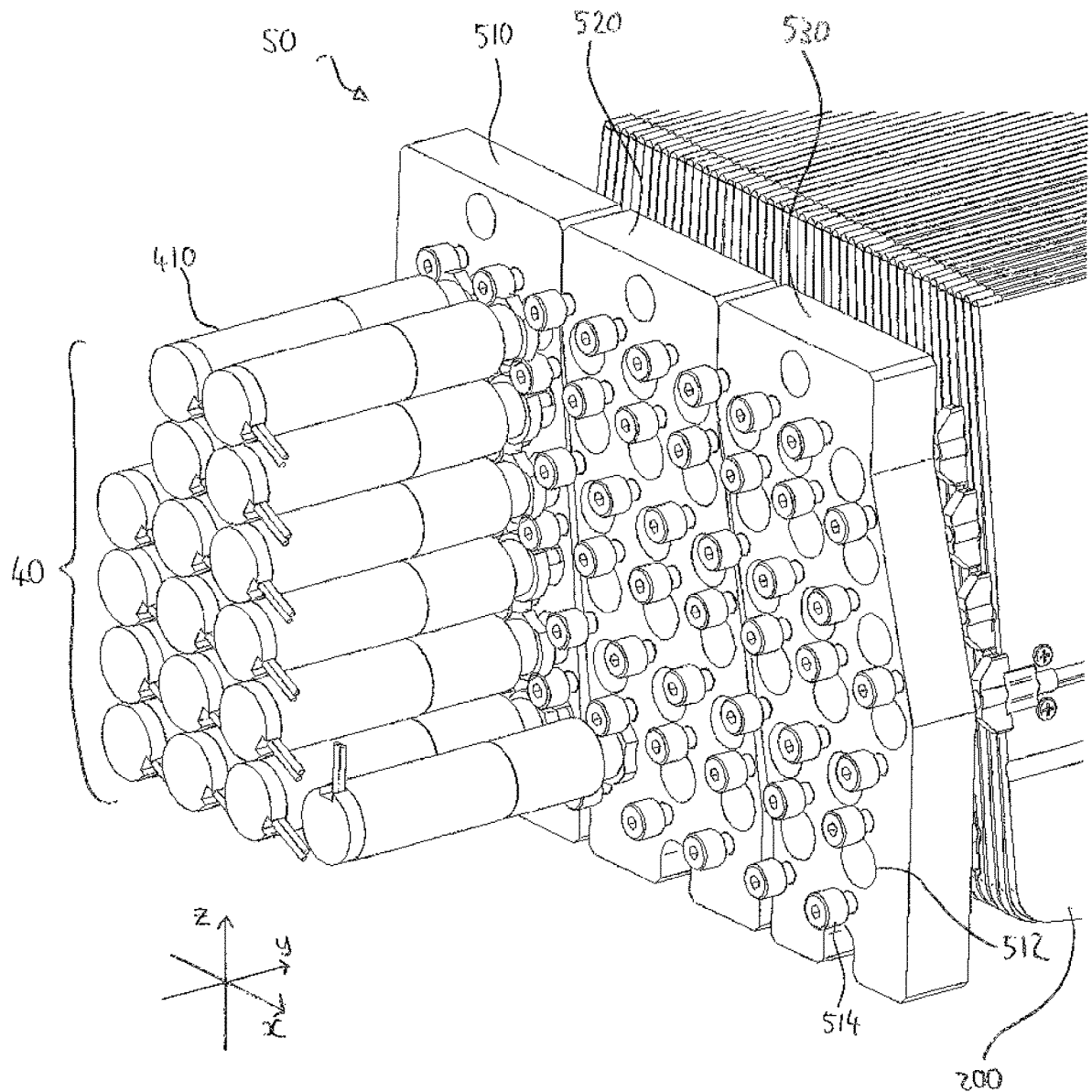
FIG. 8 is an isometric view of a mount.

FIGS. 8 and 9 show detailed views of the leaf drive mount 50 in situ with the other components of the multi-leaf collimator assembly 100. FIG. 8 is an isometric view and FIG. 9 is an elevation view in the first direction.

As shown in FIGS. 8 and 9, the leaf drive mount includes a first mounting plate 510, a second mounting plate 520 and a third mounting plate 530. The mounting plates 510, 520, 520 are separable from each other to facilitate ease of servicing and maintenance.

Each of the mounting plates 510, 520, 530 has a first face parallel to the third plane (xz) and proximal to the leaves 200, and a second face parallel to the first face and distal from the leaves 200. In use, the leaves 200 are situated between the leaf drive mount 50 and the path of the radiation beam, such that the leaf drive mount 50 lies behind a tail portion 220 of the leaves 200 and intersects the plane of each of the leaves 200.

Each of the mounting plates 510, 520, 530 contains a two-dimensional array of mounting holes 512, each of the mounting holes 512 having a central axis in the first direction and passing through the mounting plate 510 between the first face and the second face. Each of the mounting holes 512 is arranged to receive the cylindrical neck of a leaf motor casing 420 of one of the leaf motors 410 inserted into the mounting hole 512 in the first direction from the side of the mounting plate 510 having the second face. The leaf actuator screw 430 corresponding to the respective leaf motor 410 passes through the mounting hole 512 and emerges from the side of the mounting plate 510 having the first face. The mounting flange 425 of the leaf motor casing 420 is arranged to engage with the second face of the mounting plate 510 so as to prevent the whole of the neck of the casing from being insertable into the mounting hole 512. Thus, the leaf motor movement in the first direction is restricted by the mounting flange 425.

Each of the mounting plates 510, 520, 530 includes an array of threaded holes in the second face thereof for receiving respective mounting screws 514. When in situ in the threaded holes, the mounting screws 514 are arranged to overlap a face of the mounting flange 425 distal from the mounting plate 510 so as to prevent movement of the leaf motor 410 in the second direction.

The 2D array of mounting holes 512 in each mounting plate 510, 520, 530 includes three columns. Each of the columns is arranged at an acute angle to the third direction to take into account the staggered positioning of the leaf drive units 400 described earlier. The array is arranged in six rows, and the pattern of staggering of the leaf drive units 400 repeats every six leaves in the fifth direction.

As shown in FIG. 9, the sides of the mounting plates are angled to be substantially parallel to the angled columns. This allows consistent spacing of the leaf drive units 400 in the fifth direction by permitting a separation of the order of the width of a leaf 200 between a first mounting hole 512A in the final row of the final column of one mounting plate 520 and a second mounting hole 512B in the first row of the first column of an adjacent mounting plate 530.

A mounting screw 514 (i.e. the aforementioned retainer) is arranged on two opposing sides of every mounting hole 512. The mounting screws form a 2D array having rows between the rows of mounting holes 512 and columns between the columns of mounting holes. The mounting screws are positioned such that one mounting screw 514 can interact with one leaf motor in the mounting hole row above and one leaf motor in the mounting hole row below. Thus, the number of mounting screws can be reduced.

Leaf Bank Actuator Overview

In prior art MLCs, a leaf guide associated with each leaf bank performs two functions. First, the leaf guide acts as a guide for the movement of the individual leaves in the leaf bank when the leaves are moved relative to one another. The leaves engage with the leaf guide such that the lateral position of the tips of the individual leaves are governed by the leaf guide. Second, the leaf guide acts as an integral part of the carriage for moving the entire leaf bank (i.e. for moving all leaves in the leaf bank as a unit). That is, when the individual leaves of one leaf bank are moved relative to each other, the leaf guide associated with that leaf bank remains static relative to the moving leaves and therefore the leaves move relative to the leaf guide. A carriage, which moves linearly back and forth along a motor stage, carries the leaf bank. When the leaf bank is moved as unit, the leaf guide functions as part of the carriage, moving in unison with and carrying all leaves in the leaf bank.

The leaf guides move with the leaf banks. When moving the leaf banks there may be unintended lateral movement, for example due to manufacturing tolerances in the motor stages, translates into unintended lateral movement of the leaf guides, and therefore of the leaf tips, when the leaf bank is moved as unit.

This unintended lateral movement means the position of the leaves of the multi-leaf collimator relative to the other component of the radiotherapy device, in particular to the radiation beam, may not be accurately known or controlled. Additionally, as separate carriages carry the leaf banks in the multi-leaf collimator, the risk of lateral misalignment of the leaves of one leaf bank relative to the other leaf bank increases with decreasing tolerances in the stages on which the carriages move. Therefore, in prior art MLCs, accurate and reliable lateral positioning of the leaves along the full range of motion of the leaf banks is assured by the manufacturing tolerance/accuracy of the carriage stages. However, this increases the cost and complexity of the MLC.

In embodiments, a 'leaf bank actuator' replaces the carriage as the primary means for moving the leaf bank as whole. An important characteristic of the leaf bank actuator is that it moves the leaf bank as a unit relative to the leaf guide. The leaf bank actuator pushes the leaf bank back and forth relative to the leaf guide while the leaves are in contact with the leaf guide. This allows the leaf guide to guide the movement of the leaves both when the individual leaves are moved relative to each other and when the leaf bank is moved as a unit.

The leaf guide's guidance of the leaves when the leaf bank moves as one unit allows more accurate and reliable lateral positioning of the leaves along the full range of motion of the leaf bank. A further advantage is that the leaf guide can remain in a fixed position in the reference frame of the beam limiting device (or MLC) while the leaf bank moves in this frame of reference. With a static leaf guide, the lateral position of the leaves relative to the radiation beam can be more easily controlled along the full range of motion of the leaf bank. In addition, the lateral position of the leaves in one leaf bank relative to other components of the MLC can be more easily controlled along the full range of motion of the leaf bank. For example, if the leaf guides of the two opposing leaf banks in a multi-leaf collimator are both static while the leaf bank moves, there can be more reliable matching of the lateral positions of the leaves of the one leaf bank relative to the other. In this way, the interdigitation of the leaves in opposing leaf banks can be made more reliable using a less complex and/or less expensive apparatus compared with the carriage design of prior art MLCs.

Prior Art MLC with Carriages to Move the Leaf Banks

In a typical multi-leaf collimator, the leaves are individually motorised in order to allow them to be moved into and out of the path of the radiation beam along a first axis (which axis is in the plane of the leaf and parallel to the longitudinal dimension of the leaf). Each leaf bank is mounted in a structure which is moveable on a motorised stage. This structure is usually referred to as a "carriage". Thus, the leaves are supported on and movable relative to their respective carriage, and each carriage is mounted on and moveable along the first axis relative to a substrate, base or mount. The carriages include leaf guides, which are structured for supporting and guiding the leaves in their travel back and forth along the first axis.

Figure 10:
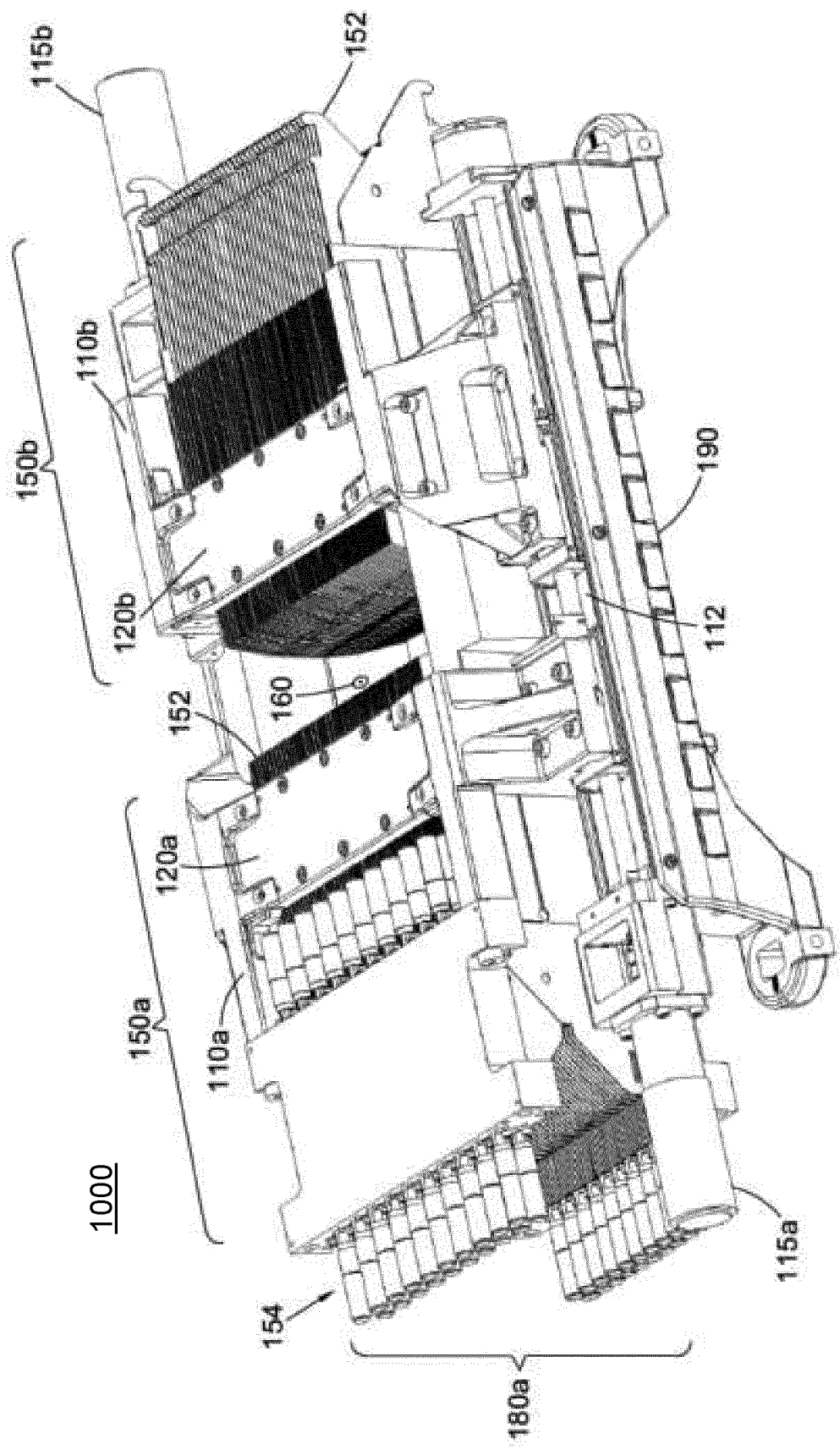
FIG. 10 shows a multi-leaf collimator according to the prior art.

FIG. 10 shows a multi-leaf collimator 1000 according to the prior art. The multi-leaf collimator includes two leaf banks 150a, 150b, each leaf bank 150a, 150b including a plurality of leaves 152. The leaves 152 are individually moveable longitudinally within the leaf bank 150a, 150b so that they can project into and out of the path of a radiation beam passing through an aperture 160 between the two opposing leaf banks 150a, 150b. The leaves 152 are relatively thin so as to allow a high-resolution aperture shape to be obtained, but they are relatively deep in the direction of the axis of the radiation beam in order to render them sufficiently opaque at X-ray energies. The leaves 152 are relatively elongate (relatively long in the direction perpendicular to their thickness and depth) so as to allow them to adopt a wide range of positions.

The leaves are guided and supported by leaf guides 120a, 120b. The leaf guides 120a, 120b are structures which support the weight of the leaves 152 and guide them in their linear motion into and out of the path of the radiation beam. In the multi-leaf collimator shown in FIG. 10, the leaf guides 120a, 120b are parts of respective carriages 110a, 110b which carry the leaves 152.

For each leaf bank 150a, 150b, there is a leaf actuator array 180a (not shown for one of the leaf banks 150b). Each leaf actuator array 180a includes an array of leaf actuators 154. Each leaf actuator comprises an assembly including a leaf motor, leaf actuator screw and leaf nut. An output shaft of the leaf motor is connected to one end of the leaf actuator screw so that rotation of the output shaft translates directly into rotation of the leaf actuator screw. The leaf actuator screw is engaged with the thread of the leaf nut and the leaf nut is rigidly coupled to the leaf. Thus, rotation of the leaf actuator screw relative to the leaf causes relative linear motion between the leaf actuator screw and the leaf nut (and hence also the leaf).

Thus, each leaf actuator 154 is arranged to drive a respective leaf so that the leaves 152 can be moved in their respective leaf banks 150a, 150b independently of each other. That is, each leaf actuator 154 is arranged to engender relative linear motion between one leaf 152 and the other leaves in the leaf bank. A suitable controller will typically be provided (not shown), which is arranged to provide signals to the leaf actuators 154 in order to move the appropriate leaf or leaves 152 to provide the required shape or position of the aperture 160.

The multi-leaf collimator 1000 includes a base 190 arranged to carry and support the weight of the other components in use. The carriages 110a, 110b are linearly moveable along carriage (motor) stages 112 relative to the base 190. Respective carriage actuators 115a, 115b (e.g. carriage motors) are arranged to engender relative linear motion between each carriage 110a, 110b and the base 190. As the leaf guides 120a, 120b are part of (or are rigidly fixed to) their respective carriages 110a, 110b, the leaf guides 120a, 120b move with their respective carriages.

The leaf bank motion is dependent upon the leaf guide motion due to the rigid coupling of the carriage 110a to both the leaf actuator array 180a and the leaf guide 120a. Each leaf actuator array 180a is rigidly coupled to a mount which is part of (or rigidly attached to) a respective carriage 110a, 110b. In addition, each leaf guide 120a, 120b is rigidly attached to the respective carriage 110a, 110b. Therefore, for each leaf bank 150a, 150b, the leaf actuator array 180a is rigidly coupled to the leaf guide 120a, 120b via a mount or a portion of the carriage 110a, 110b so that movement of the part of the leaf actuator array 180a mounted to the carriage 110a is not permitted relative to the leaf guide 120a. Though a part of the leaf actuator array 180a is rigidly coupled to the carriage, individual movement of the leaves relative to the carriage is of course permitted, because the leaf actuators have moving parts (i.e. the leaf motor, leaf actuator screw and leaf nut described above) which are arranged to engender relative motion between the individual leaves and the carriage.

The linear motion of the leaf banks 150a, 150b due to actuation by the carriage actuators 115a, 115b is in the same direction as that of the leaves 152 due to the leaf actuators 154. That is, the carriage actuators 115a, 115b are arranged to move the carriages 110a, 110b and hence the leaf banks 150a, 150b, back and forth along a first axis (i.e. in a first direction and a second direction opposite the first direction); and the leaf actuators 154 are arranged to move the leaves 152 back and forth along the same first axis. The first axis is parallel to the longitudinal direction from the tail to the tip of the leaves.

All leaves and carriages can be driven in unison or individually, a control system suitable for monitoring and controlling the position of the leaves and carriages ensures that collisions between leaves and/or between carriages are avoided.

The movement of the carriages and the movement of the individual leaves may be carried out for different purposes. The movement of the individual leaves may be carried out to define the shape of the radiation beam, whereas the movement of the carriages may be carried out in order to move the shaped aperture provided by the leaves relative to the axis of the radiation beam. The movement of the carriages and leaves may be carried out independently of each other and the movements may be carried out sequentially or concurrently depending on the requirements of the application. Multi-leaf collimators of these types allow greater flexibility than those allowing individual leaf motion alone.

The use of moving carriages to move the leaf banks has the potential to lead to inaccuracies in the positioning of the leaves relative to the substrate and/or the radiation beam. The reason for this is that the motion stages on which the carriages move can cause small lateral movement of the carriages (i.e. small movements normal to the plane of the leaves). As the leaf guides are rigidly coupled to the carriages, and the leaves themselves are held laterally by the leaf guides, the lateral movement of the carriages translates into lateral movement of the leaves themselves.

Conventionally, this potential problem is solved by using high tolerancing in the manufacture of the linear translation stage (or stages) on which the carriages travel. As a result of the high tolerancing, the two leaf banks are not misaligned relative to each other, and the ability of the leaves of one of the leaf banks to interdigitate with, or match the position of, the leaves of the other leaf bank is unaffected. However, the high tolerancing required increases the complexity and cost of manufacture of the MLC.

MLC with Leaf Bank Actuator and Static Leaf Guide

Multi-leaf collimators described herein may be arranged with the intention that when the leaf bank is moves as a unit, it is moved relative to the leaf guide. The leaf guide can then be permanently static relative to a beam limiting device in which the multi-leaf collimator is installed.

Figure 11:
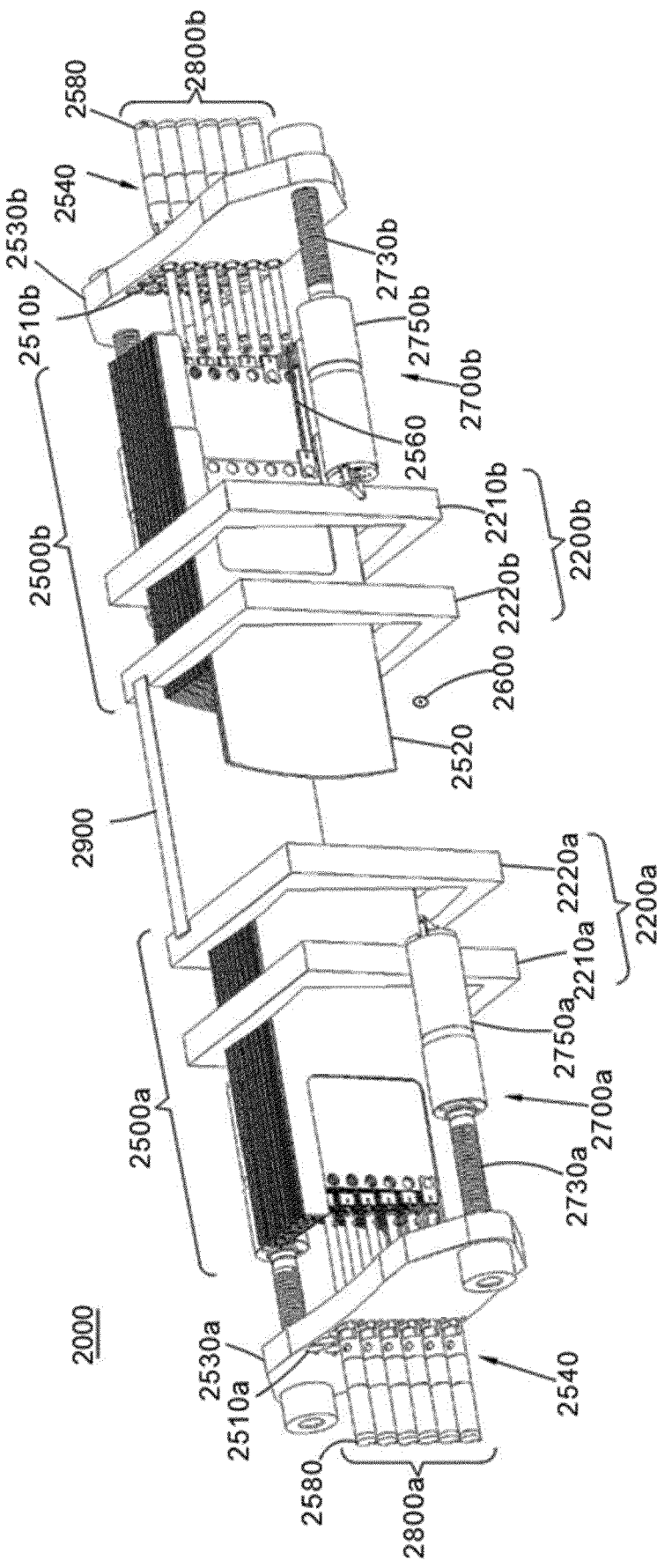
FIG. 11 shows a multi-leaf collimator according to an embodiment.

FIG. 11 shows a multi-leaf collimator 2000 in accordance with an embodiment. The multi-leaf collimator 2000 includes two leaf banks 2500a, 2500b, each leaf bank 2500a, 2500b including a plurality of leaves 2520. The multi-leaf collimator 2000 includes a leaf actuator array 2800a, 2800b for each leaf bank 2500a, 2500b. Each leaf actuator array 2800a, 2800b includes an array of leaf actuators 2540. Each leaf actuator is arranged to engender linear motion of one leaf relative to the other leaves in the leaf bank. The arrays may be similar in form and function to the arrays of leaf actuators 154 shown in FIG. 10. Each leaf bank 2500a, 2500b is supported by a leaf guide 2200a, 2200b.

Leaves

The leaves of the multi-leaf collimator are the parts which define the shape of the aperture. The leaves are plate-like structures arranged side-by-side in a stack, much like playing cards in a deck of cards. The leaves can slide against each other and move independently of each other so that the 'deck' (i.e. the leaf bank) when viewed from the side has an outline at the ends which is defined by the position of the 'cards' (i.e. the leaves) relative to each other. Part of the radiation beam is blocked by the leaf bank so that the beam takes on a shape which is the same as the outline defined by the position of the leaves.

More particularly, the leaves 2520 are each moveable longitudinally within their respective leaf bank 2500a, 2500b so that they can each project into and out of the path of a radiation beam passing through an aperture 2600 between the two opposing leaf banks 2500a, 2500b. The leaves 2520 may be described as plates. The leaves may be substantially rectilinear in shape in the plane thereof. The leaves 2520 may be relatively thin in a direction perpendicular to both the direction of the axis of the beam and plane of the leaves, allowing a high-resolution aperture shape to be obtained. The leaves 2520 may be relatively deep in the direction of the axis of the radiation beam in order to render them sufficiently opaque at X-ray wavelengths/energies. The leaves 2520 may be relatively elongate (relatively long in the direction perpendicular to their thickness and depth), allowing them to adopt a wide range of positions while maintaining contact with the leaf guides. The leaves may comprise a dense material (high atomic number material), such as tungsten, which is capable of absorbing and/or scattering X-rays.

Leaf Guide

The leaf guide is the part of the multi-leaf collimator which prevents the leaves from moving except in the direction which allows them to move back and forth into and out of the path of the radiation beam. Much like the sleeve of a deck of playing cards, the leaf guides may be wrapped around the leaf bank so that the leaves are constrained so that they don't splay apart or fan out. The leaves may not actually contact each other and there may be a very small gap between each leaf. In this case, the leaves may be restrained laterally (i.e. prevented from splaying apart) by grooves in the leaf guides, each groove being arranged to receive a leaf and allowing the leaf to slide or run in the groove in its motion into and out of the path of the radiation beam.

More particularly, the leaves 2520 are guided and supported by leaf guides 2200a, 2200b. The leaf guides 2200a, 2200b are structures which perform the functions of supporting the weight of the leaves 2520 and/or guiding them in their linear motion into and out of the path of the radiation beam. The linear motion is back and forth along a single axis (i.e. the aforementioned first axis parallel to the plane of the leaves and perpendicular to the leading edges of the leaves). That is, each leaf guide 2200a, 2200b constrains movement of a respective leaf bank 2500a, 2500b to a single axis of movement. That is, each leaf guide 2200a, 2200b substantially prevents the movement of a respective leaf bank 2500a, 2500b along a second axis (that parallel to the propagation of the radiation beam when the multi-leaf collimator is in use; that is, the direction parallel to the leading edge of the leaves) and along a third axis (that substantially perpendicular to the plane of a leaf 2520 in the leaf bank 2500a, 2500b). However, each leaf guide 2200a, 2200b allows linear movement of the respective leaf bank 2500a, 2500b and the individual leaves 2520 of that leaf bank back and forth along the first axis.

The leaf guides 2200a, 2200b are differentiated from other components in that they perform said function(s) by being in direct contact with the leaves 2520. Said direct contact may be described as dynamic contact in that the individual leaves 2520 and the leaf bank 2500a, 2500b are moveable with respect to the leaf guide 2200a, 2200b.

Each leaf guide 2200a, 2200b may comprise a frame or support arranged to guide the leaf bank 2500a, 2500b and each of the individual leaves 2520 in their linear motion. Each leaf guide 2200a, 2200b may comprise a frame having an opening through which the leaves are inserted. The opening may be rectilinear in shape to correspond to the cross-sectional shape of the leaf bank 2500a, 2500b, the cross section being taken in the plane perpendicular to the intended direction(s) of movement of the leaf bank into and out of the radiation beam (i.e. a plane parallel to that defined by the aforementioned second and third axes). Each leaf guide 2200a, 2200b may include grooves, protrusions or other features configured to engage with edges of the individual leaves of the leaf bank 2500a, 2500b to guide their movement through the leaf guide 2200a, 2200b and prevent their movement along the second and third axes.

In preferred embodiments, the leaf guides 2200a, 2200b each comprise a first leaf guide unit 2210a, 2210b and a second leaf guide unit 2220a, 2220b spaced from the first leaf guide unit along the first axis, wherein the first leaf guide unit 2210a, 2210b and second leaf guide unit 2220a, 2220b are each in direct contact with the respective leaf bank 2500a, 2500b. The leaf bank actuator 2700a, 2700b is arranged to engender relative linear motion between the leaf bank and both the first leaf guide unit 2210a, 2210b and the second leaf guide unit 2220a, 2220b. That is, the leaf bank actuator is arranged to engender relative linear motion between the leaf bank and the first leaf guide unit 2210a, 2210b, and to also engender relative linear motion between the leaf bank and the second leaf guide unit 2220a, 2220b. The first leaf guide unit 2210a, 2210b and the second leaf guide unit 2220a, 2220b may be rigidly coupled to one another, for example via the base 2900 or via a coupling member.

Alternatively, the leaf guides 2200a, 2200b may each comprise only one leaf guide unit 2210a, 2210b in direct contact with the respective leaf bank 2500a, 2500b.

Advantageously, two or more spaced leaf guide units per leaf guide allow more accurate control of the positioning of the leaves and leaf banks compared with a single leaf guide unit. A longer single leaf guide unit spanning the same-sized portion of the leaves as the two leaf guide units may be used to achieve the same advantageous effect. However, this increases the weight of the multi-leaf collimator, which in turn affects the complexity and/or manoeuvrability of the beam limiting device within which it is installed.

Multi-Leaf Collimator Module

It may be understood that there is provided a module for a multi-leaf collimator comprising one half of the multi-leaf collimator shown in FIG. 11. That is, the module may comprise one leaf bank 2500a, one leaf guide 2200a, one array of leaf actuators 2540, and one leaf bank actuator 2700a arranged in any one or more of the configurations of one half of the multi-leaf collimator 2000 described herein.

It may therefore be understood that there is provided a multi-leaf collimator module for a radiotherapy device, the module comprising a leaf bank supported by a leaf guide; and a leaf bank actuator arranged to engender relative linear motion between the entire leaf bank and the leaf guide.

There is also provided a multi-leaf collimator module for a radiotherapy device, the module comprising: a leaf bank comprising a plurality of leaves; a leaf guide arranged to guide linear movement of the leaves in a first direction and a second direction opposite the first direction, the leaf guide being in direct contact with the leaves; a plurality of leaf actuators, each leaf actuator arranged to engender relative linear motion in the first direction and second direction between one leaf in the leaf bank and other leaves in the leaf bank; and a leaf bank actuator arranged to engender relative linear motion in the first direction and second direction between the entire leaf bank and the leaf guide.

Such modules may be provided alone or provided connected to another similar module to form a dual-leaf-bank multi-leaf collimator such as the one shown in FIG. 11. The modules may each comprise a base 2900, said bases having complementary inter-locating means for coupling the bases to each other. The interlocking means may comprise a groove, slot, recess, mortice or hole for receiving a suitably proportioned ridge, protrusion, tenon or stub. The inter-locating means may comprise interlocking means. The inter-locating means may be arranged to ensure relative alignment between the leaves of one of the modules with the leaves of the other module once the bases are located relative to each other using the inter-locating means.

Alternatively, the respective leaf guides 2200*a*, 2200*b* of the dual-leaf-bank multi-leaf collimator may be coupled to the same mounting structure. The mounting structure may be a base plate, frame or any other structure suitable to rigidly mount the leaf guides thereto. The mounting structure and (each) leaf guide may include a complementary pair of locating means for aligning (each) leaf guide 2200*a*, 2200*b* with the mounting structure. Such locating means may perform the function of allowing an accurate and reliable spatial relationship to be formed between each of the leaf guides 2200*a*, 2200*b* and the mounting structure when the leaf guides are coupled to the mounting structure.

Advantageously, the pair of locating means allows the leaf guide 2200*a*, 2200*b* (and hence the leaves 2520 in the leaf bank 2500*a*, 2500*b*) to be more accurately and reliably aligned relative to the mounting structure. The locating means may comprise a male and female connector pair (for example, a protrusion and a hole, respectively) wherein one of the male and female connector is located on the mounting structure and the other one of the male and female connector is located on the respective leaf guide 2200*a*, 2200*b*. Alternatively, the locating means may comprise two female connectors, one on the mounting structure and one on the leaf guide 2200*a*, 2200*b*, allowing relative alignment between the mounting structure and the leaf guide by a pin or other male connector located partly in the female connector on the mounting structure and partly in the female connector on the leaf guide 2200*a*, 2200*b*.

Alternatively, in use the leaf guides 2200*a*, 2200*b* are each rigidly fixed to a base (or mount or housing or frame) 2900 and/or rigidly fixed to each other. It may therefore be understood that the leaf guides 2200*a*, 2200*b* may be arranged to be static relative the base 2900 in all modes of operation of the multi-leaf collimator 2000. The leaf guides 2200*a*, 2200*b* may therefore remain static not only when leaves 2520 are individually moved by their respective leaf actuators 2540, but also when each leaf bank 2500*a*, 2500*b* is moved by its respective leaf bank actuator 2700*a*, 2700*b*. This may be achieved by rigidly coupling or fixing the leaf guides 2200*a*, 2200*b* to the base 2900 so that no movement between the base 2900 and leaf guides 2200*a*, 2200*b* is allowed, or by machining the leaf guides 2200*a*, 2200*b* and the base 2900 from a single piece of material to form an integral or monolithic structure.

That is, the leaf guide(s) of one leaf bank may be rigidly connected to the leaf guide(s) of the opposing leaf bank either directly or indirectly via the base or a coupling member. That is, in the reference frame of the MLC, the position of the leaf guide(s) of one leaf bank may be fixed relative to the position of the leaf guide(s) of the opposing leaf bank. Advantageously, this provides a more reliable, less complex means of ensuring lateral alignment of the leaves of one leaf bank with the leaves of the opposing leaf bank.

Alternatively, one of the leaf guides 2200*a* may have a mounting structure integrally formed (e.g. monolithically) therewith, the mounting structure being arranged to receive the other leaf guide 2200*b* as described above.

It may therefore be understood that there is provided a multi-leaf collimator comprising a mount, a first multi-leaf collimator module as described herein and a second multi-leaf collimator module as described herein, wherein the respective leaf guides of the first multi-leaf collimator module and second multi-leaf collimator module are fixed to or integral with the mount and the respective leaf banks are arranged to face each other to define an aperture therebetween. The term 'face each other' here may mean that the leading edges of the leaves of one leaf bank face the leading edges of the leaves of the other leaf bank, which leading edges lie perpendicular to the direction(s) of movement of the leaves in the leaf guide. The arrangement of the leaf banks relative to each other is such that the shape of the aperture between them may be modified by movement of the leaves relative to the leaf guides.

Advantageously, as the leaf guides are static relative to the base, their alignment relative to the base and/or to each other can be fixed during manufacture. This provides a reduction in complexity and cost of manufacture of the multi-leaf collimator. Furthermore, the risk of lateral misalignment of the leaves (i.e. misalignment of the leaves in the direction normal to the plane of the leaves) during manufacture and/or in use is significantly reduced. That is, there are advantages to combining a leaf bank actuator as herein described (i.e. one arranged to engender relative motion between the entire leaf bank and the leaf guide) with a leaf guide which is static relative to a base or substrate of the multi-leaf collimator. For example, this configuration minimises lateral movement of the leaves during motion of the leaf bank when the entire leaf bank is moved under the force of the leaf bank actuator. Therefore, reliable and predictable movement of the leaves relative to the radiation beam and the target tissue can be achieved at lower cost and with lower complexity than needed in the prior art MLCs, such as the type shown in FIG. 10.

Embodiments include a first multi-leaf collimator module as described herein and second multi-leaf collimator module as described herein, wherein the leaf guide of the first multi-leaf collimator module is rigidly coupled to the leaf guide of the second multi-leaf collimator module.

That is, embodiments include a first multi-leaf collimator module according as described herein and a second multi-leaf collimator module as described herein, wherein the leaf guide of the first multi-leaf collimator module is arranged to remain static in relation to the leaf guide of the second multi-leaf collimator module during operation of the respective leaf bank actuators.

In the above described embodiments, the relative lateral alignment of a first leaf in one of the leaf banks and a second leaf in the other (opposing) leaf bank can be fixed in the manufacturing process. No or negligible lateral misalignment may occur when those leaves are moved by either their respective leaf actuators or their respective leaf bank actuators. Thus, a more accurately shaped or positioned aperture can be obtained and the leaves of on leaf bank can more reliably interdigitate with the leaves of the opposing leaf bank regardless of the position of the leaf banks along their range of motion.

Leaf Actuator Array/Leaf Actuators

The leaf actuator array is the part of the multi-leaf collimator which causes the individual leaves to move relative to each other. The leaf actuator array includes a leaf actuator for each leaf, each leaf actuator being the part which is responsible for the movement of a respective one of the leaves relative to the other leaves. The group of leaf actuators which operate on all the leaves of one leaf bank can be collectively referred to as the leaf actuator array.

More particularly, for each leaf bank 2500a, 2500b, there is a leaf actuator array 2800a, 2800b. Each leaf actuator array 2800a, 2800b includes an array of leaf actuators 2540 (each comprising e.g. an assembly including a leaf motor, leaf actuator screw and leaf nut). The leaf actuator arrays 2800a, 2800b are arranged to move the leaves 2520 in their respective leaf banks 2500a, 2500b independently of each other and relative to their respective leaf guides 2200a, 2200b. That is, each of the leaf actuators 2540 in the array may be arranged to engender relative linear motion between the leaf 2520 to which they are connected and other leaves in the leaf bank 2500a. Each of the leaf actuators 2540 in the array may be arranged to engender relative linear motion between the leaf 2520 to which they are connected and the leaf guide 2200a.

The leaf actuators 2540 may each comprise a linear electric actuator. The leaf actuators 2540 may comprise an acme screw, ball screw or lead screw assembly. The leaves 2520 themselves may be coupled as a load to the end of a threaded rod acting as a leaf actuator screw 2560. A leaf actuator driving mechanism 2580 (henceforth described as a leaf motor 2580 for brevity) driving the leaf actuator screw may be a DC, DC servo, DC brushless, DC brushless servo, AC, AC servo, or stepper motor. The leaf motor 2580 may be coupled to the leaf actuator screw 2560 at an end opposite to the end of the leaf actuator screw coupled to the leaf.

In FIG. 11, each leaf actuator includes a leaf actuator screw 2560 having one end rigidly coupled to the tail portion of a leaf 2520 (i.e. so as to be prevented from rotating or moving in a linear fashion relative to the leaf) and another end engaged with an internally threaded tube (e.g. a nut) coupled to the leaf motor 2580 and arranged to rotate under the driving force of the leaf motor 2580. Rotation of the threaded tube by the leaf motor 2580 relative to the leaf actuator screw 2560 translates into relative linear movement between the threaded tube and the leaf actuator screw 2560. The linear movement of the leaf actuator screw 2560 translates into linear movement of the leaf 2520 due to the nature of the coupling therebetween.

However, it is not essential that the leaf actuator has the above described configuration. In some embodiments, the leaf actuator includes a leaf actuator screw which is coupled to an output shaft of the motor (or alternatively is the output shaft of the leaf motor). Thus, the leaf actuator screw rotates under the driving force of the leaf motor. A leaf nut having an internally threaded portion is incorporated into, or is mounted or coupled to, the tail portion of the leaf. The leaf nut is rigidly coupled to the tail portion of a leaf (i.e. so as to be prevented from rotating or moving in a linear fashion relative to the leaf) and the internally threaded portion engages with the thread of the leaf actuator screw. Thus, the rotational motion of the leaf actuator screw relative to the leaf nut translates into relative linear motion between the leaf actuator screw and the leaf nut and hence also the leaf. That is, as the leaf actuator screw is rotated by the leaf motor, it drives the leaf nut, and hence the leaf, in the direction parallel to the leaf actuator screw and in the plane of the leaf (i.e. along the first axis into and out of the path of the radiation beam when in use).

A rear or tail edge of the leaf (that is an edge opposite the leading edge of the leaf) may have an inset area to accommodate the leaf motor. The leaf may have an elongate aperture running along a substantial portion of the length of the leaf. The elongate aperture may be accessible to the leaf actuator screw via an internally threaded section (or the aforementioned leaf nut) which engages with the leaf actuator screw.

The stroke of the leaf actuator 2540 may be sufficient to allow the leading edge of the leaf to be extended at least half way into the path of the radiation beam and also retract so that it is clear of the path of the radiation beam. The stroke may therefore be between about one half and about two times the diameter of the radiation beam for which the multi-leaf collimator is designed. The stroke may be between about one quarter the length of one leaf to about the length of one leaf.

Leaf Bank Actuator

The leaf bank actuator is the part of the multi-leaf collimator which moves the whole of the leaf bank as a unit into and out of the path of the radiation beam. The leaf bank actuator moves the leaf bank in the same direction(s) as that in which the leaf actuator moves the leaves.

As described with reference to FIG. 10, the prior art multi-leaf collimators employ a leaf guide which moves together with the leaf bank relative to the beam limiting device. That is, in the prior art, the leaf bank actuator (e.g. carriage) moves the leaf guide and the leaf bank together as one, whereas in the multi-leaf collimator of the type shown in FIG. 11, the leaf bank actuator moves the leaf bank relative to the leaf guide.

In embodiments, the leaf bank actuator moves the leaf bank relative to the leaf guide. In use, the leaf guide is static and the whole of the leaf bank moves back and forth through the leaf guide under the force applied by the leaf bank actuator.

More particularly, the multi-leaf collimator 2000 shown in FIG. 11 includes a leaf bank actuator 2700a, 2700b for each leaf bank 2500a, 2500b. Generally, the leaf bank actuator in accordance with embodiments may be described as an actuator which is arranged to engender relative linear motion between the entire leaf bank and the leaf guide.

Each leaf bank actuator 2700a, 2700b may be coupled at a first end thereof to a respective leaf guide 2200a, 2200b or to the base 2900, and at a second end thereof to the leaf bank 2500a, 2500b, for example via the leaf actuator array 2800a, 2800b. In use, the leaf bank actuator needs only a single anchor point at one end which is static, the other end of the actuator being coupled, directly or indirectly, to the leaf bank so that the leaf bank actuator can move the leaf bank relative to the static anchor point. The static anchor point may be static relative to the reference frame of a beam limiting device in which the multi-leaf collimator is installed. The static anchor point may be the leaf guide, the base or any other location on or in the beam limiting device which is, directly or indirectly, rigidly connected to the leaf guide.

A single leaf bank actuator may be provided for each leaf bank 2500a, 2500b. Each leaf bank actuator 2700a, 2700b is arranged to move its respective leaf bank 2500a, 2500b relative to the leaf guide 2200a, 2200b which supports that leaf bank 2500a, 2500b. That is, each leaf bank actuator 2700a, 2700b is arranged to engender relative linear motion between its respective leaf bank 2500a, 2500b and the leaf guide 2200a, 2200b supporting the leaf bank 2500a, 2500b.

The linear motion of the leaf banks 2500a, 2500b due to actuation by the leaf bank actuators 2700a, 2700b is in the same direction as that of the leaves 2520 due to the leaf actuators 2540. That is, the leaf bank actuators 2700a, 2700b are arranged to move the leaf banks 2500a, 2500b, in the aforementioned first direction and second direction; and the leaf actuators 2540 are arranged to move the leaves 2520 in the first direction and the second direction.

For each multi-leaf collimator module, the leaf bank actuator 2700a, 2700b may be coupled at a first node thereof to the leaf guide and at a second node thereof to the leaf bank 2500a, 2500b. The term node in this context means a location on the leaf bank actuator 2700a, 2700b suitable for fixture of other components thereto. The leaf bank actuator 2700a, 2700b is arranged to engender relative linear motion between the first node and the second node.

The first node may be located at a first end of the leaf bank actuator 2700a, 2700b and/or the second node may be located at a second end of the leaf bank actuator 2700a, 2700b opposite the first end. The first end and second end of the leaf bank actuator 2700a, 2700b may either refer to either absolute ends or end regions of the leaf bank actuator 2700a, 2700b. Advantageously, these locations of the first and second node allow the form and/or size of the multi-leaf collimator to be more compact and the size of a beam limiting device in which the multi-leaf collimator is installed may be reduced, or a form thereof improved. Hence, a size of a treatment head of the radiotherapy device in which the beam limiting device is installed may be reduced, of a form thereof improved.

The leaf bank actuator 2700a, 2700b may be coupled to the leaf bank 2500a, 2500b via the leaf actuator array 2800a, 2800b. The nature the coupling is such that the leaf actuators 2540 may move leaves in the leaf bank 2500a, 2500b independently of each other relative to the leaf guide 2200a, 2200b, while the leaf bank actuators may move the leaves 2520 in the leaf bank 2500a, 2500b in unison relative to the leaf guide 2200a, 2200b by moving the leaf actuators 2540 relative to the leaf guide. The leaf bank actuator 2700a, 2700b may be coupled to the leaf motor, as opposed to the leaf actuator screw.

FIG. 11 shows leaf bank actuator plates 2530a, 2530b which can also be described as mounting plates for mounting the leaf actuators 2540 thereto. Each of the leaf bank actuator plates 2530a, 2530b are positioned behind the trailing edges of the leaves 2520 of their respective associated leaf bank 2500a, 2500b. The plane of the each of the leaf bank actuator plates 2530a, 2530b lies perpendicular to the aforementioned first and second directions. One face of each leaf bank actuator plates 2530a, 2530b faces in the first direction. That is, one face of each of the leaf bank actuator plates 2530a, 2530b faces the trailing edges of the leaves of its respective leaf bank 2500a, 2500b.

All leaf actuators 2540 of a respective leaf bank 2500a are coupled or mounted to the respective leaf bank actuator plate 2530a. The leaf bank actuator plate 2530a, 2530b has a 2D array of through holes 2510a, 2510b therein. Each through hole 2510a, 2510b receives a leaf motor 2580 therein so as to form a rigid coupling between the leaf motor 2580 and the leaf bank actuator plate 2530a, 2530b. The coupling may be made rigid by the use of retainers, such as a screws or bolts (not shown), for fixing the leaf motors to the leaf bank actuator plate 2530a, 2530b.

The second end of each of the leaf bank actuators 2700a, 2700b (i.e. the end opposite the end coupled to the leaf guide 2200a, 2200b) is coupled to the respective leaf bank actuator plate 2530a, 2530b such that linear motion of the second end of the leaf bank actuator 2700a. 2700b in the first and second directions translates into linear motion of the leaf bank actuator plate 2530a, 2530b and hence the leaf motors 2580 attached thereto, in the first and second directions. Thus, each leaf bank actuator 2700a engenders relative linear motion between the leaf bank actuator plate 2530a, 2530b and the leaf guide 2200a, 2200b. Hence, the leaf bank actuator 2700a engenders relative linear motion between all leaf motors 2580 of the respective leaf bank 2500a, 2500b and the leaf guide 2200a, 2200b.

The leaf bank actuators 2700a, 2700b may each comprise a linear electric actuator. The leaf bank actuators 2700a, 2700b may comprise an acme screw, recirculating ball screw or lead screw assembly. The leaf banks 2500a, 2500b may be attached (optionally via the leaf actuator array 2800a, 2800b) as a load to the end of a threaded rod acting as a leaf bank actuator screw 2730a, 2730b. A leaf bank actuator driving mechanism (e.g. leaf bank actuator motor) 2750a, 2750b driving the leaf bank actuator screw 2730a, 2730b may be a DC, DC servo, DC brushless, DC brushless servo, AC, AC servo, or stepper motor. The leaf bank actuator motor 2750a, 2750b may be coupled to the leaf bank actuator screw 2730a, 2730b at an end of the leaf bank actuator screw opposite to that coupled to the leaf bank actuator plate 2530a, 2530b.

In FIG. 11, the leaf bank actuator screws 2730a, 2750b are coupled to an output shaft of the respective leaf bank actuator motor 2750a, 2750b (or alternatively are the output shafts of the leaf bank actuator motors). The leaf bank actuator motor 2750a, 2750b is rigidly coupled, directly or indirectly, to the leaf guide 2200a, 2200b. Thus, the leaf bank actuator screw 2730a, 2730b rotates under the driving force of the leaf bank actuator motor 2750a, 2750b. A leaf bank nut having an internally threaded portion is incorporated into, or is mounted or coupled to, the leaf bank actuator plate 2530a, 2530b. The leaf bank nut is rigidly coupled to the leaf bank actuator plate 2530a, 2530b (i.e. so as to be prevented from rotating or moving in a linear fashion relative to the leaf bank actuator plate) and the internally threaded portion thereof engages with the thread of the leaf bank actuator screw 2730a, 2730b. Thus, the rotational motion of the leaf bank actuator screw 2730a, 2730b relative to the leaf bank nut translates into relative linear motion between the leaf bank actuator screw 273a, 2730b and the leaf bank nut and hence also the leaf bank actuator plate 2530a, 2530b. That is, as the leaf bank actuator screw 2730a, 2730b is rotated by the leaf bank actuator motor 2750a, 2750b, it drives the leaf bank nut, and hence the leaf, in the direction parallel to the axis of the leaf bank actuator screw 2730a, 2730b and in the plane of the leaf 2520 (i.e. along the first axis into and out of the path of the radiation beam when in use).

However, it is not essential that the leaf bank actuator 2700a, 2700b has the above described configuration. In some embodiments, each leaf bank actuator 2700a, 2700b, includes a leaf bank actuator screw having one end rigidly coupled to a respective one of the leaf bank actuator plates 2530a, 2530b (i.e. so as to be prevented from rotating or moving in a linear fashion relative to the leaf bank actuator plate) and another end engaged with an internally threaded tube (e.g. a nut) coupled to the leaf bank actuator motor. The internally threaded tube is arranged to rotate under the power of the leaf bank actuator motor. Rotation of the threaded tube by the leaf bank actuator motor relative to the leaf bank actuator screw 2730a, 2730b translates into relative linear movement between the threaded tube and the leaf bank actuator screw. The linear movement of the leaf bank actuator screw 2730a, 2730b translates into linear movement of the leaf bank actuator plate 2530a, 2530b due to the rigid coupling therebetween.

The stroke of the leaf bank actuator 2700a, 2700b may be sufficient to allow the leading edge of the leaves 2520 to be extended at least half way into the path of the radiation beam and also retract so that it is clear of the path of the radiation beam. The stroke may therefore be between about one half and about two times the diameter of the radiation beam for which the multi-leaf collimator is designed. The stroke may be between about one quarter of the length of one of the leaves and about twice the length of one of the leaves.

As shown in FIG. 11, a pair of leaf bank actuators may be provided per leaf bank. The pair may include one leaf bank actuator having a second end coupled to a first region of the leaf bank actuator plate 2530a adjacent to a first edge, and another leaf bank actuator having a second end coupled to a second region of the leaf bank actuator plate 2530a adjacent to a second edge. The second edge may be opposite to the first edge as shown in FIG. 11. However, embodiments are not limited to this arrangement and the pair of leaf bank actuators may be arranged in other configurations, such as near adjacent sides of the leaf bank actuator plates.

Advantageously, employing two leaf bank actuators per leaf bank provides improved stability and reliability/accuracy in leaf bank movement compared with only a single leaf bank actuator per leaf bank.

Control of the Actuators

A suitable controller will typically be provided (not shown), which is arranged to provide signals to the leaf actuators 2540 and/or the leaf bank actuators 2700a, 2700b in order to move the appropriate leaf or leaves 2520 to provide the required shape or position of the aperture 2600. As the person skilled in the art will appreciate, the leaf actuators 2540 and the leaf bank actuators 2700a, 2700b are connected to suitable drives for converting step, speed and/or direction input from the controller to actuator currents and voltages.

The leaf actuators control the motion of the leaves for the most granular delimitation, that is for controlling the shape of the edge of the aperture, whereas the leaf bank actuators control the motion of the entire leaf bank for the broader delimitation of controlling the overall position of the edge of the aperture. In the treatment environment, the requirements for the granular delimitation (aperture shape) are usually set by the shape of the target tissue (e.g. tumour) to be irradiated, whereas the requirements for the broader delimitation (aperture position) are usually set by the position of the target tissue to be irradiated. The target tissue may move during treatment due to movement of the patient, for example due to chest expansion and contraction during breathing. It is therefore important to accurately control the position of the aperture during treatment using the leaf bank actuators.

Advantageously, in contrast with the multi-leaf collimator shown in FIG. 10, the multi-leaf collimator according to embodiments has static leaf guides during movement of the entire leaf banks under the control of the leaf bank actuators. Therefore, a degree of movement of the leaf banks caused by movement of the leaf guides is eliminated and the position of the aperture is more accurately controlled.

The stability of the leaf guide provided by embodiments also has advantageous effects on the predictability and reliability of the position of individual leaves in the leaf banks. In the prior art multi-leaf collimators, the leaf guide moves with the leaf bank when the leaf bank actuator is in operation. This introduces the potential for disparities between predicted and actual leaf position owing to small, unwanted lateral displacements of the leaf guide, and hence leaves, during travel. In embodiments, since the leaf guide is static, such lateral displacements are minimised and thus the disparity between predicted and actual leaf position is minimised.

Therefore, in embodiments, the interrelationship between the leaf bank, the leaf bank actuator and the leaf guide provides a more predictable, accurate and reliable aperture shape and position. Thus, during treatment, the radiation dose provided to the target tissue can be maximised while the dose applied to healthy tissue surrounding the target tissue can be minimised.

There is presented a beam limiting device for limiting a beam of radiation, the beam limiting device comprising any of the multi-leaf collimators described herein. There is also presented a radiotherapy device comprising said beam limiting device.

There is also provided a method of driving any of the multi-leaf collimator modules described herein, the method comprising driving the leaf bank actuator to engender relative linear motion between the entire leaf bank and the leaf guide.

When the term, leaf bank actuator is used, this may be understood to mean a single actuator arranged to engender relative linear motion between the entire leaf bank and the leaf guide. The leaf actuator array cannot be considered to be a leaf bank actuator falling within this definition, because it contains multiple actuators which individually are incapable of moving the entire leaf bank relative to the leaf guide.

Multi-Leaf Collimator

A multi-leaf collimator includes a leaf bank including a plurality of leaves. The leaves are individually moveable longitudinally within the leaf bank so that they can project into and out of the path of a radiation beam. A multi-leaf collimator may have two opposing leaf banks, wherein the radiation beam passes through an aperture between the banks.

Each leaf is configured to attenuate radiation. The leaves of the multi-leaf collimator define the shape of the aperture. The leaves are plate-like structures arranged side-by-side in a stack, much like playing cards in a deck of cards. The leaves can slide against each other and move independently of each other so that the 'deck' (i.e. the leaf bank) when viewed from the side has an outline at the ends which is defined by the position of the 'cards' (i.e. the leaves) relative to each other. Part of the radiation beam is blocked by the leaf bank so that the beam takes on a shape which is the same as the outline defined by the position of the leaves.

The leaves may be substantially rectilinear in shape in the plane thereof. The leaves are relatively thin in a direction perpendicular to both the direction of the axis of the beam and plane of the leaves, allowing a high-resolution aperture shape to be obtained. The leaves are relatively deep in the direction of the axis of the radiation beam in order to render them sufficiently opaque at X-ray wavelengths/energies. The leaves are relatively elongate (relatively long in the direction perpendicular to their thickness and depth), allowing them to adopt a wide range of positions while maintaining contact with the leaf guides. The leaves comprise a dense material (high atomic number material), such as tungsten, which is capable of absorbing and/or scattering X-rays. A leaf actuator causes an individual leaf to move relative to other leaves in the leaf bank.

Figure 12:
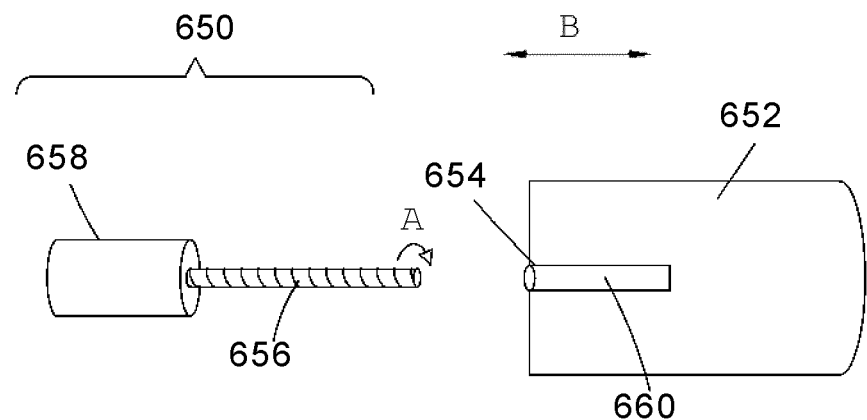
FIG. 12 shows a multi-leaf collimator leaf unit assembly according to the prior art.

FIG. 12 shows a leaf 652 of a multi-leaf collimator and a leaf actuator drive 650 for moving the leaf 652. The leaf 652 and leaf actuator drive 650 are known herein as a "leaf unit".

In a leaf bank comprising a plurality of leaves 652, each leaf will have a respective leaf actuator drive 650.

Each leaf actuator 654 is arranged to drive a respective leaf so that the leaves 652 can be moved in their respective leaf banks independently of each other. That is, each leaf actuator 654 is arranged to engender relative linear motion between one leaf 652 and the other leaves in the leaf bank.

The leaf actuator 654 includes a leaf actuator motor 658. A suitable controller will typically be provided (not shown), which is arranged to provide signals to the leaf actuator motor 658 in order to move the appropriate leaf or leaves 652 to provide the required shape or position of the aperture. All leaves can be driven in unison or individually. A control system suitable for monitoring and controlling the position of the leaves ensures that collisions between leaves of opposing leaf banks are avoided. The movement of the leaves may be carried out define the shape of the aperture (and hence the radiation beam) or to move the shaped aperture provided by the leaves relative to the axis of the radiation beam.

In known systems the leaf actuators may each comprise a leaf actuator screw 656 (e.g. a rotatable threaded rod such as one appropriate for an acme screw, ball screw or lead screw assembly). The leaves 652 themselves are coupled as a load to the end of the leaf actuator screw 656. The leaf actuator motor 658 driving the leaf actuator screw may be a DC, DC servo, DC brushless, DC brushless servo, AC, AC servo, or stepper motor. The leaf actuator motor is coupled to the leaf actuator screw 656 at the opposite end of the leaf actuator screw to the end coupled to the leaf 652.

In known systems the leaf 652 is coupled to the actuator screw with a threaded nut 654. The nut 654 is threadably engaged with the leaf actuator screw 656. The nut 654 is fixedly attached to the leaf 652 so that rotational of the nut around its axis causes corresponding rotation of the leaf. That is, the nut is rotationally fixed relative to the leaf.

The leaf tail (the portion of the leaf 652 at the end of the leaf furthest from the leaf tip) may have an inset area to accommodate parts of the leaf actuator 654. The nut 654 comprises an elongate aperture 660 in the leaf tail running along a substantial portion of the length of the leaf. The elongate aperture 660 is accessible to the leaf actuator screw 656 via an internally threaded section of the nut which engages with the leaf actuator screw 656.

When multiple leaves are arranged in a bank in a multi-leaf collimator, the other leaves in the leaf bank rotationally limit the movement of the leaf 652 but allow linear movement of the leaf 652 in the plane of the leaf. In use the leaf actuator screw 656 is rotated by the leaf actuator motor 658 shown by arrow A. The leaf actuator screw 656 is threadably engaged with the nut 654. However, the nut does not rotate with the leaf actuator screw, because the leaf tail rotationally limits the movement of the nut. Instead the leaf actuator screw 656 interacts with the threaded section in the leaf tail to cause the rotational motion of the leaf actuator screw to be converted into the linear motion of the threaded section and hence the leaf. Rotation of the leaf actuator screw 658 drives the threaded section, and hence the leaf, in the direction parallel to the leaf actuator screw axis and in the plane of the leaf shown by arrow B.

The stroke of the leaf actuator 654 may be sufficient to allow the leading edge of the leaf to be extended at least half way into the path of the radiation beam and also retract so that it is clear of the path of the radiation beam. The stroke may therefore be between about one half and about two times the diameter of the radiation beam for which the multi-leaf collimator is designed. The stroke may be between about one quarter the length of one leaf to about the length of one leaf.

It is noted that in FIG. 12 for illustrative purposes the leaf 652 and the leaf actuator screw 656 are shown de-coupled. In use, the leaf actuator screw 656 is threadably engaged with the nut 654 on the leaf 652.

Known systems use a leaf actuator screw for converting motor torque to linear motion to actuate a leaf. However, these systems have certain limitations.

Trade-Off Between Speed and Accuracy in Conventional Leaf Actuators

The linear speed of the leaf 652 is dependent on the leaf actuator screw 656 pitch and the angular speed of rotation the leaf actuator screw 656. A leaf speed of greater than 5 cm/s is desirable when the multi-leaf collimator is operating in real time to track the tumour silhouette.

A high leaf speed can be achieved in two different ways: rotating the leaf actuator screw with a high rpm; or producing a leaf actuator screw with a large pitch. The leaf actuator screws are leadscrews of the motor.

A large pitch provides greater efficiency in leadscrews. However, a leadscrew with a large pitch involves a number of drawbacks. Leadscrews having a large pitch generally have multi-start threads and have a high helix angle to achieve a large linear displacement of a nut per full rotation of the leadscrew. However, if the efficiency of the leadscrew exceeds 50% it is likely that the actuator will overhaul or back drive. Further, high screw pitch is undesirable in a multi-leaf collimator as it would mean that, at gantry positions in which the leaves are driven against gravity, the leaves may lose position once power is removed from the leaf actuators motors. In addition, is more difficult to accurately position a component when using a high-pitch leaf actuator screw as the control system can "overshoot" the desired position.

Leadscrews with a lower pitch generally have a lower tendency to back drive, are self-locking to a degree and facilitate more accurate positioning with less control system input. However, a leadscrew having a lower pitch has a lower efficiency. To achieve a high linear speed, a leadscrew having a lower pitch needs to be rotated with a greater rotational speed. When rotating leadscrews with a high length to diameter ratio, as leaf actuator screws often have since they are designed to fit within a single leaf-width, there is a critical rotational speed. When a leadscrew reaches its critical speed, it begins to vibrate to an unacceptable degree. This increases wear (which reduces component life), increases noise and reduces efficiency.

The critical speed in a known leaf actuator is constrained due to a number of factors, and the screw cannot be rotated above this limit without causing damage, and maximum possible linear speed of the leaf without causing damage due to vibration is limited.

The critical speed is dependent on leaf actuator screw length, diameter and support bearing configuration.

The leaf width (or pitch between the leaves) dictates the space available for parts of the leaf actuator. For example, the diameter of the leaf actuator screw 656 is limited to the mechanical width of the leaf 652. The length of the leaf actuator screw 656 is chosen in accordance with the leaf travel required for the particular multi-leaf collimator or its application. The support bearing configuration is also limited, since in known leaf actuators it is not possible to support the end of the leaf actuator screw which must be free to allow relative linear motion between the leaf actuator screw and the leaf.

Owing to the above constraints, the critical speed (in rpm) of the known leaf drive screws is limited, and the screw cannot be rotated above this limit without causes damage. Therefore, in the leaf actuator design is also limited in terms of the maximum possible linear speed of the leaf before vibration levels increase to an unacceptable level.

New Leaf Actuator

According to an implementation of the disclosure there is provided a leaf unit incorporating a leaf actuator having a leaf actuator screw which is not rotatable relative to the leaf, as described below.

The leaf unit has an actuator which relies on having a leaf actuator screw which cannot rotate or move in a linear fashion relative to the leaf. This may be achieved by rigidly attaching the leaf actuator screw to the rear of the leaf so that it is not able to rotate. Instead of rotating the leaf actuator screw to cause the leaf to move in a linear fashion, the leaf actuator motor rotates another component which engages with the thread on the leaf actuator screw and pushes or pulls the leaf actuator screw relative to the component so that the leaf actuator screw moves together with the leaf. Thus, the function of the leaf actuator screw is to provide linear motion only, i.e. to push and pull the leaf.

In a preferred arrangement, the leaf actuator screw is coupled at one end thereof to the leaf (e.g. the leaf tail) so that it cannot rotate relative to the leaf. A nut, or other rotatable part (e.g. a worm), engaged with the thread on the leaf actuator screw is arranged to be rotated by the leaf actuator motor such that the leadscrew, and hence the leaf, moves in a linear motion relative to the nut. Thus, as the motor rotates the nut, the leaf actuator screw and the leaf are driven in a linear motion so that the leading edge of the leaf moves into and out of the path of the radiation beam. The nut (e.g. leaf actuator screw nut), which in the rotating leaf actuator screw leaf actuator design would be coupled to the leaf tail, is now mounted in the end of a rotatable tube. The tube is then coupled to the motor and gearbox assembly. The length of the tube is sufficiently long that the leaf actuator screw can be withdrawn within its length.

Figure 13:
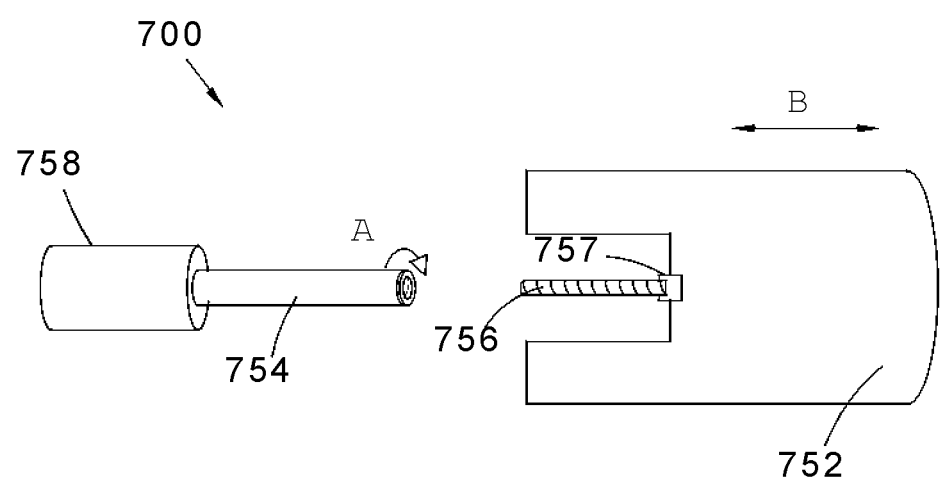
FIG. 13 shows a multi-leaf collimator leaf unit according to an embodiment.

FIG. 13 illustrates an implementation of the present disclosure. A leaf unit 700 includes a leaf 752 and a leaf actuator 750. The leaf actuator includes a leaf actuator screw 756 (e.g. one suitable for a lead screw arrangement), a leaf actuator motor 758, and a rotatable part 754. The leaf actuator screw 756 is coupled at a first end thereof to the leaf tail via a coupling part 757. The coupling part 757 comprises a small plate or shim with a first receiving portion arranged to receive the first end of the leaf actuator screw 756 and a second receiving portion arranged to receive a protrusion on the leaf 752. The leaf actuator screw comprises external threading.

A portion of the leaf actuator screw 756 distal from the first end is inserted into a rotatable part 762 comprising a tube or sleeve. When the leaf actuator is inserted into the rotatable part the rotatable part envelops a section of the leaf actuator screw 756. The rotatable part 754 includes a threaded part on an interior surface thereof to be engaged with at least a part of the distal portion of the leaf actuator screw 756. The rotatable part 754 is rotatable around the axis of the leaf actuator screw 756 by the leaf actuator motor 758. The leaf actuator screw 756 is not rotatable around its own axis due to its coupling at the first end to the leaf tail.

In operation, the leaf actuator motor 758 rotates the rotatable part 754 around the axis of the leaf actuator screw 756, shown by arrow A. The threaded section on the internal surface of the rotatable part 754 acts to translate the relative rotational motion between the rotatable part 754 and the leaf actuator screw 756 into relative linear motion between the rotatable part 754 and the leaf actuator screw 756. The leaf actuator screw 756 applies a force to the leaf 752 and the leaf 752 moves together with the leaf actuator screw 756 in a linear motion relative to the rotatable part 754 and the leaf actuator motor 758.

In FIG. 13 for illustrative purposes the leaf 752 and the rotatable part 754 are shown de-coupled. In use the rotatable part 754 is threadably engaged with the leaf actuator screw 756 on the leaf 752.

Figure 14:
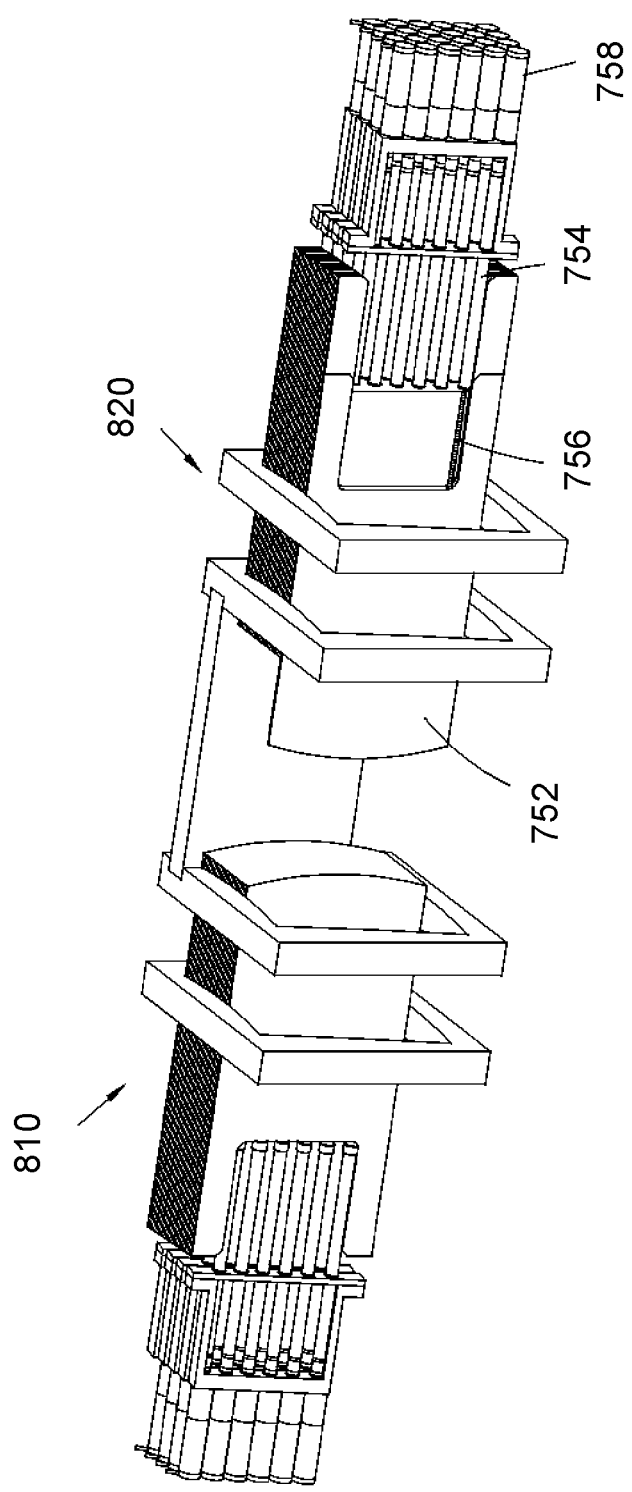
FIG. 14 shows a multi-leaf collimator according to an implementation.

FIG. 14 shows a multi-leaf collimator according to an implementation. The multi-leaf collimator includes a first bank of leaves 810 and a second bank of leaves 820, the two leaf banks being opposed about an aperture. A leaf 752 in the second bank of leaves is in the fully extended position. This can be seen by the alignment between the tips of the leaves—the tip of the leaf 752 protrudes into the aperture between the two leaf banks. The tip of leaf 752 extend further into the aperture than any other leaves in the second leaf bank 820, which are all aligned and in the retracted position. The leaves in the first leaf bank 810 are all retracted and aligned.

As shown for leaf 752, in a fully extended state, the majority of the length of the leaf actuator screw 756 is outside of the rotatable part 754, with the end of the thread of the leaf actuator screw 756 most distal from the first end is still being engaged with the threaded part of the rotatable part 754. In this state, the distance between the rotatable part 754 and the leaf 752 is maximal. In a fully retracted state, the majority of the length of the leaf actuator screw 756 is inside the rotatable part 754 and the distance between the leaf 752 and the rotatable part 754 is minimal.

In FIG. 14, leaf 752 is in the fully extended position, and the leadscrew 756 is visible and not enveloped by the rotatable part 758. Leaf 852 in the opposing bank is in the fully retracted state and the leadscrew is fully enveloped by the rotatable part such that the leadscrew is not visible in FIG. 14.

In a specific example, the aperture of a multi-leaf collimator is at Iso centre of 5 mm. The multi-leaf collimator has 160 leaves and the leaf width is approx. 1.7-2 mm wide. The leaf travel is approximately 100 mm. In this example, the leaf actuator screws are no more than 2 mm in diameter and at least 100 mm long.

Figure 15:
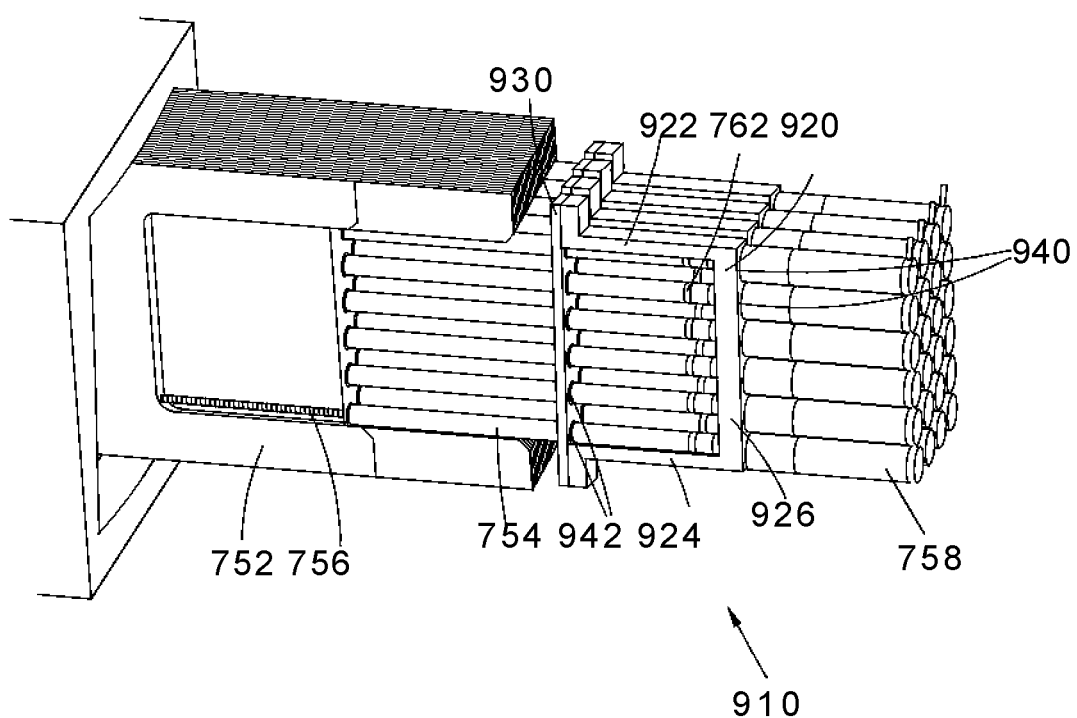
FIG. 15 shows a view of the multi-leaf collimator of FIG. 14.

As shown in FIG. 15 a series of six leaf actuators are mounted in a square-shaped bracket 910.

The bracket 910 includes a first bracket portion 920 having two arms 922, 924 and an elongate plate portion 926 provided between the two arms so as to form a U shape making up three sides of the square shape of the bracket 910. The elongate plate portion 926 has a series 940 of six through holes therein, each through hole of the first series 940 dimensioned so as to receive and support a leaf actuator motor 758. The first bracket portion 920 holds each leaf actuator motor 758 by its motor casing by applying a torque resistance to prevent rotation of the motor casing relative to the first bracket. The first bracket portion 920 also applies a linear force resistance to the motor casing in the direction of the axis of the leaf actuator motor 758 to prevent linear movement of the motor casing relative to the first bracket portion 920.

The bracket also includes a second bracket portion 930 which is provided between the ends of the two arms 922, 924 so as to create the square shape of the bracket 910. The second bracket portion 930 is an elongate plate having second series 942 of six through holes therein, the through holes each having a bearing therein arranged to receive and support a respective tube (rotatable part 754) of the leaf actuators. Advantageously, the shape of the bracket 770 provides a light, yet stable, support for the leaf actuators mounted therein. Further advantageously, the bracket provides stability for the rotatable parts especially at high rotational speeds, which increases the maximum possible critical speed and hence the maximum possible efficiency of the rotatable parts 754. The bracket also helps to reduce noise and vibration of the rotatable part 754 at all speeds, more so at high speeds.

The respective centres of the first series 940 of through holes are aligned with those of the second series 942 of through holes so that the axes of the leaf actuator motor 758 and rotatable part 924 of each leaf actuator are collinear when the leaf actuators are mounted in the bracket 910. When incorporated into the leaf unit, the second bracket portion 930 is positioned nearer the leaf tail than the elongate plate portion 926 of the first bracket portion 920. The first bracket portion 920 is removably coupled to the second bracket portion 930 via a screw fastening a foot at the end of each of the arms 922, 924 to respective end portions of the second bracket portion 930. Advantageously, this allows dismantling of the bracket and easy removal and replacement of the leaf actuators 754 for maintenance and repair.

As shown in FIG. 15, the rotatable part 754 is formed as a tube with a threaded part on the interior surface. The rotatable part 754 attached to the motor 758 features a series of machined slots 762 which facilitate a flexible coupling system between the leaf actuator motor output shaft and rotatable part 754. The machined slots are patterned such that the rotatable part 754 remains integrally formed as a single piece component because no one slot runs around the entire circumference of the rotatable part 754. The machined slots are provided through the wall of the rotatable part 754 to each extend around a portion of the circumference of the rotatable part 754. The slots are offset from each other in the direction of the axis of the rotatable part 754 and the start and end position of any one slot are offset from those of the around the circumferential direction of the rotatable part 754. This provides some flexibility in the connection between the motor output shaft and the rotatable part 754. The slots allow bending of the rotatable part so that its axis is no longer completely parallel to (i.e. forms an acute angle with) the axis of the motor output shaft. Advantageously, small misalignments between the leaf actuator motor mounting and leaf/leaf actuator screw can be accommodated.

The leaf actuator screw can be made from any solid material. Particularly suitable materials are those having low corrosion low wear, high strength and/or low density. Materials which are light and stiff are most suitable.

For example, the leaf actuator screw material can be aluminium, steel, titanium or any alloys thereof, or a composite material such as carbon fibre composite.

Control of the Actuators

A suitable controller will typically be provided (not shown), which is arranged to provide signals to the leaf actuators 750 in order to move the appropriate leaf or leaves 752 to provide the required shape or position of the aperture. As the person skilled in the art will appreciate, the leaf actuators 754, in particular the leaf actuator motors 758, are connected to suitable drives for converting step, speed and/or direction input from the controller to actuator currents and voltages.

In the above implementations, the motors are aligned with the line of movement which they are driving. This is design is known as a "direct drive".

Advantages

Advantageously, the leaf unit according to embodiments allows for a high leaf speed because the leaf actuator screw is rotationally static. Therefore, vibration of the leaf actuator screw due to revolutions thereof is eliminated. The leaf actuator screw can still be manufactured to fit within the width of the leaf as no increase to the diameter thereof is required to maintain stability. The rotatable part can have a larger diameter than that of the leaf actuator screw, because it is not as constrained by the thickness of the individual leaves. The rotatable part has a higher critical speed than the leaf actuator screw due to the larger diameter. Therefore, the rotatable part can operate at higher rotational speeds than the leaf actuator screw without reaching its critical speed and causing damage due to vibrations.

The higher rotational speed of the rotatable part directly translates to a higher linear speed of the leaf. Thus, for the same leaf actuator screw pitch, higher leaf speed is possible without compromising on stability and durability of the leaf actuator. Therefore, the advantages of a low pitch leadscrew, (improved positioning performance and self-locking) can be encompassed into the leaf actuator design. The leaf actuator can have high rotational speed and thus provided a high leaf speed, without the limiting factors previously discussed.

The disclosed leaf unit design allows faster leaf speeds without suffering from the aforementioned difficulties with vibration, leaf position accuracy or control system complexity. The alternative design has all the advantages of the direct-drive leaf actuator design but avoids the associated problems of reaching critical speeds and overhauling of leadscrews.

Therefore, in embodiments, the leaf actuator provides a fast, accurate and reliable change in aperture shape and/or position. Thus, during treatment, the radiation dose provided to the target tissue can be maximised while the dose applied to healthy tissue surrounding the target tissue can be minimised, even if the patient, and hence the tumour, is moving.

There is presented a multi-leaf collimator, or a beam limiting device, for limiting a beam of radiation. The multi-leaf collimator comprises a leaf, the beam limiting device comprising any of the multi-leaf collimators described herein. There is also presented a radiotherapy device comprising said beam limiting device.

There is also provided a method of driving leaves of the multi-leaf collimators described herein, the method comprising driving the leaf actuators to engender relative linear motion between the leaves in at least one leaf bank.

It may be understood that when the terms 'parallel', 'perpendicular' or 'in the plane of' are used to describe the relative arrangement of features and components, small deviations therefrom are permitted provided that they do not affect the functional and/or operational aspects of the multi-leaf collimator modules described herein.

Features of the above aspects can be combined in any suitable manner. It will be understood that the above description is of specific embodiments by way of aspect only and that many modifications and alterations will be within the skilled person's reach and are intended to be covered by the scope of the appendant claims.

Also disclosed herein are the following numbered clauses:
A1. A leaf for a multi-leaf collimator, the leaf comprising:
a leaf portion for delineating a beam of radiation, the leaf portion having first attenuation factor; and
a tail portion having a second attenuation factor, the first attenuation factor being greater than the second attenuation factor.

A2. The leaf according to clause A1, wherein the first attenuation factor divided by the mean length of the leaf portion is greater than the second attenuation factor divided by the mean length of the tail portion.

A3. The leaf according to clause A1, wherein the first attenuation factor divided by the mean width of the leaf portion is greater than the second attenuation factor divided by the mean width of the tail portion.

A4. The leaf according to clause A1, wherein the first attenuation factor divided by the area of a face of the leaf portion is greater than the second attenuation factor divided by the area of a face of the tail portion.

A5. The leaf according to any preceding clause, wherein the leaf portion comprises a first material and the tail portion comprises a second material different from the first material.

A6. The leaf according to clause A5, wherein the first material has a higher atomic number than the second material.

A7. The leaf according to clause A5 or A6, wherein the second material is more ductile than the first material.

A8. The leaf according to any of clauses A5-A7, wherein the first material has a higher linear attenuation coefficient than the second material.

A9. The leaf according to any preceding clause, wherein the leaf portion and tail portion are monolithic.

A10. The leaf according to any preceding clause, wherein the leaf portion and tail portion are modular and the leaf portion is rigidly coupled to the tail portion.

A11. The leaf according to clause A10, wherein at a joint between the leaf portion and tail portion, the leaf portion overlaps the tail portion.

A12. The leaf according to any preceding clause, wherein the leaf portion has a greater minimum thickness than the tail portion.

A13. The leaf according to any preceding clause, wherein the leaf portion has a greater mean thickness than the tail portion.

A14. The leaf according to any preceding clause, wherein the leaf portion has a greater mean width than the tail portion.

A15. The leaf according to any preceding clause, wherein the tail portion includes a recessed portion for receiving at least a part of a leaf actuator component.

A16. The leaf according to clause A15, wherein recessed portion is recessed from a face of the tail portion.

A17. The leaf according to clause A15 or 16, wherein the recessed portion includes one or more of the following:
a slot for receiving a leaf actuator screw;
a slot for receiving a leaf nut;
a seat for receiving a leaf nut holder;
a groove for receiving a leaf nut or leaf nut holder corresponding to an adjacent leaf.

A18. A multi leaf collimator including a leaf according to any preceding clause.

A19. A radiotherapy device including the multi leaf collimator according to clause A18.

B1. A mount for an array of leaf drive units corresponding to a single leaf bank of a multi-leaf collimator, the mount comprising:
a plurality of separable mounting plates, each mounting plate comprising an array of mounting holes, each mounting hole arranged to receive a respective one of the leaf drive units.

B2. The mount according to clause B1, wherein the centre points of mounting holes in the array are aligned in columns extending in a first direction and in rows extending in a second direction oblique to the first direction.

B3. The mount according to clause B1, wherein the centre points of mounting holes in the array are aligned in columns extending in a first direction, and at least one edge of each of the mounting plates is parallel to the first direction.

B4. The mount according to clause B1, wherein the centre points of mounting holes in the array are aligned in columns extending in a first direction and in rows extending in a second direction oblique to the first direction,
a first edge each of the mounting plates is parallel to the first direction, and
a second edge of each of the mounting plates is parallel to the second direction.

B5. The mount according to according to any of clauses B1-B4, wherein the plurality of mounting plates includes a first mounting plate and a second mounting plate arranged adjacent to the first mounting plate,
the mounting hole centre points in the first mounting plate are arranged in a first series of columns and the mounting hole centre points in the second mounting plate are arranged in a second series of columns,
adjacent columns in the first and second series of columns have a first spacing therebetween,
a column in the first series of columns closest to the second mounting plate and the column in the second series of columns closest to the first mounting plate have a second spacing therebetween, the second spacing being equal to the first spacing.

B6. The mount according to according to any of clauses B1-B5, wherein the mount includes a plurality of retainers attached to the mounting plates, each retainer arranged to rigidly couple a respective leaf drive unit to one of the mounting plates.

B7. The mount according to clause B6, wherein each retainer is positioned adjacent to a respective one of the mounting holes and includes:
a head including a retaining face arranged to face the mounting plate,
a shaft extending from the head and arranged to rotatably engage with the mounting plate such that rotation of the retainer about the axis of the shaft moves the retaining face closer to or further from the mounting plate.

B8. A multi-leaf collimator comprising:
the mount of any of clauses B1-B7;
a leaf bank including an array of individually moveable leaves;
an array of leaf drive units, each leaf drive unit received in a respective mounting hole and configured to drive the linear movement of a respective leaf.

B9. The multi-leaf collimator according to clause B8 when comprising the mount of clause B6 or B7, wherein each leaf drive unit includes:
a motor comprising a casing including an engaging member, wherein
at a first rotational position of the casing the engaging member engages the retainer to couple the casing to the mounting plate; and
at a second rotational position of the casing the engaging member is disengaged from the retainer.

B10. The multi-leaf collimator according to clause B9, wherein the engaging member is a flange having a recess.

B11. The multi-leaf collimator according to clause B9 or B10, wherein the casing includes a locating member arranged to engage with the retainer when the motor casing is at the second rotational position so as to prevent further rotation of the motor casing once the motor casing has reached the second position.

B12. The multi-leaf collimator according to any of clauses B9-611, wherein the retainer engages the engaging member of more than one motor casing.

B13. A drive arrangement for a multi-leaf collimator comprising:
- a mounting plate for mounting a leaf drive unit;
- a retainer attached to the mounting plate;
- a motor configured to actuate a leaf of the multi-leaf collimator, the motor comprising a casing including an engaging member, wherein
  - at a first rotational position of the casing the engaging member engages the retainer to couple the casing to the mounting plate; and
  - at a second rotational position of the casing the engaging member is disengaged from the retainer.

B14. The drive arrangement according to clause B13, wherein each retainer is positioned adjacent to a respective one of the mounting holes and includes:
- a head including a retaining face arranged to face the mounting plate,
- a shaft extending from the head and arranged to rotatably engage with the mounting plate such that rotation of the retainer about the axis of the shaft moves the retaining face closer to or further from the mounting plate.

B15. The drive arrangement according to clause B13 or B14, wherein the engaging member is a flange having a recess.

B16. The drive arrangement according to any of clauses B13-B15, wherein the casing includes a locating member arranged to engage with the retainer when the motor casing is at the second rotational position so as to prevent further rotation of the motor casing once the motor casing has reached the second position.

B17. A multi leaf collimator including the drive arrangement according to any of clauses B13-B16, wherein the retainer engages the engaging member of more than one motor casing C1. A multi-leaf collimator module for a radiotherapy device, the module comprising:
- a leaf bank comprising a plurality of leaves;
- a leaf guide arranged to guide linear movement of the leaves in a first direction and a second direction opposite the first direction, the leaf guide being in direct contact with the leaves;
- a plurality of leaf actuators, each leaf actuator arranged to engender relative linear motion in the first direction and second direction between one leaf in the leaf bank and other leaves in the leaf bank; and
- a leaf bank actuator arranged to engender relative linear motion in the first direction and second direction between the entire leaf bank and the leaf guide.

C2. The multi-leaf collimator module according to clause C1, wherein the leaf bank actuator is coupled at a first end thereof to the leaf guide and at a second end thereof to the leaf bank.

C3. The multi-leaf collimator module according to clause C2, wherein the leaf bank actuator is coupled at the second end thereof to the leaf bank via the leaf actuators.

C4. The multi-leaf collimator module according to clause C3, wherein each leaf actuator is coupled at a first end thereof to the second end of the leaf bank actuator and a second end thereof to said one leaf.

C5. The multi-leaf collimator module according to clause C1 or C2, wherein each leaf actuator is coupled at a first end thereof to the leaf bank actuator and at a second end thereof to said one leaf.

C6. The multi-leaf collimator module according to any of clauses C1-05, wherein the leaf bank actuator is arranged to engender relative linear motion between the entire leaf bank and the leaf guide by engendering relative linear motion between the plurality of leaf actuators and the leaf guide.

C7. The multi-leaf collimator module according to any of clauses C1-C6, wherein the leaf guide comprises a first leaf guide unit and a second leaf guide unit spaced from the first leaf guide unit in the first direction, wherein the first leaf guide unit and second leaf guide unit are in direct contact with the leaf bank.

C8. A multi-leaf collimator comprising a mount, a first multi-leaf collimator module according to any of clauses C1-C7, and a second multi-leaf collimator module according to any of clauses C1-C7, wherein the respective leaf guides of the first multi-leaf collimator module and second multi-leaf collimator module are fixed to or integral with the mount and leading ends of the respective leaf banks are arranged to face each other to define an aperture therebetween.

C9. A multi-leaf collimator comprising a first multi-leaf collimator module according to any of clauses C1-C8, and a second multi-leaf collimator module according to any of clauses C1-C8, wherein the leaf guide of the first multi-leaf collimator module is rigidly coupled to the leaf guide of the second multi-leaf collimator module.

C10. A multi-leaf collimator comprising a first multi-leaf collimator module according to any of clauses C1-C9 and a second multi-leaf collimator module according to any of clauses C1-C9, wherein the leaf guide of the first multi-leaf collimator module is arranged to remain static in relation to the leaf guide of the second multi-leaf collimator module during operation of the respective leaf bank actuators.

C11. A beam limiting device comprising the multi-leaf collimator of clauses C8, C9 or C10 or the multi-leaf collimator module according to any of clauses C1-C7.

C12. The beam limiting device of clause C11, further comprising a controller arranged to drive the leaf bank actuator to engender relative linear motion between the entire leaf bank and the leaf guide.

C13. A radiotherapy device comprising the beam limiting device of clause C11 or C12.

C14. A method of driving the multi-leaf collimator module according to any of clauses C1-C7, the method comprising driving the leaf bank actuator to engender relative linear motion between the entire leaf bank and the leaf guide.

D1. A leaf unit assembly for a multi-leaf collimator, the leaf unit assembly comprising:
- a leaf;
- a leaf actuator screw having a first end fixedly attached to the leaf; and
- a rotatable part threadably engaged with the leaf actuator screw.

D2. The leaf unit assembly according to clause D1, wherein the first end of the leaf actuator screw is coupled to the leaf so as to prevent relative rotational motion between the leaf and the leaf actuator screw around the axis of the leaf actuator screw.

D3. The leaf unit assembly according to clause D1 or clause D2, wherein the leaf actuator screw has a second end opposite the first end, wherein the rotatable part is a tube which envelops the second end of the leaf actuator screw.

D4. The leaf unit assembly according to any of clauses D1-D3, wherein, upon rotation of the rotatable part relative to the leaf, the rotatable part is configured to engender relative linear motion between itself and the leaf.

D5. The leaf unit assembly according to any of clauses D1-D4, wherein the leaf actuator screw is configured to move between an extended position in which the majority of the leaf actuator screw is outside the rotatable part, and a retracted position in which the majority of the leaf actuator screw is enveloped by the rotatable part.

D6. The leaf unit assembly according to any of clauses D1-D5, wherein the rotatable part comprises a plurality of slots, each slot extending around a portion of the circumference of the rotatable part, the slots being offset from each other in the direction of the axis of the rotatable part.

D7. The leaf unit assembly according to any of clauses D1-D6, further comprising a leaf actuator motor coupled to the rotatable part.

D8. The leaf unit assembly according to clause D7, wherein the rotatable part has a first end threadably engaged with the leaf actuator screw and a second end coupled to the leaf actuator motor.

D9. A leaf unit assembly according to any of clauses D1-D8, wherein the leaf actuator screw has a diameter of 2 mm or less, and/or a length of 100 mm or greater.

D10. A multi-leaf collimator for a radiotherapy device, the multi-leaf collimator comprising a leaf bank including a plurality of leaf unit assemblies according to any of clauses D1-D9, wherein the rotational movement of the leaves relative to each other is restricted such that rotation of each rotatable part imparts linear motion of the respective leaf actuator screw and leaf relative to the rotatable part.

D11. The multi-leaf collimator according to clause D10, wherein rotatable part of each leaf unit assembly is operable to move the respective leaf in a linear motion independently of the other leaves in the leaf bank.

D12. The multi-leaf collimator according to clause D10 or clause D11, further comprising a support bracket for supporting the motor and/or the rotatable parts of the leaf unit assemblies.

D13. The multi-leaf collimator according to clause D12, wherein the support bracket comprises a first portion and a second portion, the first portion comprising a first series of openings each dimensioned to receive and support a leaf actuator motor, and the second portion comprises a second series of openings each having a bearing therein arranged to receive and support a rotatable part.

D14. The multi-leaf collimator according to clause D13, wherein respective centres of the first series of openings are aligned with those of the second series of openings so that the axes of the leaf actuator motor and rotatable part of each leaf actuator are collinear when the leaf actuators are mounted in the support bracket.

D15. The multi-leaf collimator according to any of clauses D13 or D14, wherein the first portion is removably attached to the second portion.

D16. A radiotherapy device comprising a multi-leaf collimator according to any of clauses D10 to D15.

E1. A leaf for a multi-leaf collimator, the leaf comprising a tail portion adjoined to a leaf portion by a locking joint.

E2. The leaf according to clause E1, wherein the locking joint mechanically prevents separation of the tail portion and the leaf portion by a first force acting in the plane of the leaf.

E3. The leaf according to clause E2, wherein the first force acts in a longitudinal direction of the leaf.

E4. The leaf according to clause E3, wherein the longitudinal direction extends from an edge of the tail portion to an edge of the leaf portion.

E5. The leaf according to any of clauses E1-E4, wherein the locking joint is a dovetail joint.

E6. The leaf according to clause E5, wherein the dovetail joint is a sliding dovetail joint or a half-blind dovetail joint.

E7. The leaf according to any of clauses E1-E6, wherein the locking joint mechanically allows separation of the tail portion and leaf portion by a force acting perpendicular to the plane of the leaf.

E8. The leaf according to any of clauses E1-E7, wherein one of the tail portion and leaf portion comprises a protrusion, the other of the tail portion and leaf portion comprises a corresponding recess and the protrusion and recess interlock to form the locking joint.

E9. The leaf according to any of clauses E1-E8, wherein the tail portion comprises a first material and the leaf portion comprises a second material which is different from the first material.

E10. The leaf according to any of clauses E1-E9, wherein the locking joint mechanically prevents any linear or rotational movement of the leaf portion and tail portion relative to each other in the plane of the leaf.

The invention claimed is:

1. A leaf assembly for a multi-leaf collimator, the leaf assembly comprising:
   a leaf; and
   a leaf nut removably mounted within a profile of the leaf, the leaf nut comprising a threaded hole for receiving a leaf actuator screw oriented along a first axis in a plane of the leaf, the leaf nut being mounted within the leaf such that relative movement between the leaf nut and the leaf is prevented both linearly along the first axis and rotationally about the first axis, wherein movement of the leaf nut relative to the leaf along a second axis is limited between a first and second position along the second axis, wherein the second axis lies across the first axis and is in the plane of the leaf.

2. The leaf assembly according to claim 1, wherein the leaf nut and leaf have interlocking parts so that the leaf nut is movable from a third position, in which the leaf nut is interlocked with the leaf, along an axis to a fourth position in which the leaf nut is free from the leaf.

3. The leaf assembly according to claim 2, wherein the leaf includes a slot for receiving at least a portion of the leaf nut and the leaf nut is arranged to move between the third position and the fourth position along the slot.

4. The leaf assembly according to claim 2, wherein the first axis defines a first direction and a second direction opposite the first direction and wherein the leaf nut is movable along the second direction from the third position to the fourth position.

5. The leaf assembly according to claim 2, wherein the leaf or the leaf nut includes a stop for preventing movement of the leaf nut along the axis from the third position away from the fourth position.

6. The leaf assembly according to claim 4, further comprising:
   a leaf nut holder removably coupled to the leaf and including a stop for preventing movement of the leaf nut from the third position toward the fourth position.

7. The leaf assembly according to claim 6, wherein when the leaf nut holder is coupled to the leaf, movement of the leaf nut holder relative to the leaf is prevented.

8. The leaf assembly according to claim 6, wherein the leaf nut holder includes:
   a blind slot for receiving an edge of the leaf and preventing movement of the leaf nut holder relative to the leaf along the first direction and/or out of the plane of the leaf.

9. The leaf assembly according to claim 6, wherein the leaf includes:
a seat recessed from a face thereof for receiving the leaf nut holder, wherein the seat is arranged to prevent movement of the leaf nut holder at least one axis.

10. The leaf assembly according to claim 6, wherein:
the leaf nut and/or the leaf nut holder has a first cross-sectional profile in a plane perpendicular to both the plane of the leaf and the first axis; and
the leaf includes a recess having a second cross-sectional profile on one face thereof matching at least a part of the first cross-sectional profile so that it can receive a respective leaf nut and/or the leaf nut holder corresponding to the leaf assembly of an adjacent leaf.

11. The leaf assembly according to claim 1, wherein the second axis lies perpendicular to the first axis.

12. The leaf assembly according to claim 6, wherein the leaf nut holder is arranged to allow movement of the leaf nut relative to the leaf along the second axis from the first position to the second position.

13. The leaf assembly according to claim 1, wherein the leaf nut comprises an engaging portion configured to engage the leaf to constrain rotational movement of the leaf nut relative to the leaf about the first axis.

14. A multi leaf collimator including a leaf assembly, the leaf assembly comprising:
a leaf, and
a leaf nut removably mounted within a profile of the leaf, the leaf nut comprising a threaded hole for receiving a leaf actuator screw oriented along a first axis in a plane of the leaf, the leaf nut being mounted within the leaf such that relative movement between the leaf nut and the leaf is prevented both linearly along the first axis and rotationally about the first axis, wherein movement of the leaf nut relative to the leaf along a second axis is limited between a first and second position along the second axis, wherein the second axis lies across the first axis and is in the plane of the leaf.

15. The multi leaf collimator of claim 14, wherein the multi leaf collimator is included in a radiotherapy device.

* * * * *